United States Patent [19]

Bertsch et al.

[11] Patent Number: 5,637,712
[45] Date of Patent: Jun. 10, 1997

[54] PROCESS OF PREPARING ISOQUINOLINE COMPOUNDS

[75] Inventors: Carl F. Bertsch; Bret Huff; Michael J. Martinelli, all of Indianapolis, Ind.

[73] Assignee: Eli Lilly and Company, Indianapolis, Ind.

[21] Appl. No.: 343,079

[22] Filed: Nov. 21, 1994

Related U.S. Application Data

[62] Division of Ser. No. 111,747, Aug. 25, 1993, Pat. No. 5,399,696, which is a division of Ser. No. 939,780, Sep. 3, 1992, Pat. No. 5,284,957.

[51] Int. Cl.$^6$ .............................................. C07D 217/06
[52] U.S. Cl. ........................................................ 546/147
[58] Field of Search ............................................ 546/147

[56] References Cited

U.S. PATENT DOCUMENTS 4,902,695  2/1990  Ornstein ......................... 514/307

OTHER PUBLICATIONS

Sheardown et al., "2,3-Dihydroxy-6-nitro-7-sulfamoyl-benzo (F) quinoxaline: A Neuroprotectant for Cerebral Ischemia", *Science*, 247, 571–574 (1990).

Buchan et al., "Delayed AMPA receptor blockade reduces cerebral infarction induced by focal ischemia", *Neuroreport*, 2, 473–476 (1991).

LePeillet et al., "The non-NMDA antagonists, NBQX and GYKI 52466, protect against cortical and striatal cell loss following transient global ischaemia in the rat", *Brain Research*, 571, 115–120 (1992).

Ornstein et al., "Synthesis of 6-Oxodecahydroisoquinoline-3-carboxylates. Useful Intermediates for the Preparation of Conformationally Defined Excitatory Amino Acid Antagonists", *J. Org. Chem.*, 56, 4388–4392 (1991).

Jacques et al., Enantiomers, Racemates, and Resolutions, 253–259, John Wiley and Sons, N.Y., (1981).

Ornstein et al., "6-Substituted Decahydroisoquinoline-3-carboxylic Acids as Potent and Selective Conformationally Constrained NMDA Receptor Antagonists", *J. Med. Chem.*, 35, 3547–3560 (1992).

*Primary Examiner*—Zinna Northington Davis
*Attorney, Agent, or Firm*—Martin A. Hay; James P. Leeds

[57] ABSTRACT

This invention provides novel decahydroisoquinoline compounds which are useful as excitatory amino acid receptor antagonists and in the treatment of neurological disorders. This invention also provides synthetic methods for preparing decahydroisoquinolines, as well as, novel intermediates in the synthesis thereof.

6 Claims, No Drawings

PROCESS OF PREPARING ISOQUINOLINE COMPOUNDS

This application is a division of application Ser. No. 08/111,747, filed Aug. 25, 1993, now U.S. Pat. No. 5,399,696 which is a division of application Ser. No. 07/939,780 filed on Sep. 3, 1992, now U.S. Pat. No. 5,284,957.

BACKGROUND OF THE INVENTION

The role of excitatory amino acids, such as glutamic acid and aspartic acid, as the predominant mediators of excitatory synaptic transmission in the central nervous system has been well established. Watkins & Evans, *Ann. Rev. Pharmacol. Toxicol.*, 21, 165 (1981); Monaghan, Bridges, and Cotman, *Ann. Rev. Pharmacol. Toxicol.*, 29, 365 (1989); Watkins, Krogsgaard-Larsen, and Honore, *Trans. Pharm. Sci.*, 11, 25 (1990). These amino acids function in synaptic transmission primarily through excitatory amino acid receptors. These amino acids also participate in a variety of other physiological processes such as motor control, respiration, cardiovascular regulation, sensory perception, and cognition.

Excitatory amino acid receptors are classified into two general types. Receptors that are directly coupled to the opening of cation channels in the cell membrane of the neurons are termed "ionotropic." This type of receptor has been subdivided into at least three subtypes, which are defined by the depolarizing actions of the selective antagonists N-methyl-D-aspartate (NMDA), α-amino-3-hydroxy-5-methylisoxazole-4-propionic acid (AMPA), and kainic acid (KA). The second general type is the G-protein or second messenger-linked "metabotropic" excitatory amino acid receptor. This second type, when activated by the agonists quisqualate, ibotenate, or trans-1-aminocyclopentane-1,3-dicarboxylic acid, leads to enhanced phosphoinositide hydrolysis in the postsynaptic cell. Both types of receptors appear not only to mediate normal synaptic transmission along excitatory pathways, but also participate in the modification of synaptic connections during development and changes in the efficiency of synaptic transmission throughout life. Schoepp, Bockaert, and Sladeczek, *Trends in Pharmacol. Sci.*, 11, 508 (1990); McDonald and Johnson, *Brain Research Reviews*, 15, 41 (1990).

The excessive or inappropriate stimulation of excitatory amino acid receptors leads to neuronal cell damage or loss by way of a mechanism known as excitotoxicity. This process has been suggested to mediate neuronal degeneration in a variety of conditions. The medical consequences of such neuronal degeneration makes the abatement of these degenerative neurological processes an important therapeutic goal.

Excitatory amino acid excitotoxicity has been implicated in the pathophysiology of a number of neurological disorders. This excitotoxicity has been implicated in the pathophysiology of acute and chronic neurodegenerative conditions including cerebral deficits subsequent to cardiac bypass surgery and grafting, stroke, cerebral ischemia, spinal cord trauma, head trauma, Alzheimer's Disease, Huntington's Chorea, amyotrophic lateral sclerosis, AIDS-induced dementia, perinatal hypoxia, cardiac arrest, hypoglyemic neuronal damage, ocular damage and retinopathy, and idiopathic and drug-induced Parkinson's Disease. Other neurological conditions, that are caused by glutamate dysfunction, require neuromodulation. These other neurological conditions include muscular spasms, migraine headaches, urinary incontinence, psychosis, opiate tolerance and withdrawal, anxiety, emesis, brain edema, chronic pain, convulsions, and tardive dyskinesia. The use of a neuroprotective agent, such as an AMPA receptor antagonist, is believed to be useful in treating these disorders and/or reducing the amount of neurological damage associated with these disorders. The EAA antagonists are also useful as analgesic agents.

Recent studies have shown that AMPA receptor antagonists are neuroprotective in focal and global ischemia models. The competitive AMPA receptor antagonist NBQX (2,3-dihydroxy-6-nitro-7-sulfamoylbenzo[f]quinoxaline) has been reported effective in preventing global and focal. ischemic damage. Sheardown et al., *Science*, 247, 571 (1900); Buchan et al., *Neuroreport*, 2, 473 (1991); LePeillet et al., *Brain Research*, 571, 115 (1992). The noncompetitive AMPA receptor antagonists GKYI 52466 has been shown to be an effective neuroprotective agent in rat global ischemia models. LaPeillet et al., *Brain Research*, 571, 115 (1992). These studies strongly suggest that the delayed neuronal degeneration in brain ischemia involves glutamate excitotoxicity mediated at least in part by AMPA receptor activation. Thus, AMPA receptor antagonists may prove useful as neuroprotective agents and improve the neurological outcome of cerebral ischemia in humans.

SUMMARY OF THE INVENTION

The present invention provides compounds which are antagonists of the excitatory amino acid receptors. More specifically, the present invention relates to compounds that are selective for the AMPA receptors. The present invention relates to a compound of the formula

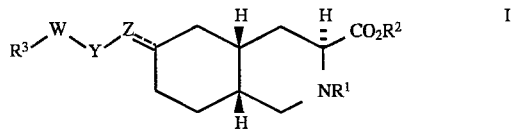

wherein:

$R^1$ is hydrogen, $C_1$-$C_{10}$ alkyl, arylalkyl, alkoxycarbonyl, or acyl;

$R^2$ is hydrogen, $C_1$-$C_6$ alkyl, substituted alkyl, cycloalkyl, or arylalkyl;

$R^3$ is $CO_2H$, $SO_3H$, $CONHSO_2R^8$, or a group of formula

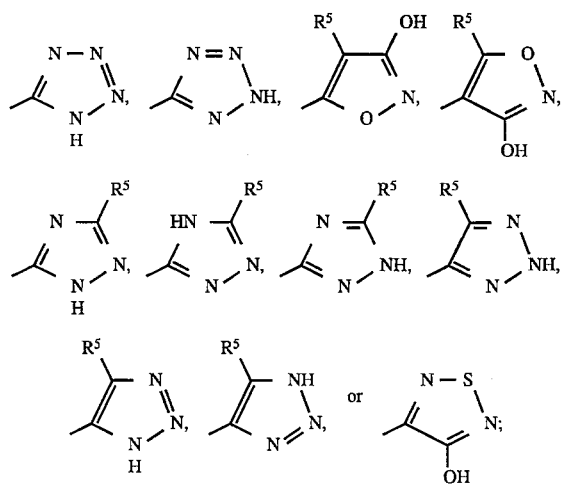

W is $(CH_2)_n$, S, SO, $SO_2$;

Y is $CHR^7$, $NR^4$, O, S, SO, or $SO_2$;

Z is $NR^6$, $CHR^7$, or CH; or

W and Y together are HC=CH or C≡C, or Y and Z together are HC=CH or C≡C;

$R^4$ is hydrogen, $C_1$-$C_4$ alkyl, phenyl, or acyl;

$R^5$ is hydrogen, $C_1$-$C_4$ alkyl, $CF_3$, phenyl, hydroxy, amino, bromo, iodo, or chloro;

$R^6$ is acyl;

$R^7$ is independently hydrogen, $C_1$-$C_4$ alkyl, phenyl, or substituted phenyl;

$R^8$ is $C_1$-$C_4$ alkyl or tetrazole-5-yl; and n is 0, 1, or 2;

provided that when Y is $NR^4$, O, S, SO, or $SO_2$, W is $(CH_2)_n$ and Z is $CHR^7$ or CH;

further provided that when W is S, SO, or $SO_2$, Y is $CHR^7$, Z is $CHR^7$ or CH, or Y and Z together are HC=CH or C≡C;

further provided that when W and Z are $CH_2$, Y is not S;

further provided that when W and Y together are HC=CH or C≡C, Z is $CHR^7$;

or a pharmaceutically acceptable salt thereof.

The invention also provides pharmaceutical formulations comprising a compound of formula I and a pharmaceutically-acceptable carrier, diluent, or excipient.

Further embodiments of the invention include a method of blocking the AMPA excitatory amino acid receptor, as well as methods of treating a neurological disorder which has been linked to the excitatory amino acid receptors, which comprises administering a compound of formula I. Examples of such neurological disorders which are treated with a formula I compound include cerebral deficits subsequent to cardiac bypass surgery and grafting, stroke, cerebral ischemia, spinal cord trauma, head trauma, Alzheimer's Disease, Huntington's Chorea, amyotrophic lateral sclerosis, AIDS-induced dementia, muscular spasms, migraine headaches, urinary incontinence, psychosis, convulsions, perinatal hypoxia, cardiac arrest, hypoglycemic neuronal damage, opiate tolerance and withdrawal, ocular damage and retinopathy, idiopathic and drug-induced Parkinson's Disease, anxiety, emesis, brain edema, chronic pain, or tardive dyskinesia. The formula I compounds are also useful as analgesic agents.

This invention also provides compounds which are useful in the preparation of the AMPA receptor antagonists. A second aspect of the present invention relates to a compound of the formula:

II wherein:

$R^9$ is acyl or alkoxycarbonyl;

$R^{10}$ is hydrogen, $C_1$-$C_6$ alkyl, or aryl;

U is hydroxyl, hydroxymethyl, formyl, bromomethyl, bromoethyl, or hydroxyethyl;

V is hydrogen; or

U and V together are methylene or methoxymethylene.

The present invention also provides processes for the preparation of compounds of formula VIIIb VIIIb wherein:

$R^9$ is acyl or alkoxycarbonyl;

$R^{10}$ is a chiral ammonium group, hydrogen, $C_1$-$C_6$ alkyl, or aryl.

A fourth aspect of the present invention is a process for preparing a compound of the formula wherein:

$R^9$ is acyl or alkoxycarbonyl;

$R^{10}$ is hydrogen, $C_1$-$C_6$ alkyl, or acyl.

Another aspect of the present invention is a process for preparing a compound of the formula wherein:

$R^9$ is acyl or alkoxycarbonyl;

$R^{10}$ is hydrogen, $C_1$-$C_6$ alkyl, or acyl.

Another aspect of the present invention is a process for preparing a compound of formula:

wherein:

J is a group of the formula

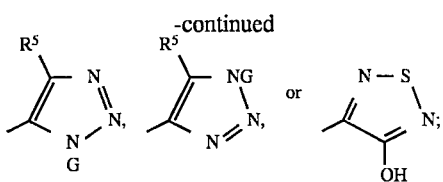

G is a nitrogen protecting group or hydrogen;
R⁵ is as defined previously;
R⁹ is acyl or alkoxycarbonyl; and
R¹⁰ is $C_1$–$C_6$ alkyl or aryl.

This invention also provides compounds which are useful in the preparation of a number of the AMPA receptor antagonists. Another aspect of the present invention relates to a compound of the formula:

wherein:
J is a group of the formula

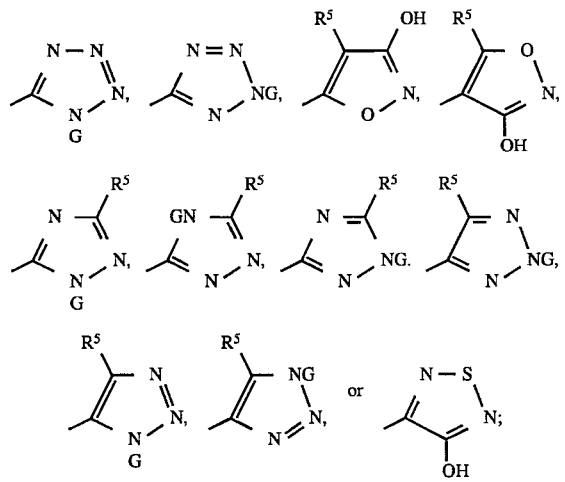

Q is $CHR^7P^+(Ph)_3X^-$, $CHR^7PO(Ph)_2$, $CR^7MSiR'_3$, $CH(SiR'_3)PO(OR')_2$, or $CH_2SnR'_3$;
R' is $C_1$–$C_6$ alkyl or phenyl;
R⁵ and R⁷ are as defined previously; and
G is a nitrogen protecting group or hydrogen;
M is Li⁺ or Mg⁺²X⁻; and
X⁻ is bromide, chloride, iodide, tetrafluoroborate, or hexafluorophosphate.

DETAILED DESCRIPTION OF THE INVENTION

In the above formula, the term "$C_1$–$C_{10}$ alkyl" represents a straight or branched alkyl chain having from one to ten carbon atoms. Typical $C_1$–$C_{10}$ alkyl groups include methyl, ethyl, n-propyl, isopropyl, n-butyl, isobutyl, sec-butyl, t-butyl, n-pentyl, isopentyl, n-hexyl, 2-methylpentyl, n-octyl, decyl, and the like. The term "$C_1$–$C_{10}$ alkyl" includes within it the terms "$C_1$–$C_6$ alkyl" and "$C_1$–$C_4$ alkyl". Typical $C_1$–$C_6$ alkyl groups include methyl, ethyl, n-propyl, isopropyl, n-butyl, isobutyl, sec-butyl, t-butyl, n-pentyl, isopentyl, and n-hexyl. Typical $C_1$–$C_4$ alkyl groups include methyl, ethyl, n-propyl, isopropyl, n-butyl, isobutyl, sec-butyl, and t-butyl.

The term "acyl" represents a hydrogen or $C_1$–$C_6$ alkyl group attached to a carbonyl group. Typical acyl groups include formyl, acetyl, propionyl, butyryl, valeryl, and caproyl.

The term "substituted alkyl," as used herein, represents a $C_1$–$C_6$ alkyl group that is substituted by one or more of the following: hydroxy, fluoro, chloro, bromo, and iodo. Examples of a substituted alkyl group include hydroxymethyl, chloromethyl, bromomethyl, iodomethyl, trichloromethyl, trifluoromethyl, chloroethyl, bromoethyl, perfluoroethyl, and the like.

The term "$C_1$–$C_4$ alkoxy" represents groups such as methoxy, ethoxy, n-propoxy, isopropoxy, n-butoxy, t-butoxy, and like groups. The term "halogen" refers to the fluoro, chloro, bromo, or iodo groups.

The term "substituted phenyl," as used herein, represents a phenyl group substituted with one or two moieties chosen from the group consisting of halogen, hydroxy, cyano, nitro, $C_1$–$C_6$ alkyl, $C_1$–$C_4$ alkoxy, alkoxycarbonyl, protected carboxy, carboxymethyl, hydroxymethyl, amino, aminomethyl, or trifluoromethyl. Examples of a substituted phenyl group include 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl, 4-hydroxyphenyl, 3-hydroxyphenyl, 2,4-dihydroxyphenyl, 3-nitrophenyl, 4-nitrophenyl, 4-cyanophenyl, 4-methylphenyl, 4-diphenylmethyl, 4-ethylphenyl, 4-methoxyphenyl, 4-carboxyphenyl, 4-(hydroxymethyl)phenyl, 4-aminophenyl, and the like.

The term "aryl" represents groups such as phenyl and substituted phenyl as described above. The term "arylalkyl" represents a $C_1$–$C_4$ alkyl group bearing an aryl group. Representatives of this latter group include benzyl, 1-phenylethyl, 2-phenylethyl, 3-phenylpropyl, 4-phenylbutyl, 2-methyl-2-phenylpropyl, (4-chlorophenyl)methyl, (2,6-dichlorophenyl)methyl, (4-hydroxyphenyl)methyl, (2,4-dinitrophenyl)methyl, and the like.

The term "cycloalkyl" represents a $C_3$–$C_7$ cyclic alkyl group such as cyclopropyl, cyclobutyl, cyclopentyl, cyclohexyl, and the like.

The term "alkoxycarbonyl" means a carboxyl group having a $C_1$–$C_6$ alkyl group attached to the carbonyl carbon through an oxygen atom. Representatives of this group include t-butoxycarbonyl and methoxycarbonyl.

The term "aryloxycarbonyl" represents a carboxyl group bearing an aryl group attached to the carbonyl carbon through an oxygen atom. Representatives of this group include phenoxycarbonyl, (4-chlorophenoxy)carbonyl, and (3-nitrophenoxy)carbonyl.

The term "chiral ammonium group" represents an amine having a chiral group, said amine forming the addition salt with the carboxylic acid group on the carbon atom adjacent to the nitrogen of the decahydroisoquinoline ring (C-3). Examples of amines having a chiral group that may react with the C-3 carboxylic acid group to form a chiral ammonium addition salt include R-(+)-α-methylbenzylamine, S-(–)-α-methylbenzylamine, (–)-α-(2-naphthyl)ethylamine, yohimbine, (+)-amphetamine, (–)-ephedrine, strychnine, brucine, quinine, quinidine, cinchonine, cinchonidine, and the like.

The term "nitrogen protecting group" includes trityl, benzyl, t-butyl, t-butyldimethylsilyl, and triphenylsilyl.

While all the formula I compounds of the present invention are believed to be antagonists of the AMPA excitatory amino acid receptor, certain compounds of the invention are preferred for such use. Preferably, $R^1$ is hydrogen or alkoxycarbonyl; $R^2$ is hydrogen or $C_1$–$C_6$ alkyl; $R^3$ is a group selected from the group consisting of $CO_2H$, $SO_3H$, $CONHSO_2R^8$,

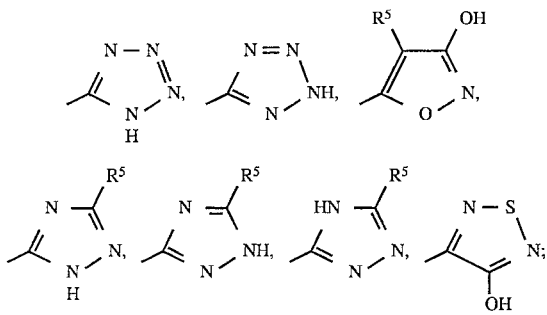

W is S or $(CH_2)_n$, where n=0, 1, or 2; Y is $CHR^7$, S, $SO_2$, or O; Z is $CHR^7$ or $NR^6$; Y and Z together are HC=CH; $R^5$ is hydrogen, $C_1$–$C_4$ alkyl, $CF_3$, or phenyl; $R^6$ is formyl; $R^7$ is hydrogen, $C_1$–$C_4$ alkyl, or phenyl; and $R^8$ is $C_1$–$C_4$ alkyl or tetrazole-5-yl. Representative compounds from this preferred group of compounds include: 6-[2-(1(2)H-tetrazole-5-yl)ethyl]decahydroisoquinoline-3-carboxylic acid, 6-[N-(1(2)H-tetrazole-5-yl)methylformamido] decahydroisoquinoline-3-carboxylic acid, 6-[2-(1(2)H-tetrazole-5-yl)-2-thiaethyl]decahydroisoquinoline-3-carboxylic acid, 6-[(1(2)H-tetrazole-5-yl)prop-1-yl]decahydroisoquinoline-3-carboxylic acid, 6-[(1(2)H-tetrazole-5-yl)methoxymethyl]decahydroisoquinoline-3-carboxylic acid, 6-[3-(1(2)H-tetrazole-5-yl)-3-thiaprop-1-yl]decahydroisoquinoline-3-carboxylic acid, 6-[(1(2)H-tetrazole-5-yl)but-1-yl]decahydroisoquinoline-3-carboxylic acid, 6-(2-carboxyethyl)decahydroisoquinoline-3-carboxylic acid, 6-(2-sulfoethyl)decahydroisoquinoline-3-carboxylic acid, 6-[2-(3-hydroxyisoxazole-5-yl)ethyl]decahydroisoquinoline-3-carboxylic acid, 6-[2-(1(2-4)H-1,2,4-triazole-5-yl)-2-thiaethyl]decahydroisoquinoline-3-carboxylic acid, 6-[(1(2-4)H-1,2,4-triazole-5-yl)sulfonylmethyl]decahydroisoquinoline-3-carboxylic acid, 6-[2-((N-methanesulfonyl)carboxamido)ethyl] decahydroisoquinoline-3-carboxylic acid, 6-[2-(N-(1(2)H-tetrazole-5-yl)carboxamido)ethyl]decahydroisoquinoline-3-carboxylic acid, 6-[2-(1(2)H-tetrazole-5-yl)-1-methylethyl] decahydroisoquinoline-3-carboxylic acid, 6-[2-(1(2)H-tetrazole-5-yl)-1-phenylethyl]decahydroisoquinoline-3-carboxylic acid, 6-[2-(3-hydroxy-1,2,5-thiadiazole-4-yl)ethenyl]decahydroisoquinoline-3-carboxylic acid, and the like.

Certain compounds of the present invention are more preferred for use as antagonists of the AMPA excitatory amino acid receptor. More preferably, $R^1$ is hydrogen or alkoxycarbonyl; $R^2$ is hydrogen or $C_1$–$C_6$ alkyl; $R^3$ is a group selected from $SO_3H$ and a group of the formula:

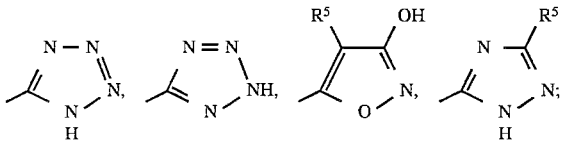

W is S, $SO_2$, or $(CH_2)_n$; n is 0, 1, or 2; Y is $CHR^7$, S, or $SO_2$; Z is $CHR^7$; $R^5$ is hydrogen, $C_1$–$C_4$ alkyl, or $CF_3$; and $R^7$ is hydrogen, $C_1$–$C_4$ alkyl, or phenyl. Representative compounds from this more preferred group of compounds include: 6-[2-(1(2)H-tetrazole-5-yl)ethyl] decahydroisoquinoline-3-carboxylic acid, 6-[2-(1(2)H-tetrazole-5-yl)-2-thiaethyl]decahydroisoquinoline-3-carboxylic acid, 6-[(1(2)H-tetrazole-5-yl)prop-1-yl] decahydroisoquinoline-3-carboxylic acid, 6-[(1(2)H-tetrazole-5-yl)methoxymethyl]decahydroisoquinoline-3-carboxylic acid, 6-[3-(1(2)H-tetrazole-5-yl)-3-thiaprop-1-yl]decahydroisoquinoline-3-carboxylic acid, 6-[(1(2)H-tetrazole-5-yl)but-1-yl]decahydroisoquinoline-3-carboxylic acid, 6-(2-sulfoethyl)decahydroisoquinoline-3-carboxylic acid, 6-(2-(3-hydroxyisoxazole-5-yl)ethyl] decahydroisoquinoline-3-carboxylic acid, 6-[(1(2-4)H-1,2,4-triazole-5-yl)sulfonylmethyl]decahydroisoquinoline-3-carboxylic acid, 6-[2-(1(2)H-tetrazole-5-yl)-1-methylethyl] decahydroisoquinoline-3-carboxylic acid, 6-[2-(1(2)H-tetrazole-5-yl)-1-phenylethyl]decahydro-isoquinoline-3-carboxylic acid, and the like.

Certain compounds of the invention are most preferred for use as antagonists of the AMPA excitatory amino acid receptor. Most preferably, $R^1$ and $R^2$ are hydrogen; $R^3$ is a group selected from a group of the formula

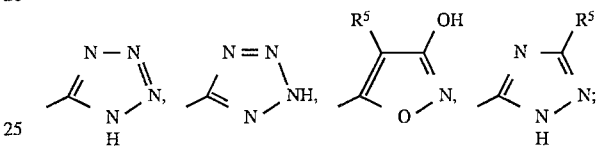

W is $(CH_2)_n$, where n is 0; Y is $CHR^7$, S, or $SO_2$; Z is $CHR^7$; $R^5$ is hydrogen or $C_1$–$C_4$ alkyl; and $R^7$ is hydrogen, $C_1$–$C_4$ alkyl, or phenyl. Representative compounds from this most preferred group of compounds include: 6-[2-(1(2)H-tetrazole-5-yl)ethyl]decahydroisoquinoline-3-carboxylic acid, 6-[2-(1(2)H-tetrazole-5-yl)-2-thiaethyl] decahydroisoquinoline-3-carboxylic acid, 6-[2-(3-hydroxyisoxazole-5-yl)ethyl]decahydroisoquinoline-3-carboxylic acid, 6-[(1(2-4)H-1,2,4-triazole-5-yl)sulfonylmethyl]decahydroisoquinoline-3-carboxylic acid, 6-[2-(1(2)H-tetrazole-5-yl)-1-methylethyl] decahydroisoquinoline-3-carboxylic acid, 6-[2-(1(2)H-tetrazole-5-yl)-1-phenylethyl]decahydroisoquinoline-3-carboxylic acid, and the like.

The formula I compounds of the present invention are the compounds having the relative stereochemistry as shown below:

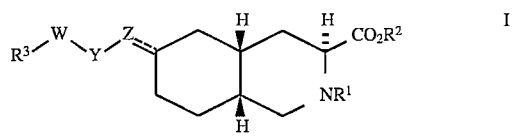

The compounds of the present invention, wherein Z is other than CH, possess at least four asymmetric carbon atoms. The asymmetric centers are the substituted carbon atom adjacent to the ring $NR^1$ group (3), the carbon atom where Z is attached to the ring (6), and the two bridgehead carbon atoms (4a and 8a). As such, the compounds can exist as diastereomers, each of which can exist as the racemic mixture of enantiomers. The compounds of the present invention include not only the racemates, but also the respective enantiomers. When Z is $NR^6$, the preferred configuration for the diastereomer is 3SR,4aSR,6SR,8aRS, and the preferred configuration for the enantiomer is 3S,4aS,6S, 8aR. When Z is $CHR^7$, the preferred configuration for the diastereomer is 3SR,4aRS,6SR,8aRS, except for the following: when $R^7$ is hydrogen, Y is $CH_2$, W is $(CH_2)_n$, and n=0, the preferred configuration for the diastereomer is 3SR, 4aRS,6RS,8aRS; when $R^7$ is hydrogen and Y and Z together are HC=CH, the preferred configuration for the diastereomer is 3SR,4aRS,6RS,8aRS; and when Y is S, SO, or SO₂, W is (CH₂)ₙ, and n=0, the preferred configuration for this diastereomer is 3SR,4aRS,6SR,8aRS. When Z is CHR⁷, the preferred configuration for the enantiomer is 3S,4aR,6S, 8aR, except for the following: when R⁷ is hydrogen, Y is CH₂, W is (CH₂)ₙ, and n=0, the preferred configuration for the enantiomer is 3S,4aR,6R,8aR; when R⁷ is hydrogen and Y and Z together are HC=CH, the preferred configuration for the enantiomer is 3S,4aR,6R,8aR; and when Y is S, SO, or SO₂, W is (CH₂)ₙ, and n=0, the preferred configuration for this enantiomer is 3S,4aR,6S,8aR. When Z is CH, the preferred configuration for the diastereomer is 3SR,4aRS, 8aRS, except when W is (CH₂)ₙ and n=0, the preferred configuration of the diastereomer 3SR,4aRS,8aRS. When Z is CH, the preferred configuration for the enantiomer is 3S,4aR,8aR, except when W is (CH₂)ₙ and n=0, the preferred configuration of the enantiomer 3S,4aR,8aR. When Z and Y together are HC=CH or C≡C, the preferred configuration for the diastereomer is 3SR,4aRS,6SR,8aRS; except when W is (CH₂)ₙ and n=0, the preferred configuration for the diastereomer is 3SR,4aRS,6SR,8aRS. When Z and Y together are HC=CH or C≡C, the preferred configuration for the enantiomer is 3S,4aR,6S,8aR; except when W is (CH₂)ₙ and n=0, the preferred configuration for the enantiomer is 3S,4aR,6S,8aR. The more preferred relative and absolute stereochemistry is shown in the following formula.

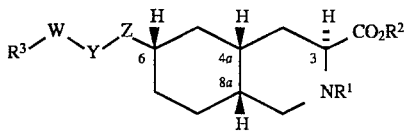

The compounds of the present invention may contain a tetrazole ring, which is known to exist as tautomeric structures. The tetrazole, having the double bond on the nitrogen atom at the 1-position and the hydrogen on the nitrogen atom at the 2-position is named as a 2H tetrazole and is represented by the following structure.

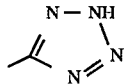

The corresponding tautomeric form wherein the hydrogen is at the nitrogen atom at the 1-position and the double bond on the nitrogen atom at the 4-position is named as a 1H-tetrazole. The 1H-tetrazole is represented by the following formula.

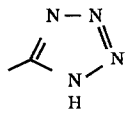

Mixtures of the two tautomers are referred to herein as 1(2)H-tetrazoles. The present invention contemplates both tautomeric forms as well as the combination of the two tautomers.

Similarly, the compounds of the present invention may contain a triazole ring. The triazoles exist in two positional isomeric forms, the 1,2,4-triazole and the 1,2,3-triazole. Each of these forms may exist as tautomeric structures. The triazole having the double bond on the nitrogen atom at the 1-position and the hydrogen on the nitrogen atom at the 2-position is named the 2H-triazole. The tautomeric form, wherein the hydrogen is on the nitrogen atom at the 1-position and the double bond on the nitrogen atom at the 2-position is named the 1H-triazole. The tautomeric form wherein the hydrogen is on the nitrogen atom at the 3-position or 4-position is named the positional 3H-triazole or 4H-triazole, respectively. Mixtures of the these tautomers are referred to herein as 1(2-4)H-triazoles. The present invention contemplates both positional isomers and individual tautomeric forms, as well as the combination thereof.

The present invention includes the pharmaceutically acceptable salts of the compounds defined by formula I. These salts can exist in conjunction with the acidic or basic portion of the molecule and can exist as acid addition, primary, secondary, tertiary, or quaternary ammonium, alkali metal, or alkaline earth metal salts. Generally, the acid addition salts are prepared by the reaction of an acid with a compound of formula I, wherein R¹ is hydrogen, C₁-C₁₀ alkyl, or arylalkyl. The alkali metal and alkaline earth metal salts are generally prepared by the reaction of the hydroxide form of the desired metal salt with a compound of formula I, wherein R² is hydrogen.

Acids commonly employed to form such salts include inorganic acids such as hydrochloric, hydrobromic, hydriodic, sulfuric, and phosphoric acid, as well as organic acids such as para-toluenesulfonic, methanesulfonic, oxalic, para-bromophenylsulfonic, carbonic, succinic, citric, benzoic, and acetic acid, and related inorganic and organic acids. Such pharmaceutically acceptable salts thus include sulfate, pyrosulfate, bisulfate, sulfite, bisulfite, phosphate, ammonium, monohydrogenphosphate, dihydrogenphosphate, meta-phosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, hippurate, maleate, butyne-1, 4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, α-hydroxybutyrate, glycolate, maleate, tartrate, methanesulfonate, propanesulfonate, naphthalene-1-sulfonate, napthalene-2-sulfonate, mandelate, ammonium, magnesium, tetramethylammonium, potassium, trimethylammonium, sodium, methylammonium, calcium, and the like salts.

While all the formula II compounds of the present invention are believed to be useful in the preparation of the AMPA receptor antagonists, certain compounds of the invention are preferred for such use. Preferably, R⁹ is alkoxycarbonyl; R¹⁰ is C₁-C₆ alkyl; U is hydroxyl, hydroxymethyl, hydroxyethyl, or formyl; V is hydrogen; or U and V together are methylene or methoxymethylene. More preferably, U is hydroxymethyl or formyl, or U and V together are methylene or methoxymethylene. Most preferably, R⁹ is methoxycarbonyl and R¹⁰ is ethyl. Representative compounds of this most preferred group include ethyl 6-methylidine-2-methoxycarbonyldecahydroisoquinoline-3-carboxylate, ethyl 2-methoxycarbonyl-6-(methoxymethylene) decahydroisoquinoline-3-carboxylate, ethyl 6-hydroxymethyl-2-methoxycarbonyldecahydroisocfuinoline-3-carboxylate, and ethyl 6-formyl-2-methoxycarbonyldecahydroisoquinoline-3-carboxylate.

The compounds of the general formula

wherein J and Q are as defined previously are useful for the synthesis of the formula I compounds wherein Z is CH or $CHR^7$ and Y is $CH_2$. Certain compounds of the invention are preferred for such use. Preferably, Q is a group of the formula $CH(SiR'_3)PO(OR')_2$, $CHR^7PO(Ph)_2$, or $CHR^7P^+(Ph)_3X^-$; $X^-$ is tetrafluoroborate, hexafluorophosphate, iodide, bromide, or chloride; $R^5$ is $C_1$–$C_4$ alkyl, $CF_3$, hydrogen, or phenyl; $R^7$ is hydrogen, $C_1$–$C_4$ alkyl, or phenyl; R' is $C_1$–$C_6$ alkyl or phenyl; G is hydrogen or trityl; and J is a group of the formula

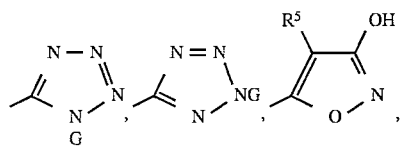

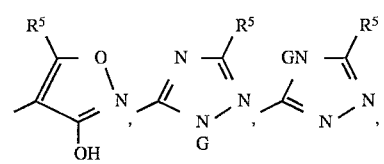

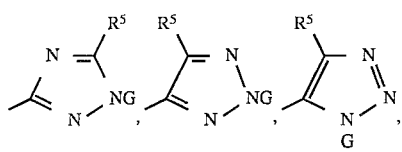

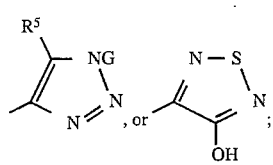

More preferably, Q is a group of formula $CHR^7PO(Ph)_2$ or $CHR^7P^+(Ph)_3X^-$; $X^-$ is iodide, chloride, or bromide; $R^5$ is hydrogen, methyl, or phenyl; $R^7$ is hydrogen, methyl, or phenyl; and J is a group of the formula

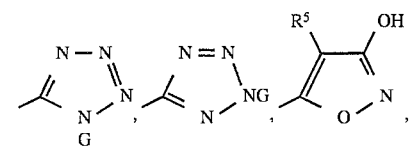

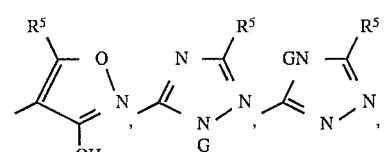

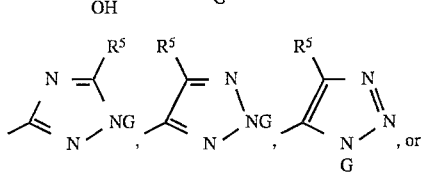

-continued

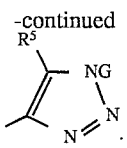

Most preferably, Q is $CHR^7P^+(Ph)_3X^-$; $X^-$ is bromide or chloride, $R^5$ is hydrogen; $R^7$ is hydrogen; and J is a group of the formula

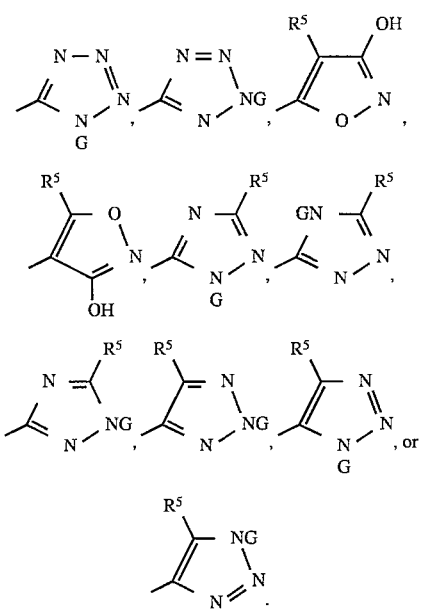

The formula I and formula II compounds of the present invention may be chemically synthesized from a common intermediate, 6-oxo-decahydroisoquinoline-3-carboxylate (VIII). A synthesis of this compound was described in U.S. Pat. No. 4,902,695, which is incorporated herein by reference. An improved synthesis of this intermediate from d,l-m-tyrosine is shown in Scheme I.

Scheme I

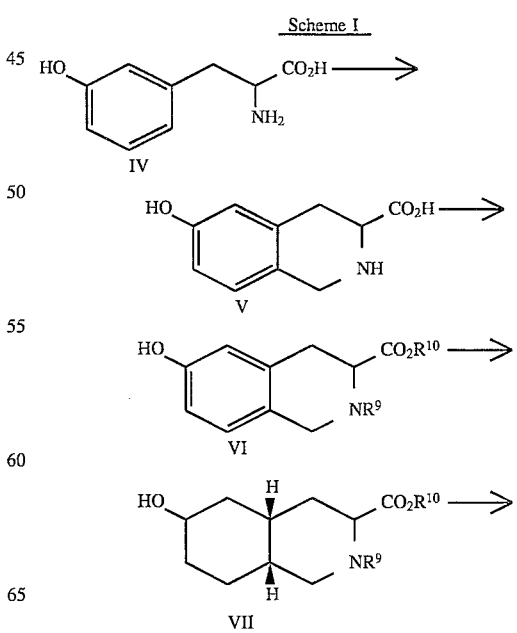

-continued
Scheme I

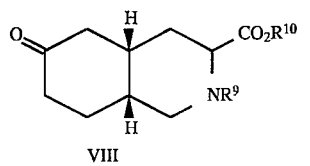

VIII

Generally, m-tyrosine (IV) is condensed with formaldehyde to form a 6-hydroxy substituted tetrahydroisoquinoline-3-carboxylic acid (V). This compound is esterified at the carboxyl group and blocked on the ring nitrogen with a suitable protecting group, to provide a doubly protected intermediate (VI). This intermediate is reduced to prepare the protected 6-hydroxydecahydroisoquinoline-3-carboxylate (VII). The 6-hydroxyl group is then oxidized to a 6-oxo group to give common intermediate VIII.

The present invention provides improved processes for the synthesis of intermediate VIII, wherein the ring juncture is cis. Meta-tyrosine, preferably racemic m-tyrosine, is condensed with formaldehyde to form the hydroxy substituted tetrahydro-isoquinoline-3-carboxylate (V). This reaction is preferably carried out in deionized water containing concentrated hydrochloric acid at a temperature of about 55° C. to about 70° C. for about 0.5 to about 2 hours. The formula V compound is preferably isolated by cooling the reaction mixture to a temperature of about 3° C. to about 10° C. and removing the product by filtration.

This compound is preferably protected on both the 3-carboxyl group and the ring nitrogen. Methods for the protection of amino groups and carboxyl groups are generally described in McOmie, *Protective Groups in Organic Chemistry*, Plenum Press, New York, 1973, and Greene and Wutz, *Protecting Groups in Organic Synthesis*, 2d. ed., John Wiley and Sons, New York, 1991. The carboxyl group may be protected as the $C_1$-$C_6$ alkyl, substituted alkyl, or aryl ester. The preferred ester is the $C_1$-$C_6$ alkyl ester; the ethyl ester is the most preferred. This ester is prepared by the reaction of intermediate V with a mixture of ethanol and concentrated sulfuric acid. The reaction is preferably carried out at the reflux temperature of the solvent for a period of about 16 hours. The ring nitrogen may be protected with an acyl or alkoxycarbonyl group. The preferred protecting groups are t-butoxycarbonyl and methoxycarbonyl. The most preferred protecting group is methoxycarbonyl.

The 2-methoxycarbonyl protecting group is added using standard synthetic organic techniques. The ethyl ester of intermediate V is reacted with methyl chloroformate in the presence of potassium carbonate to form intermediate VI. This reaction is preferably carried out at a temperature of about 1° C. to about 15° C. for a period of about 2 hours. Also, the reaction is preferably carried out by the subsequent addition of potassium carbonate and methyl chloroformate to the esterification reaction mixture. intermediate VI, wherein $R^9$ is methoxycarbonyl and $R^{10}$ is ethyl, is preferably isolated by extraction and crystallization (ethanol/water).

Intermediate VII is prepared by reduction of intermediate VI. The preferred method of reduction is catalytic hydrogenation. Suitable catalysts include palladium on carbon, platinum on carbon, palladium on alumina, platinum oxide, ruthenium on alumina, rhodium on alumina, or rhodium on carbon. The preferred catalysts are ruthenium on alumina, rhodium on alumina, or rhodium on carbon. The most preferred catalyst for this reduction is rhodium on carbon. Suitable solvents for the reaction include polar organic solvents, such as ethyl acetate, methanol, and ethanol. Ethyl acetate is the preferred solvent for the reaction. The reduction is carried out at a hydrogen pressure of about 100 psi to about 1000 psi and at a temperature of about 80° C. to about 150° C. When the reaction employs rhodium on alumina, the reaction is complete after about 24 hours. The catalyst may be removed by filtration and the protected 6-hydroxydecahydroisoquinoline-3-carboxylate used in the next step without isolation.

The 6-hydroxy group of intermediate VII is oxidized to a 6-oxo group in the preparation of intermediate VIII. This transformation is preferably accomplished by the use of a mild oxidizing agent. Suitable mild oxidizing agents include sodium hypochlorite, ruthenium trichloride/sodium periodate, and ruthenium trichloride/periodic acid. Other oxidizing agents, such as pyridinium chlorochromate (PCC), Jones' reagent, dimethylsulfoxide/N-chlorosuccinimide, tetrapropylammoniumperruthinate (TPAP), pyridine/$SO_3$, and hypochlorous acid, are also useful in effecting this transformation. Preferably, the filtered ethyl acetate solution containing intermediate VII is treated with ruthenium trichloride and water, and the resulting mixture cooled to a temperature of about –10° C. to about 25° C. The two-phase mixture is next treated with periodic acid. After the addition of periodic acid, the reaction mixture is allowed to warm to a temperature of about 20° C. to about 35° C. The desired product, intermediate VIII, is isolated using standard techniques.

Alternatively, intermediate VI is reduced to prepare intermediate VIII. The preferred method of reduction is catalytic hydrogenation. This reaction gives a mixture of 6-hydroxy intermediate VII and 6-keto intermediate VIII. Without further purification the mixture of these intermediates can be used in the next step to oxidize 6-hydroxy intermediate VII of the mixture to intermediate VIII without further purification. Suitable catalysts for this transformation include palladium on carbon and rhodium on carbon. The preferred catalyst is rhodium on carbon. Suitable solvents for this reaction include polar organic solvents, such as ethyl acetate, methanol, and ethanol. Ethyl acetate is a preferred solvent for the reaction. The reduction is carried out at a hydrogen pressure of about 30 psi to about 200 psi at a temperature of about 70° C. to about 90° C. The preferred conditions for this transformation are a hydrogen pressure of about 100 psi and a temperature of about 85° C. When the reaction employs rhodium on carbon, the reaction is complete after about 2 hours to about 24 hours. The catalyst may be removed by filtration and the products used in the next step without further isolation.

The synthetic scheme described in the preceding paragraphs produces a mixture of diastereomers, whose relative configurations are illustrated by VIIIa and VIIIb.

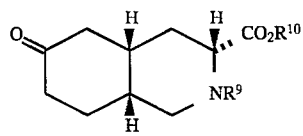
VIIIa

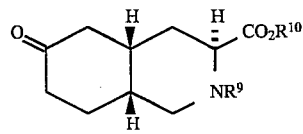
VIIIb

The predominant diastereomer from this scheme is intermediate VIIIa. This mixture of diastereomers may be equilibrated to a mixture where VIIIb is the predominant diastereomer by treatment with a strong base. Suitable strong bases for this equilibration include metal alkoxides, such as sodium ethoxide and potassium t-butoxide, and lithium diisopropylamide. The preferred strong base for the equilibration is sodium ethoxide. When a metal alkoxide is used as a base, the corresponding alcohol may be used as a solvent. The preferred solvent for the equilibration is ethanol. When sodium ethoxide and ethanol are used, the equilibration may be carried out at a temperature of about room temperature to about the reflux temperature of the solvent. Preferably, the equilibration, when carried out in NaOEt/EtOH, is carried out at about 40° C. This equilibration requires from about one to about six hours. The preferred diastereomer, intermediate VIIIb, is isolated by crystallization from ether ($R^9$ is methoxycarbonyl and $R^{10}$ is ethyl).

The enantiomers of each diastereomeric pair of intermediate VIII are resolved using standard resolution techniques. See Jacques, Collet, and Wilen, *Enantiomers, Racemates, and Resolutions,* John Wiley and Sons, New York, 1981. The preferred method for resolution of the diastereomers and enantiomers uses chiral amines to form the diastereomeric salts. Suitable chiral amines are described in Jacques et al., Chapter 5, pages 253–259, which is incorporated herein by reference. Examples of suitable chiral amines include R-(+)-α-methylbenzylamine, S-(–)-α-methylbenzylamine, (–)-α-(2-naphthyl)ethylamine, yohimbine, (+)-amphetamine, (–)-ephedrine, strychnine, brucine, quinine, quinidine, cinchonine, cinchonidine, and the like. The preferred chiral amines are α-methylbenzylamine, brucine, quinine, quinidine, cinchonine, cinchonidine. The more preferred chiral amines are α-methylbenzylamine, brucine, and quinine. The most preferred chiral amine for the resolution of VIIIb is α-methylbenzylamine.

The preferred method of resolving the preferred enantiomer is described in the following. The ethyl ester, intermediate VIIIb where $R^9$ is methoxycarbonyl and $R^{10}$ is ethyl, is hydrolyzed using 5N sodium hydroxide at a temperature of about 25° C. to about 40° C. for a period of about 0.5 to about 2 hours. Suitable solvents for this transformation include the alcohols, such as methanol and ethanol. The free acid may be isolated by extraction with ethyl acetate. The free acid, preferably in ethyl acetate solution, is treated with R-(+)-α-methylbenzylamine at a temperature of about 25° C. to about 35° C. for a period of about 15 to about 60 minutes. Intermediate (–)-VIIIb ($R^{10}$ is hydrogen) precipitates from the reaction solution as the R-(+)-α-methylbenzylamine salt. The material is further purified by reslurrying in warm (45°–50° C.) ethyl acetate. In a similar manner, (+)-VIIIb is prepared using S-(–)-α-methylbenzylamine. The relative and absolute stereochemistry of the structures of these intermediates is shown below. Intermediate (–)-VIIIb is the preferred enantiomer.

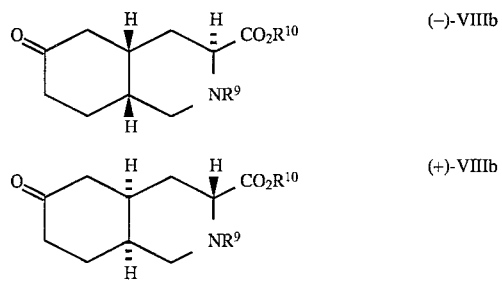

The resolved enantiomer is esterified on the 3-carboxyl group for further chemical modification. The preferred ester is the ethyl ester. Suitable esterification conditions include the reaction of intermediate VIII ($R^{10}$ is hydrogen) with an akylating reagent in the presence of a base. Suitable akylating reagents for the present transformation include ethyl iodide, ethyl bromide, ethyl chloride, and diethyl sulfate. The base is selected from the group consisting of triethylamine, N,N-diisopropylethylamine, pyridine, collidine, sodium bicarbonate, and sodium carbonate. Suitable solvents for the esterification are polar organic solvents, such as dimethylformamide and acetonitrile. This esterification is preferably carried out using ethyl bromide and triethylamine in acetonitrile at the reflux temperature of the solvent for a period of about one to two hours.

The compounds of the present invention are chemically synthesized from common intermediate VIII by a number of different routes. The specific synthetic steps of the routes described herein may be combined in other ways to prepare the formula I compounds. The following discussion is not intended to be limiting to the scope of the present invention, and should not be so construed. The synthesis of the formula I compounds, wherein Y is $CH_2$, Z is $CHR^7$, and W is $(CH_2)_n$ or S, and n=0, are prepared as shown in Scheme II.

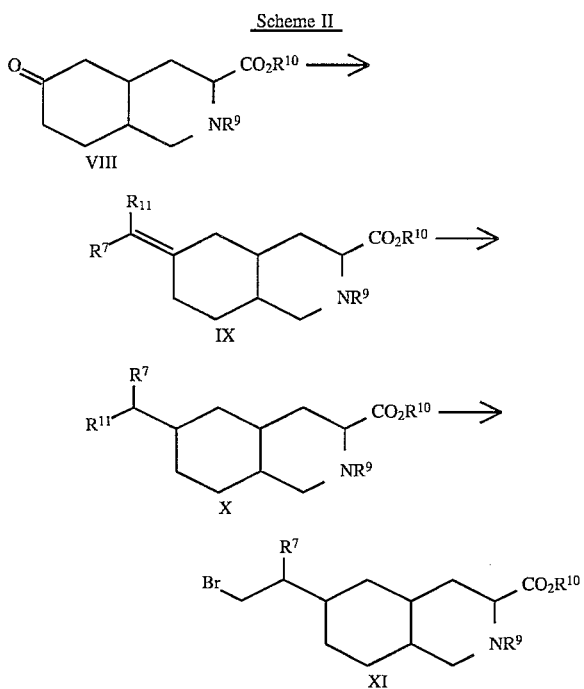

Generally, intermediate VIII is reacted with a Horner-Emmons reagent to form unsaturated intermediate IX, wherein $R^{11}$ is a protected carboxyl group. This compound is reduced to intermediate X. The carboxyl group is next reduced to a hydroxyl group, which is converted to bromo intermediate XI. Intermediate XI can be reacted with a number of nucleophilic species to give the formula I compounds wherein W is $(CH_2)_n$, n=0, and $R^3$ is $CO_2H$ or $SO_3H$, or wherein W is S and $R^3$ is a triazole or tetrazole.

More specifically intermediate VIII is reacted with a Horner-Emmons reagent of the general formula $(CH_3CH_2O)_2POCH(R^7)R^{11}$, wherein $R^7$ is hydrogen, $C_1$–$C_4$ alkyl, phenyl, or substituted phenyl, and $R^{11}$ is a protected carboxyl group. Suitable carboxyl protecting groups include ethyl and benzyl esters. This reaction is generally accomplished by treating the appropriate diethylphosphonate with a strong base, such as sodium hydride or sodium bis(trimethylsilyl)amide, to generate the sodium salt of the phosphonate which is then reacted in a polar organic solvent, such as dry tetrahydrofuran (THF), with VIII to provide intermediate IX. This reaction is generally carried out between 0° C. and the reflux temperature of the reaction mixture. When a slight molar excess of the phosphonate anion is employed, the reaction is generally complete after about six hours at room temperature.

Intermediate IX is then reduced to provide intermediate X. A preferred method of accomplishing this reduction is through hydrogenation, preferably in the presence of a catalyst. Suitable catalysts for this reduction include palladium on carbon and platinum on carbon. Suitable solvents for such reduction include polar organic solvents such as ethanol and ethyl acetate. The reduction is typically carried out at a hydrogen pressure of about 60 psi to about 100 psi. The reaction is generally complete after about four hours at room temperature.

Intermediate X is then used in the preparation of a compound of formula XI. This transformation is generally accomplished by reducing intermediate X, where $R^{11}$ is a carboxy or protected carboxyl group. The carboxyl group can be reduced to an alcohol by methods well known in the art. One suitable route is by the treatment of the carboxy compound with borane-methyl sulfide. This transformation is generally carried out in a polar organic solvent, such as tetrahydrofuran, at a temperature of about 0° C. The hydromy compound is then converted to a compound of formula XI by treating the hydroxy substituted compound with triphenylphosphine and bromine. This transformation is generally carried out in a polar organic solvent, such as methylene chloride, at a temperature of about 0° C.

Intermediate XI may be reacted with a number of nucleophilic reagents to produce the compounds of formula I. Examples of such nucleophilic species are thiocyanate, thiotriazole, and thiotetrazole. For example, the reaction of bromo intermediate XI with thiotetrazole in the presence of an amine base produces the formula I compounds where $R^3$ is tetrazole and W is S. Suitable amine bases for the reaction include triethylamine, N,N-diisopropylethylamine, N-methylmorpholine, pyridine, and collidine. This reaction is preferably carried out in a polar organic solvent, such as acetonitrile, at a temperature of about 50° C. to about 100° C. The product of this reaction is converted to the formula I compound, wherein $R^1$ and $R^2$ are hydrogen, by treatment with 6N hydrochloric acid which removes the amine and carboxy protecting groups.

Intermediate XI may also be reacted with sulfite ion. The reaction of bromo intermediate XI with sodium sulfite in an aqueous organic solvent mixture leads to the formation of the formula I compounds wherein $R^3$ is $SO_3H$. The reaction is generally carried out in an aqueous/organic solvent mixture, such as ethanol/water, at the reflux temperature of the solvent. The amino and carboxy protecting groups may be subsequently removed by treatment with 6N hydrochloric acid.

The formula I compounds wherein W is S are useful for the preparation of the formula I compounds wherein W is SO or $SO_2$. Generally, the formula I compound wherein W is S is treated with an oxidizing agent to prepare the corresponding compounds wherein W is SO or $SO_2$. A suitable oxidizing agent for this transformation is 3-chloroperoxybenzoic acid. The oxidation is generally carried out in a polar organic solvent, such as methylene chloride. The formula I compounds wherein W is SO are prepared by treating the corresponding formula I compound wherein W is S with the oxidizing agent at a temperature of about −78° C. to about −30° C. The reaction is generally complete after a period of about one to about 4 hours. The formula I compounds wherein W is $SO_2$ are prepared by treating the corresponding formula I compound where W is S or SO with the oxidizing agent at a temperature of about room temperature to about 50° C. Preferably, the oxidation is carried out at room temperature in methylene chloride with an excess of 3-chloroperoxybenzoic acid. The reaction is generally complete after a period of about eighteen hours.

A second group of the formula I compounds wherein $R^3$ is $CO_2H$ or $CONHSO_2R^8$, W is $(CH_2)_n$, n is 0, Y and Z are CH=CH, or Y and Z are $CH_2$, are prepared as outlined in Scheme III.

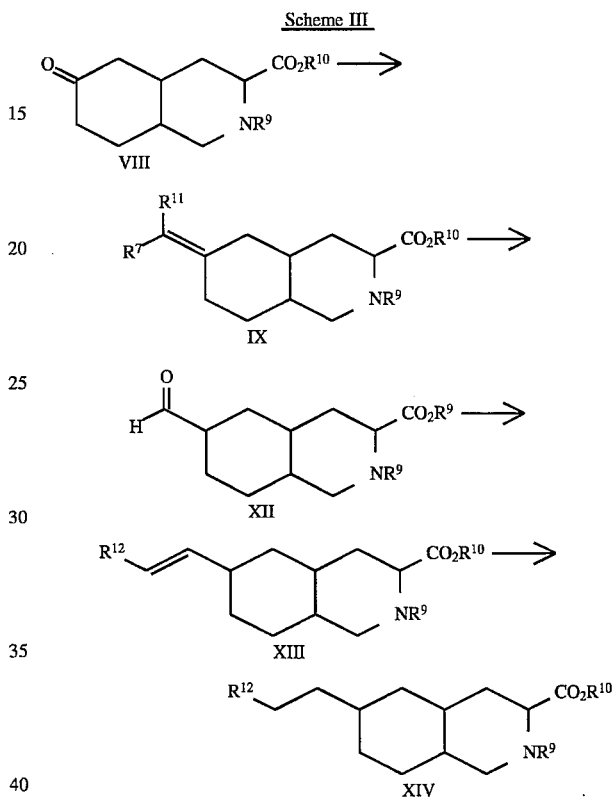

Generally, intermediate VIII is reacted with a Wittig reagent and the product hydrolyzed to form 6-formyl intermediate XII. This compound is reacted with a Horner-Emmons reagent to prepare unsaturated compound XIII. Intermediate XIII may be reduced and/or modified using standard chemical techniques.

More specifically, intermediate VIII is reacted with a wittig reagent of the formula $Ph_3PCHOCH_3$ to produce intermediate IX, wherein $R^7$ is hydrogen and $R^{11}$ is methoxy. This reaction is generally accomplished by treating methoxymethyltriphenylphosphonium chloride with a strong base, such as sodium bis(trimethylsilyl)amide, to generate the yield which is then reacted in a polar organic solvent, such as dry tetrahydrofuran, with intermediate VIII. This reaction is generally carried out at a temperature of about 0° C. to about 25° C. The reaction is generally complete after about thirty minutes at 0° C. Intermediate IX is then converted to the 6-formyl intermediate XII by treatment with aqueous acid. A suitable acid for this transformation is dilute hydrochloric acid, such as 1N hydrochloric acid. The reaction is generally carried out at room temperature for a period of about two to about eight hours.

Intermediate XII is then reacted with a Horner-Emmons reagent to prepare the compounds of formula XIII. This Horner-Emmons reagent has the general formula $(CH_3CH_2O)_2POCH_2R^{12}$, where $R^{12}$ is a protected carboxyl group, such as ethoxycarbonyl or benzyloxycarbonyl, cyano, tetrazole, triazole, or thiadiazole. The reaction is generally accomplished by treating the appropriate diethylphosphonate with a strong base, such as sodium hydride, to generate the sodium salt of the phosphonate which is then reacted in an organic solvent, such as dry tetrahydrofuran, to provide the compound formula XIII. This reaction is generally carried at a temperature between 0° C. and 25° C. The reaction is generally complete after about thirty minutes to about four hours at room temperature.

Intermediate XIII is then reduced to provide intermediate XIV. A preferred method for reduction of intermediate XIII is catalytic hydrogenation, preferably in the presence of palladium on carbon or platinum on carbon in inert solvent. Suitable inert solvents include ethanol and ethyl acetate. When the carboxyl protecting group is a benzyl group, this group is removed in the catalytic hydrogenation. Intermediate XIV can then be transformed into a compound of formula I, wherein $R^1$ and $R^2$ are hydrogen, by deprotection of the acid and nitrogen functionalities. This is generally carried out by treating intermediate XIV with 6N hydrochloric acid. The preferred method is to heat the intermediate compound in 6N hydrochloric acid at reflux for a period of about eighteen hours.

Intermediate XIV, wherein $R^{12}$ is a protected carboxyl group, can be used to prepare the formula I compounds wherein $R^3$ is $CONHSO_2R^8$. The reaction of carboxy intermediate XIV and carbonyl diimidazole followed by addition of a substituted amine produces the corresponding substituted amide. The reaction of carboxy intermediate XIV and 1,1'-carbonyldiimidazole is preferably carried out in an anhydrous organic solvent, such as dry tetrahydrofuran, at the reflux temperature of the solvent. The product of this reaction is then treated with a substituted amine in the presence of a base. One example of a suitable substituted amine is methansulfonamide. Suitable bases for this reaction include N,N-diisopropylethylamine, collidine, and 1,8-diazabicyclo[5.4.0]-undec-7-ene. This reaction is preferably carried out at room temperature for a period of about six to about twenty hours. The protecting group on the 3-carboxyl group is then removed by treatment of the amide intermediate XIV with 1N sodium hydroxide. This transformation is carried out at room temperature for a period of about eighteen hours. The protecting group on the ring nitrogen is removed by treating the amide intermediate with iodotrimethylsilane in a polar organic solvent, such as chloroform. This method of deprotection is preferred over the use of 6N hydrochloric acid, to retain the amide group.

Carboxy intermediate XIV can also be used to prepare additional compounds of the present invention, for example the formula I compounds wherein $R^3$ is $CO_2H$, $CONHSO_2R^8$, or tetrazola, W is $(CH_2)_n$, n is 2, and Y and Z are $CH_2$, as outlined in Scheme IV.

Scheme IV

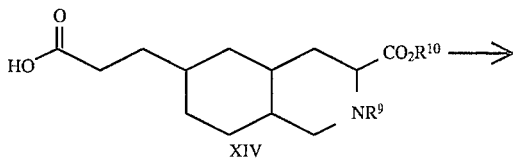

XIV

-continued
Scheme IV

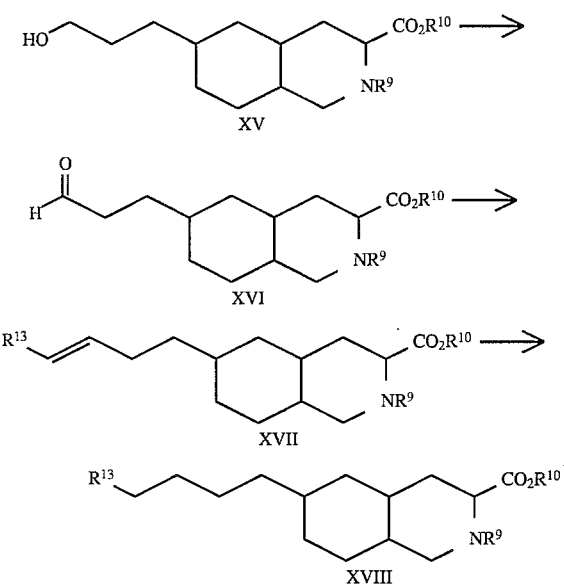

Generally, carboxy intermediate XIV is converted to aldehyde intermediate XVI. This compound is reacted with a Horner-Emmons reagent to produce unsaturated intermediate XVII. This compound may be reduced to produce compound XVIII.

More particularly, the carboxy intermediate is reduced to hydroxy intermediate XV with a suitable reducing agent, such as borane-methyl sulfide. This reaction is preferably carried out in a polar organic solvent, such as tetrahydrofuran, at a temperature of about 0° C. to about 25° C.

The hydroxy intermediate is then converted to aldehyde intermediate XVI. The hydroxyl group is oxidized to the aldehyde with reagents which are well known in the chemical arts. One such reagent is a combination of oxalyl chloride and dimethylsulfoxide. Generally, dimethylsulfoxide (DMSO) and oxalyl chloride are combined in an organic solvent, such as methylene chloride, at about −78° C. to form the oxidizing agent. After about five to about fifteen minutes, a solution of the alcohol is added to the cold oxidizing agent solution. This mixture is then treated with an amine base, such as triethylamine, and allowed to warm to room temperature.

The aldehyde intermediate XVI is then reacted with a Horner-Emmons reagent of the general formula $(CH_3CH_2O)_2POCH_2R^{13}$, wherein $R^{13}$ is a protected carboxyl group or cyano. This reaction is generally accomplished by treating the appropriate diethylphosphonate with a strong base, such as sodium hydride, to generate the sodium salt of the phosphonate which is then reacted in an organic solvent such as dry tetrahydrofuran, with intermediate XVI to provide intermediate XVII. This reaction is generally carried out at a temperature of 0° C. to about 25° C. for a period of about thirty minutes to about two hours.

Intermediate XVII is then reduced to provide the corresponding saturated analog intermediate XVIII. The method of accomplishing this reduction is through catalytic hydrogenation, preferably in the presence of palladium on carbon or platinum on carbon. A second method of accomplishing this transformation is a dissolving metal reduction. A suitable metal for use in this transformation is magnesium in a polar organic solvent, such as methanol.

Cyano intermediate XVIII, wherein $R^{13}$ is —CN, can be converted to a tetrazole intermediate. The cyano intermediate is reacted with tributyltin azide at a temperature of about 50° C. to about 120° C., preferably at a temperature of about 80° C. The produce may be isolated, but is preferably hydrolyzed directly to a compound of formula I, wherein $R^1$ and $R^2$ are hydrogen. The hydrolysis is conducted in 6N hydrochloric acid at a temperature of about 100° C. for a period of about two to about twenty-four hours, to produce a compound of formula I wherein $R^3$ is tetrazole. This procedure for the formation of tetrazole from nitriles is also suitable for the conversion of a thiocyanate to a thiotetrazole compound.

The formula I compounds wherein Y and Z together are C≡C are prepared as shown in Scheme V.

Scheme V

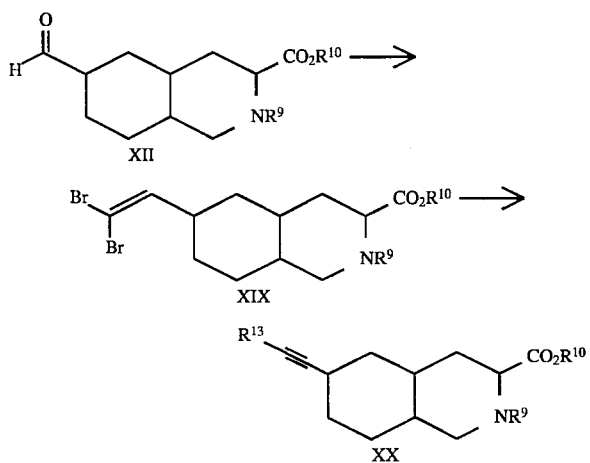

Generally, 6-formyl intermediate XII is converted to dibromoolefin intermediate XIX and then to ethynyl intermediate XX according to the procedure described by Corey and Fuchs. Corey and Fuchs, *Tetra. Lett.*, 36, 3769–3772 (1972). The ethynyl intermediate is modified using standard techniques and as described herein to prepare the formula I compounds.

More specifically, 6-formyl intermediate XII is treated with a mixture of triphenylphosphine and carbontetrabromide to produce dibromoolefin intermediate XIX. The reaction is generally carried out in methylene chloride at a temperature of about 0° C. for a period of about five minutes to about one hour. Alternatively, a mixture of zinc dust, triphenylphosphine, and carbontetrabromide in methylene chloride is allowed to react at room temperature for a period of about 24 to about 30 hours, and then treated with the 6-formyl intermediate. This second reaction is carried out in methylene chloride at a temperature of about 20° C. to about 30° C. for a period of about one to about two hours.

Dibromoolefin intermediate XIX is then converted to ethynyl intermediate XX. Treatment of the dibromoolefin intermediate with about two equivalents of n-butyllithium produces the lithium acetylide XX, wherein $R^{13}$ is Li. This transformation is typically carried out in a polar organic solvent, such as tetrahydrofuran, at a temperature of about −78° C. to about 25° C. The lithium acetylide is reacted with electrophiles, such as methoxymethyl chloride, 5-bromomethyl-3-methoxyisoxazole, 3-diphenylmethoxy-4-iodomethyl-1,2,5-thiadiazole, carbon dioxide, tetrazole disulfide, and the like, to prepare the formula I compounds. In a typical example, the lithium acetylide is treated with solid $CO_2$ at a temperature of about −78° C. to about −60° C. to produce propargylic acid intermediate XX wherein $R^{13}$ is $CO_2H$. This compound may be further modified as described herein.

Alternatively, propargylic acid intermediate XX may be converted to ethynyl tetrazole intermediate XX, wherein $R^{13}$ is a tetrazole group. For this conversion, the carboxyl group is converted to a carboxamide by treatment with a chloroformate and an amine base followed by treatment with ammonia. Typical chloroformates include methyl chloroformate, ethylchloroformate, butylchloroformate, and the like. Suitable amine bases for the conversion include triethylamine, N,N-diisopropylethylamine, N-methylmorpholine, and the like. The reaction is generally carried out at a temperature from about −10° C. to about 25° C., preferably at 0° C.

The ethynyl carboxamide intermediate may be converted to an ethynyl nitrile, wherein $R^{13}$ is CN. Standard chemical techniques for the dehydration of carboxamides to nitriles are described in March and Larock. March, *Advanced Organic Chemistry. Reactions, Mechanism, and Structure*, 932–933 (3d ed., 1985); *Compendium of Organic Synthetic Methods;* Larock, *Comprehensive Organic Transformations* (1989). In a typical example, the carboxamide is dehydrated by treatment with phenylphosphonic dichloride in pyridine/methylene chloride at a temperature of about 0° C. The nitrile intermediate is converted to the tetrazole by treatment with tributyltin azide as described herein.

The formula I compounds wherein W and Y together are C≡C are prepared in a similar manner to that described above. Generally, intermediate X, where $R^{11}$ is hydroxy, is oxidized to the aldehyde intermediate, $R^{11}$ is formyl, using procedures similar to those described previously. This aldehyde is then converted to a dibromoolefin and lithium acetylide as described above.

The formula I compounds wherein Z is $NR^6$ are prepared as outlined in Scheme VI.

Scheme VI

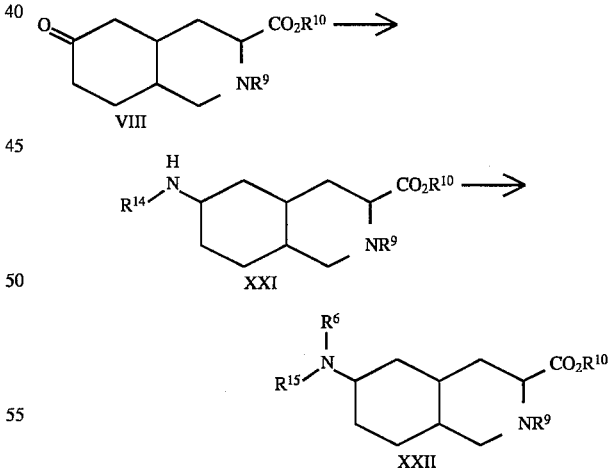

Generally, intermediate VIII is reacted with an amine to form the Schiff's base. The Schiff's base is reduced to produce intermediate XXI. The nitrogen of this compound is then acylated to produce the formula XXII compound. This compound may be further modified as described herein to prepare the formula I compounds wherein Z is $NR^6$.

More specifically, intermediate VIII is reacted with an amine of the general formula $R^{15}NH_2$ to form a Schiff's base which is reduced to intermediate XXI. The group $R^{15}$ preferably is —CH(R⁷)WR³, where W, R⁷ and R³ are as defined previously. The group R¹⁵ may also be a precursor to a group of the formula —CH(R⁷)WR³, such as cyanomethyl. This reaction is generally carried out in a polar organic solvent, such as ethanol, in the presence of powdered 4 Å molecular sieves at room temperature. Generally, intermediate VIII and the amine are combined, and then after a period of about twenty minutes to about two hours a reducing agent is added. A suitable reducing agent for this transformation is sodium cyanoborohydride.

Intermediate XXI is then acylated to produce intermediate XXII. Suitable acylating agents include activated esters and mixed anhydrides. Examples of activated esters include esters formed with such groups as p-nitrophenol, 2,4-dinitrophenol, trichlorophenol, 1-hydroxy-1H-benzotriazole, and 1-hydroxy-6-chloro-1H-benzotriazole. An example of a mixed anhydride is formic acetic anhydride. In a typical example, amine intermediate XXI is treated with the acylating agent in a polar organic solvent, such as tetrahydrofuran, at a temperature of about 25° C. to about the reflux temperature of the solvent.

The alkyl group, R¹⁵, may be chemically modified to produce the formula I compounds. For example, when R¹⁵ is cyanomethyl, treatment of intermediate XXII with tributyltin azide as described above leads to preparation of the tetrazolyl methyl derivative. The carboxyl protecting group and the protecting group on the ring nitrogen are selectively removed by treatment with 1N sodium hydroxide and iodotrimethysilane as described above, to prepare the formula I compounds wherein $R^1$ and $R^2$ are hydrogen.

The formula I compounds where Y is $NR_4$ are prepared in a manner similar to that described in the preceding paragraphs. Generally, these compounds are prepared by the reaction of 6-formyl intermediate XII with an amine to form the Schiff's base which is subsequently reduced. Suitable amines for this conversion include amines of the general formula $R^3WNH_2$, wherein $R^3$ is as defined previously, W is $(CH_2)_n$, n is 0, 1, or 2, or a precursor to a group of the formula $R^3WNH_2$.

More specifically, 6-formyl intermediate XII is reacted with aminoacetonitrile to form the corresponding Schiff's base. This reaction is generally carried out in a polar organic solvent, such as ethanol or methanol, in the presence of powdered 4 Å molecular sieves. The Schiff's base is then reduced with a suitable reducing agent, such as sodium cyanoborohydride. The amino group may be acylated as described above to prepare the formula I compounds wherein $R^4$ is an acyl group. The nitrile group may be converted to either a tetrazole or a carboxyl group as described herein.

The formula I compounds wherein Z is CHR⁷ and Y is CH₂ are prepared as outlined in Scheme VII.

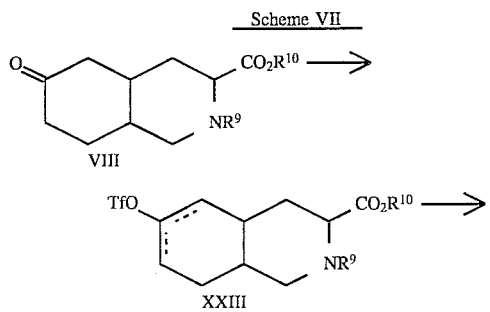

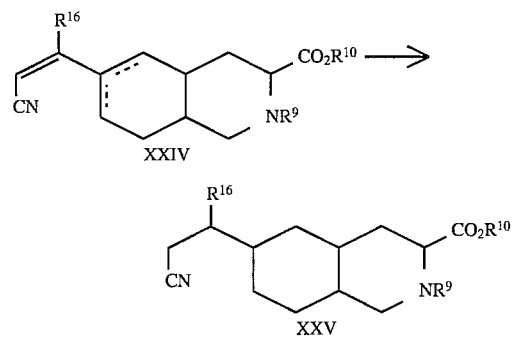

Generally, enol triflate intermediate XXIII is reacted with an α,β-unsaturated carbonyl compound or an α,β-unsaturated nitrile in the presence of bis(triphenylphosphine)palladium(II) chloride to produce unsaturated intermediate XXIV. Suitable α,β-unsaturated carbonyl compounds include α,β-unsaturated ketones, esters, aldehydes, and amides. Intermediate XXIV is optionally reduced to produce an intermediate to the formula I compounds.

More specifically, intermediate VIII is converted to the enol triflate intermediate XXIII by treatment with a strong base followed by triflylation. Suitable strong bases for this transformation include lithium bis(trimethylsilyl)amide and lithium diisopropylamide. The resulting enolate anion is acylated with either trifluoromethanesulfonic anhydride or N-phenyltrifluoromethanesulfonimide. This transformation is typically carried out in a polar aprotic solvent such as tetrahydrofuran.

Enol triflate intermediate XXIII is then alkylated to produce unsaturated intermediate XXIV. This reaction is generally accomplished by treating the triflate with a substituted α,β-unsaturated nitrile of the general formula HCR¹⁶CHCN, where R¹⁶ is hydrogen, C₁–C₄-alkyl, phenyl, or substituted phenyl, in the presence of bis(triphenylphosphine)palladium (II) chloride. The reaction is generally carried out in a degassed polar organic solvent such as dimethylformamide, in the presence of an amine base, such as triethylamine, at a temperature of about 70° C. to about 80° C.

Intermediate XXIV is optionally reduced to provide the corresponding saturated analog, intermediate XXV. Intermediate XXIV can be reduced by a dissolving metal reduction, such as Mg and MeOH, or by catalytic hydrogenation. The preferred method for this transformation is through catalytic hydrogenation. Suitable catalysts for this transformation include 5% palladium on carbon and 5% platinum on carbon; preferably palladium on carbon. The reduction is generally carried out at a hydrogen pressure of about 60 psi to about 100 psi at a temperature of about 25° C. to the reflux temperature of the solvent. Suitable solvents for this reaction include polar organic solvents such as ethanol and ethyl acetate.

The cyano intermediate XXV is then converted to a formula I compound as described above. This intermediate can be converted to a compound of formula I wherein R³ is tetrazole by reaction with tributyltin azide as described above. Alternatively, the cyano intermediate XXV can be converted to a formula I compound wherein R³ is CO₂H. These compounds are prepared by the reaction of the cyano intermediates with concentrated hydrochloric acid, which also removes the protecting groups.

The formula I compounds wherein Y is S, SO, or SO₂, and Z is CH₂, are prepared as outlined in Scheme VIII.

Scheme VIII

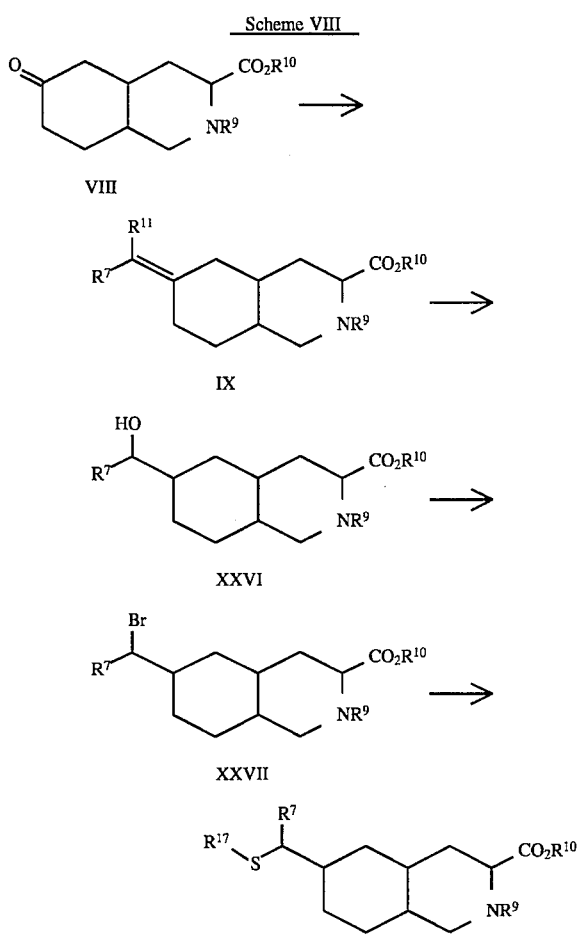

Generally, intermediate VIII is converted to the 6-formyl intermediate ($R^7$ is hydrogen) or a 6-acyl intermediate and then reduced to hydromy intermediate XXVI. This compound is converted to bromo intermediate XXVII and reacted with a variety of thiois to produce the formula I compounds wherein Y is S. These compounds may be oxidized to produce the formula I compounds wherein Y is SO or $SO_2$.

More specifically, intermediate VIII is converted to intermediate IX, where $R^{11}$ is methoxy, as described above. This intermediate is treated with a dilute aqueous acid in a polar organic solvent, such as tetrahydrofuran, to produce an intermediate XII. This compound is reduced to form hydroxymethyl intermediate XXVI. Suitable reducing agents include sodium borohydride and sodium cyanoborohydride. The reduction is generally carried out in a polar organic solvent, such as ethanol or isopropanol, at a temperature of 2° C. to about 25° C. Hydroxymethyl intermediate XXVI is then converted to the bromide using standard chemical reactions. In a typical example, treatment of the hydroxymethyl intermediate with triphenylphosphine and bromine in a polar organic solvent, such as methylene chloride, followed by the addition of an amine base, such as pyridine, leads to the production of bromo intermediate XXVII.

Intermediate XXVIII is reacted with a compound of general formula $R^{17}SH$, to produce intermediate XXVIII. The group $R^{17}$ may be a group of the formula —$(CH_2)_nR^3$, wherein n and $R^3$ are as defined previously, or a chemical precursor of this group. The group $R^{17}$ is preferably a group of the formula —$(CH_2)_nR^3$, wherein n and $R^3$ are as defined previously. In a typical example, intermediate XXVII is treated with 1H-1,2,4-triazole-3-thiol and an amine base to produce intermediate XXVIII. Suitable amine bases include triethylamine, N,N-diisopropylethylamine, N-methylmorpholine, pyridine, and collidine. The reaction is generally carried out at a temperature of about 50° C. to about 100° C. for a period of about four to about eighteen hours. Intermediate XXVIII may be treated with aqueous acid to prepare the compounds of formula I wherein $R^1$ and $R^2$ are hydrogen.

Alternatively, intermediate XXVIII may be treated with an oxidizing agent to prepare the formula I compounds wherein Y is SO or $SO_2$. A suitable oxidizing agent for transformation is 3-chloroperoxybenzoic acid. The oxidation is generally carried out in a polar organic solvent, such as methylene chloride. The formula I compounds wherein Y is SO are prepared by treating the corresponding formula I compound wherein Y is S with the oxidizing agent am a temperature of about –78° C. to about –30° C. The reaction is generally complete after a period of about one to about four hours. The formula I compounds where Y is $SO_2$ are prepared by treating the corresponding formula I compound where Y is S or SO with the oxidizing agent at a temperature of about room temperature to about 50° C. Preferably, the oxidation is carried out at room temperature in methylene chloride with an excess of 3-chloroperoxybenzoic acid. The reaction is generally complete after a period of about eighteen hours.

The compounds of formula I where Y is oxygen are generally prepared as described in Scheme IX

Scheme IX

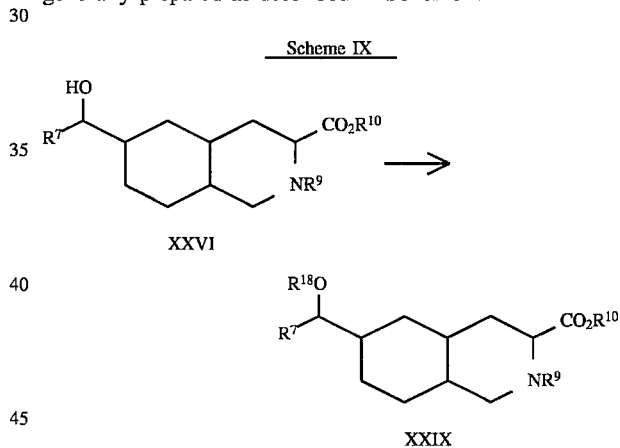

Generally, intermediate VIII is converted to the 6-hydroxymethyl intermediate XXVI. This intermediate is alkylated with a variety of alkyl halides. The resulting products are converted to the formula I compounds using standard synthetic techniques as described herein.

More specifically, hydroxymethyl intermediate XXVI, prepared as described above, is alkylated by a compound of general formula $R^{18}X'$. The group $R^{18}$ is preferably a group of the formula —$(CH_2)_nR^3$, where n and $R^3$ are as defined previously. The group X' is chloro, bromo, iodo, mesyloxy or tosyloxy. Preferably X' is bromo, chloro, or iodo. Examples of such akylating agents include 5-bromomethyl-3-methoxyisoxazole, 3-diphenylmethoxy-4-iodomethyl-1,2,5-thiadiazole, and the like. Alternatively, the group $R^{18}$ can be a precursor to a group of the formula —$(CH_2)_nR^3$, such as cyanomethyl, methoxyethoxymethyl, and methoxymethyl. In one example, intermediate XXVI and an amine base in a polar organic solvent is treated with the N,N-alkylating agent. Suitable amine bases include diisopropylethylamine, triethylamine, pyridine, and collidine. One example of a suitable alkylating agent is chloromethyl methyl ether. The reaction is typically carried out at a temperature of about 0° C. to about 10° C. The product of this reaction is converted to the cyanomethyl intermediate XXIX by sequential treatment with trimethylsilyl cyanide and boron trifluoride etherate. This reaction is carried out in a polar organic solvent, such as methylene chloride, at a temperature of about 0° C. to about 10° C.

The resulting cyanomethyl intermediate XXIX can be converted to the tetrazolylmethyl intermediate by treatment with tributyltin azide as described above. Alternatively the cyanomethyl intermediate can be converted to the carboxymethyl intermediate by treatment of the cyanomethyl intermediate with acid. Preferably, the acid is an aqueous acid, such as hydrochloric, and the reaction is carried out at the reflux temperature of the solution. This procedure also results in the removal of the protecting groups of the carboxyl group and the ring nitrogen, to provide the formula I compound wherein $R^1$ and $R^2$ are hydrogen.

The preceding Examples are useful for preparation of the compounds of formula I as either racemic mixtures or as single enantiomers. when the synthesis begins with racemic. intermediate VIII, the products are generally racemic mixtures. However, when the synthesis begins with intermediate (−)-VIIIb the products are generally a single enantiomer. The relative configuration of the carbon atom at the C-6 position of the ring for the compounds where Z is $CH_2$ may be controlled as shown in Schemes X and XI.

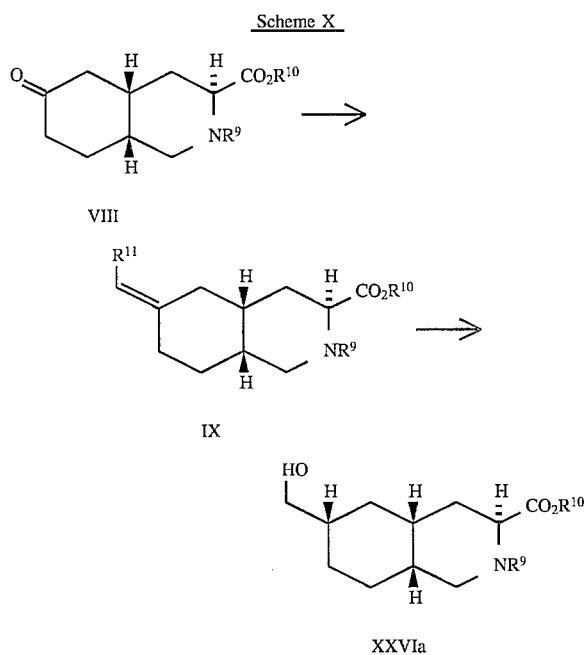

XXVIa

Generally, Scheme X illustrates a process for the preparation of the formula XXVIa compound having the relative stereochemistry as shown. Enantiopure VIII is converted to unsaturated intermediate IX under standard Wittig conditions. The product is stereoselectively converted to intermediate XXVIa by hydroboration and then oxidation.

Specifically, intermediate VIII is reacted with a Wittig reagent, such as methyltriphenylphosphonium bromide, to produce Intermediate IX, where $R^{11}$ is hydrogen. This reaction is generally accomplished as described previously, by treating the phosphonium bromide with a strong base, such as sodium bis(trimethylsilyl)amide, to generate the ylid. This ylid is then reacted in a polar organic solvent, such dry tetrahydrofuran, with VIII to provide the methylene derivative of formula IX. This reaction is generally carried out between 0° C. and the reflux temperature of the solvent. When a slight molar excess of the phosphonium salt is employed, the reaction is generally complete in about six hours.

Intermediate IX is then converted stereoselectively to Intermediate XXVIa. A preferred method of accomplishing this conversion is hydroboration followed by oxidation. A suitable reagent for the hydroboration is borate-methyl sulfide. This hydroboration is generally carried out in a polar organic solvent, such as tetrahydrofuran, at a temperature of about 0° C. to about room temperature. The reaction is generally complete after a period of about two to about four hours. The product from the hydroboration is then oxidized to intermediate XXVIa. A suitable oxidizing agent for this transformation is hydrogen peroxide. The oxidation is generally accomplished by treating the hydroboration reaction mixture with hydrogen peroxide and stirring the resulting mixture at room temperature. The reaction is generally complete after a period of about one to two hours.

Alternatively, the configuration of the carbon atom at the C-6 position of the ring may be controlled to form the formula I compound where the hydrogen atom at the C-6 position is trans relative to the hydrogen atom at the C-4a position as shown in Scheme XI.

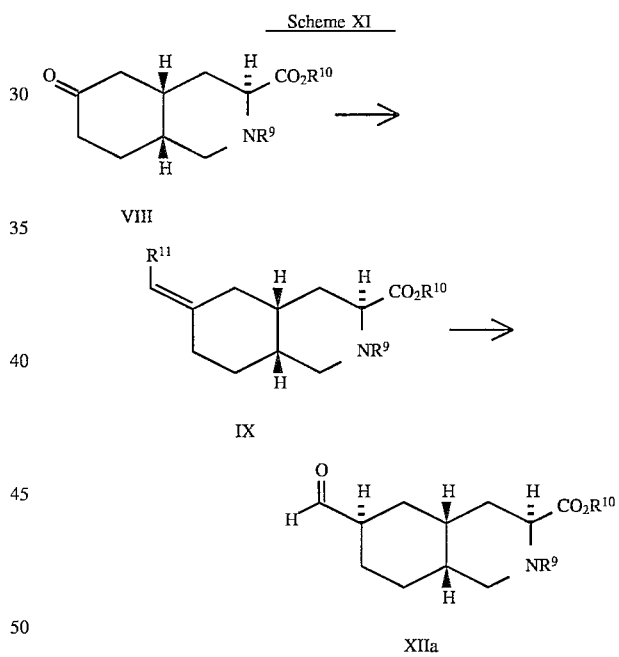

XIIa

Generally, enantiopure VIII is reacted with a Wittig reagent to form intermediate IX. This compound is then stereoselectively hydrolyzed to 6-formyl intermediate XIIa.

Specifically, intermediate VIII is reacted with Wittig reagent of the formula $Ph_3PCHOCH_3$ to produce intermediate IX, where $R^{11}$ is methoxy. This reaction is generally accomplished as described previously. Intermediate IX is then converted to Intermediate XIIa by treatment with aqueous acid. A suitable acid for this transformation is dilute hydrochloric acid, such as 1N hydrochloric acid. The reaction is generally carried out at 60° C. in a polar organic solvent, such as acetonitrile for a period of about two to about eight hours.

Alternatively, intermediate XIIa can be prepared from intermediate XXVIa. The enantiopure alcohol XXVIa is oxidized to the corresponding aldehyde using standard Swern oxidation conditions or other dimethylsulfoxide (DMSO) based reagents. Mancuso, Huang, and Swern, *J. Org. Chem.*, 43, 2480–2482 (1978); Epstein and Sweat, *Chem. Rev.* 67, 247–260 (1967); and Smith, Leenay, Lin, Nelson, and Ball, *Tetr. Lett.*, 29, 49–52 (1988). The aldehyde, wherein the hydrogen at C-6 is cis to the bridgehead hydrogens, is treated with mild base to produce XIIa. Suitable mild bases include tertiary amines, including triethylamine and N,N-diisopropylethylamine, and sodium bicarbonate. Preferably, the epimerization of the C-6 hydrogen occurs during work-up of the Swern oxidation.

Another aspect of the present invention is the compounds of the formula

wherein:

J is a group of the formula

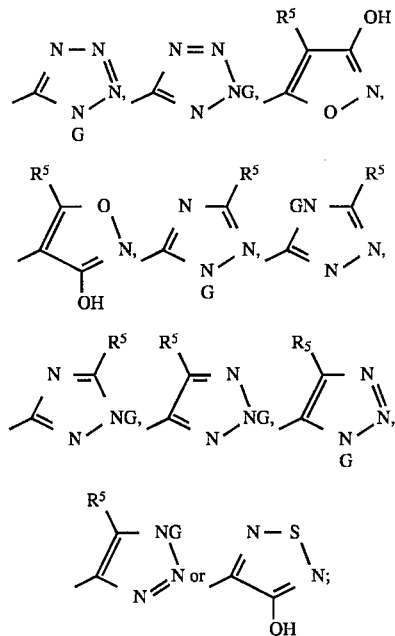

wherein:

Q is $CHR^7P^+(Ph)_3X^-$, $CHR^7PO(Ph)_2$, $CR^7MSiR'_3$, $CH(SiR'_3)PO(OR')_2$, or $CH_2SnR'_3$;

R' is $C_1$–$C_6$ alkyl or phenyl;

G is a nitrogen protecting group o5 hydrogen;

M is $Li^+$ or $Mg^{+2}X^-$;

$X^-$ is bromide, chloride, iodide, tetrafluoroborate, or hexafluorophosphate;

and $R^5$ and $R^7$ are as defined previously.

Generally, the compounds are prepared by a two step process. The steps comprise synthesis of the appropriate heterocycle and a functional group interconversion. The heterocycles, such as tetrazole, hydroxy-substituted isoxazoles, triazoles, and hydroxy substituted thiadiazoles, are generally prepared using standard synthetic methodologies. The preparation of these heterocyclic systems is described below. The functional group interconversion constitutes the conversion of a group that is not reactive in the synthesis of the heterocycle to a triphenylphosphonium, trialkylstannane, phosphonate, lithium, Grignard, or diphenylphosphine oxide group. Examples of such functional group interconversions are described below. The trialkylstannane and diphenylphosphine oxide groups may be prepared before synthesis of the heterocycle.

The tetrazole ring is prepared using standard synthetic methodology. See Butler, "Recent Advances in Tetrazole Chemistry," *Advances in Heterocyclic Chemistry*, 21, 354–361 (1977). A tetrazole is formed by the reaction of a nitrile with an azide reagent in non-reactive solvent. Suitable azide reagents include inorganic azides, such as sodium azide, lithium azide, or ammonium azide, and reagents such as 1,1,3,3-tetramethylguanidinium azide and tributyltin azide. Suitable reaction conditions include the use of lithium or ammonium azide in dimethylformamide, sodium azide in diglyme and N,N-dimethylethanolamine hydrochloride, or tributyltin azide in a non-reactive solvent such as dimethoxyethane, toluene, or tetrahydrofuran. The presence of aluminum trichloride has been found to enhance the reaction when inorganic azides are used. Alternatively, the nitrile may be reacted with sodium azide, hydrochloric acid and a trialkylamine. Suitable trialkylamines for this reaction include triethylamine, N,N-diisopropylethylamine, and N-methylmorpholine. The reaction is generally heated at or near the reflux temperature of the reaction mixture. The transformation is generally complete under these conditions in about one to about three days. The preferred method for the conversion of a nitrile to a tetrazole is reaction of the nitrile with a mixture of sodium azide and tributyltin chloride. This reaction is carried out in an organic solvent such as toluene, at a temperature of about 75° C. to about 100° C. This reaction generally requires from about 20 about 30 hours for completion.

The hydroxy-substituted isoxazoles are prepared using standard synthetic methodology. See, Kochetkov and Sokolov, "Recent Developments in Isoxazole Chemistry," *Advances in Heterocyclic Chemistry*, 2, 365–278 (1963). Generally, a β-keto ester or a β-keto acid is condensed with hydroxylamine to form a hydroxy-substituted isoxazole. Katritzky and Oksne, *Proc. Chem. Soc.*, 387–388 (1961); Jacobsen, *Can. J. Chem.*, 62, 1940 (1984). The β-keto ester is converted to the corresponding oxime derivative by treatment with hydroxylamine and concentrated hydrochloric acid. This reaction may be carried out in an alcohol co-solvent, such as methanol or ethanol, preferably using the alcohol which corresponds to the ester group as an organic co-solvent. The reaction is carried out at a temperature of about 0° C. to the reflux temperature of the solvent, preferably at a temperature of about 25° C. to about 50° C. After preparation of the oxime, the oxime intermediate is cyclized to form the isoxazole ring. This cyclization is typically carried out by treating the oxime intermediate with 2N sodium hydroxide at pH 10. The reaction is generally carried out at a temperature of 0° C. to 50° C., preferably at room temperature. An organic co-solvent, such as methanol or acetonitrile, can be used where the oxime intermediate is not soluble in water. This reaction generally requires from about 10 hours to about 24 hours for completion.

Alternatively, the hydroxy-substituted isoxazoles are prepared by the reaction of propargyl alcohol with dibromoformaldoxime, followed by hydrolysis of the bromo group. First, propargyl alcohol is reacted with dibromoformaldoxime to produce a cycloadduct. This reaction is carried out at a temperature of about 15° C. to about 50° C., preferably at room temperature. A suitable solvent for this reaction is ethyl acetate. The cycloadduct, 3-bromo-5-hydroxymethylisoxazole, is then treated with aqueous base to hydrolyze the bromo group. Suitable aqueous bases include sodium hydroxide and potassium hydroxide; potassium hydroxide is preferred. The reaction is carried out in a mixture of water and a water miscible organic solvent, such as methanol. The reaction is preferably carried out at the reflux temperature of the solvent mixture.

The triazoles are prepared using standard synthetic methodology. See, Gilchrist and Gymer, "1,2,3-Triazoles," *Advances in Heterocyclic Chemistry*, 16, 33–63 (1974); *Advances in Heterocyclic Chemistry*, 18, 106 (1975). The 1,2,3-triazoles are generally prepared by the reaction of an azide with an $\alpha$-diketone or a substituted acetylene. Suitable azide reagents include inorganic azides, such as sodium azide, lithium azide, or ammonium azide. Suitable reaction conditions include the use of lithium or ammonium azide in dimethyl formamide, and sodium azide in diglyme and N,N-dimethylethanolamine hydrochloride. Alternatively, 1,2,3-triazoles are prepared by the reaction of a primary amine with an N-tosyl amidrazone containing two leaving groups, such as chloride, $\alpha$ to the amidrazone amine. Sakai, *Bull. Chem. Soc. Jpn.*, 59, 179 (1986). Suitable solvents for this reaction include alcoholic solvents, such as methanol. The reaction is carried out at a temperature of about $-10°$ C. to about 25° C., preferably at 0° C. The 1,2,4-triazoles are generally prepared by the reaction of an acyl hydrazine with either a hydrazine or an N-substituted hydrazine. This reaction is typically carried out in a mixture of acetonitrile and triethylamine at a temperature of about 0° C. to about 50° C., preferably at room temperature. Alternatively, 1,2,4-triazoles are prepared by the reaction of an amidrazone with acyl hydrazine in a strong base. A suitable strong base for this transformation is a metal alkoxide, such as sodium methoxide or potassium t-butoxide. This reaction is typically run under anhydrous conditions, such as a mixture of dry ethanol and p-xylene. This transformation is typically carried out at room temperature. Francis, *Tetr. Lett.*, 28, 5133 (1987).

The tetrazoles and triazoles are optionally protected with a nitrogen protecting group. Suitable nitrogen protecting groups include trityl, benzyl, t-butyl, t-butyldimethylsilyl, and triphenylsilyl. The protected compounds are prepared by the reaction of a tetrazole or triazole with a trityl, benzyl, t-butyldimethylsilyl, triphenylsilyl halide, such as chloride or bromide, in the presence of a base. Suitable bases include tertiary amines, such as triethylamine, N,N-diisopropylethylamine, pyridine, sodium bicarbonate, sodium hydroxide, and potassium hydroxide. Suitable solvents include water and polar organic solvents, such as dimethylformamide, acetonitrile, and methylene chloride. The t-butyl group is prepared by the reaction of either a tetrazole or triazole with isobutylene in strong acids. Suitable acids include sulfuric and toluenesulfonic The 1,2,5-thiadiazoles are be prepared using standard synthetic methodology. See, *Advances in Heterocyclic Chemistry*, 30, 65–66 (1982). Generally, 1,2,5-thiadiazoles are prepared by the reaction of the corresponding diamine or $\alpha$-amino amide with sulfur dichloride or thionyl chloride. Weinstock, *Tetr. Lett.*, 1263 (1966). A suitable solvent for this reaction is dry dimethylformamide. The reaction is typically carried out at a temperature of about $-10°$ C. to about 25° C., preferably at 0° C. Once the addition of the sulfur dichloride or thionyl chloride is complete, the reaction is typically allowed to warm to room temperature.

The other step comprises the conversion of a functional group, that is not reactive in the synthesis of the heterocycle, to a triphenylphosphonium, trialkylstannane, phosphonate, lithium, Grignard, or diphenylphosphine oxide. Suitable functional groups for conversion are hydroxy, bromo, chloro, or protected hydroxy.

The triphenylphosphonium compounds are prepared using standard synthetic methodology. These compounds are prepared by the reaction of triphenylphosphine with a heterocyclicalkyl bromide, chloride, or iodide. Suitable solvents for this reaction are organic solvents, such as acetonitrile, toluene, xylene, and dimethylformamide. The reaction may be carried out in the absence of a solvent. The reaction is typically carried out at a temperature of about 80° C. to about 150° C., or the reflux temperature of the solvent. Alternatively, the triphenylphosphonium compounds are prepared by the reaction of a heterocyclic hydroxyalkyl compound with triphenylphosphine hydrobromide. This reaction is generally carried out in a solvent suitable for azeotropic removal of water, such as toluene or xylene, at a temperature above the boiling point of the azeotrope. The reaction may be carried out in the absence of a solvent. This reaction generally requires from about 1 hour to about 5 hours for completion.

The trialkylstannanes are prepared using standard organometallic methodology. Trialkylstannanes are prepared by the reaction of a heterocyclicalkyl halides, such as bromides or chlorides, with tributyltin chloride and zinc. Knochel, *Organometallics*, 9, 3053 (1990). This reaction is typically carried out in a polar organic solvent such as methylene chloride, at a temperature of about $-70°$ C. to about 5° C. Alternatively, a heterocyclicalkyl bromide may be treated with magnesium to form a Grignard complex, and then treated with trialkyltin chloride. Delmond, *J. Organomet. Chem.*, 26, 7 (1971). The reaction of the alkyl bromide with magnesium may be carried out in a polar organic solvent such as ether and tetrahydrofuran, at a temperature of about $-10°$ C. to about 50° C. Preferably, the reaction is carried out in dry ether. The reaction of Grignard intermediate with tributyltin chloride is typically carried out at the reflux temperature of the solvent.

The diphenylphosphine oxide group is prepared using standard synthetic methodology. Generally, a heterocyclicalkyl halide, tosylate, or mesylate is reacted with lithium diphenylphosphine. The lithium diphenylphosphine reagent is prepared by the reaction of diphenylphosphine with n-butyl lithium. The reaction is typically carried out in a polar organic solvent, such as ether or tetrahydrofuran, at a temperature of about $-20°$ C. to about 0° C. Brown, *J. Chem. Soc. Perk. Trans. II*, 91 (1987). The intermediate heterocyclicalkyl diphenylphosphine compound is oxidized to the phosphine oxide using dilute bleach (sodium hydrochloride) during the work-up of the reaction.

The $\alpha$-silyl phosphonate compounds are prepared using standard synthetic methodology. Aboujaoude, *Synthesis*, 934–937 (1986). A heterocyclicalkyl halide, such as the bromide or chloride, is reacted with triethylphosphate to prepare the corresponding phosphonate. This reaction is typically carried out in an organic solvent, such toluene, at the reflux temperature of the solvent. The intermediate phosphonate is then treated with a strong base, such as lithium diisopropylamide, followed by the addition of trimethylsilyl chloride to prepare the $\alpha$-silyl phosphonate. The silylation reaction is typically carried out in a dry organic solvent, such as ether or tetrahyrofuran, at a temperature of about $-78°$ C. to about $-50°$ C.

The Peterson reagents, the $\alpha$-silyl Grignard and lithium compounds, are prepared using standard synthetic methodology. These reagents are prepared by the reaction of a heterocyclic alkyl $\alpha$-silyl halide, such as a bromide or a chloride, with magnesium metal or lithium metal. Boaz, *J. Med. Chem.*, 14, 1971. The $\alpha$-silyl chloride is preferred for the preparation of the Grignard reagent. Sexton, *J. Org.*

*Chem.*, 56, 698 (1991). The α-silyl bromide is preferred for preparation of the heterocyclicalkyl lithium compound. The reaction is typically carried out in a dry organic solvent, such tetrahydrofuran or dry ether, at a temperature of 0° C. to about room temperature.

More specifically, [2-(1(2)H-tetrazole-5-yl)ethyl] triphenylphosphonium bromide is prepared from 3-hydroxypropionitrile. The hydroxynitrile is first converted to the corresponding tetrazole compound. The preferred method for the conversion of this nitrile to a tetrazole is the reaction of the nitrile with mixture of sodium azide and tributyltin chloride. This reaction is carried out in an organic solvent, such as toluene, at a temperature of about 75° C. to 100° C. This reaction generally requires from about 20 to about 30 hours for completion. The product of this reaction, 5-(2-hydroxyethyl)tetrazole, is reacted with triphenylphosphine hydrobromide to produce [2-(1(2)H-tetrazole-5-yl) ethyl]triphenylphosphonium bromide. This reaction is generally carried out in a solvent suitable for azeotropic removal of the water that is formed during the reaction, such as toluene and xylene, at a temperature above the boiling point of the azeotrope. The reaction may also be carried out without the removal of water. When the reaction is carried out in xylene, the temperature of the reaction is about 120° C. to about 150° C. The reaction generally requires from about one to about five hours for completion.

The formula I compounds wherein Z is CH are prepared in Scheme XII.

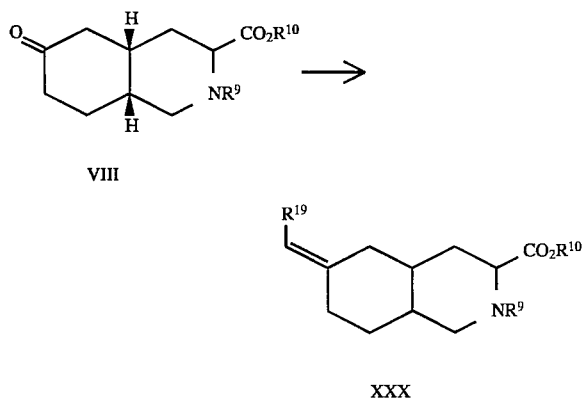

Scheme XII

VIII

XXX

Generally, intermediate VIII is reacted with a Wittig reagent, a Horner-Emmons reagent, or a variant thereof, to produce a compound of formula XXX. More specifically, intermediate VIII is reacted with a reagent of the general formula $QCH_2R^{19}$ wherein Q is as defined previously and $R^{19}$ is $-YWR^3$. The compound of the formula $QCH_2R^{19}$ is preferably a compound of the formula $JCH_2Q$, wherein J and Q are as defined previously. In a typical example, Q is $CH_2P(Ph)_3{}^+Cl^-$ and $R^{19}$ (J) is tetrazole-5-ylmethyl. This reaction is generally accomplished by treating the phosphonium reagent with a strong base, such as sodium hydride or sodium bis(trimethylsilyl)amide to generate the ylid, which is then reacted in a polar organic solvent, such as dimethylformamide with VIII to provide the methylene derivative of formula XXX. This reaction is generally carried out at a temperature of about 0° C. to about 30° C., preferably at room temperature, for a period of about one to about three hours. The formula XXX compound, wherein $R^9$ is methoxycarbonyl and $R^{10}$ is ethyl, may be treated with warm 5N sodium hydroxide to produce the formula I compounds wherein $R^1$ and $R^2$ are hydrogen.

The formula XXX compound is optionally reduced to prepare the formula I compounds wherein Z is $CH_2$. When $R^9$ is alkoxycarbonyl and $R^{10}$ is $C_1-C_6$ alkyl, this reduction can be carried out to stereoselectively produce a compound of the formula

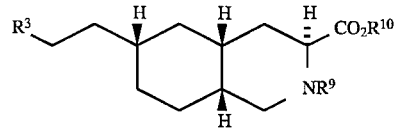

The method of reduction for the stereoselective transformation is catalytic hydrogenation. The preferred catalyst is platinum oxide, at a weight ratio of about five percent. Suitable solvents for this reduction include ethanol and ethyl acetate. The reduction is preferably carried out at a hydrogen pressure of about one atmosphere and at a temperature of about 20° C. to about 30° C. Preferably, the reduction is carried out at room temperature. The reaction is generally complete after about 24 hours. When $R^3$ is a tetrazole group, the stereoselectivity is about 6:1 (6-H beta:6-H alpha).

The formula I compounds, wherein $R^1$ is $C_1-C_{10}$ alkyl, arylalkyl, or acyl, are prepared from the corresponding compounds wherein $R^1$ is hydrogen. The compounds wherein $R^1$ is $C_1-C_{10}$ alkyl or arylalkyl are prepared by reductive alkylation. Generally, an aldehyde or ketone of the corresponding $C_1-C_{10}$ alkyl group or arylalkyl group is reacted with the formula I compound, wherein $R^1$ is hydrogen, to form an intermediate Schiff's base. The reaction is carried out in a polar organic solvent, such as methanol, or a mixture of polar organic solvents, such as a mixture of dimethylformamide and methanol, at a temperature of about 25° C. to about 100° C. The reaction for the formation of the Schiff's base is preferably carried out at a temperature of from about 25° C. to about 30° C. for about 30 minutes to about 2 hours in methanol.

The intermediate Schiff's base is then reduced, preferably without isolation, to produce the $C_1-C_{10}$ alkyl or arylalkyl derivatives. The reduction of the Schiff's base can be effected using a chemical reducing agent such as sodium cyanoborohydride. The reaction can be carried out in a polar organic solvent, such as methanol, or a mixture of polar organic solvents, such as dimethylformamide and methanol. The reduction can be carried out at a temperature of about 25° C. to about 100° C. for about 1 to about 5 hours. The reduction is preferably carried out using an excess of sodium cyanoborohydride in methanol at about 25° C. to about 40° C. for a period of 1 to 2 hours.

The formula I compounds wherein $R^1$ is acyl are prepared by the reaction of a formula I compound wherein $R^1$ is hydrogen with an activated ester of the desired acyl group. The term activated ester means an ester which renders the carboxyl function of the acylating group reactive to coupling with the amino group of the decahydroisoquinoline ring. The preferred activated ester is the 2,4,5-trichlorophenyl ester. The reaction is carried out in a polar organic solvent, such as dimethylformamide or tetrahydrofuran, at a temperature of about 25° C. to 110° C. for a period of about 1 to about 5 hours. The reaction for the formation of acyl derivatives of the formula I compounds is preferably carried out at a temperature of about 30° C. to about 70° C. for a period of about 2 to about 4 hours.

The formula I compounds wherein $R^2$ is substituted alkyl, cycloalkyl, or arylalkyl are prepared from the corresponding compounds wherein $R^2$ is hydrogen. These compounds are generally prepared using standard synthetic methodologies.

In a typical example, the formula I compound, wherein $R^1$ is hydrogen, is reacted with an arylalkyl halide, such as benzyl bromide, in the presence of a base to produce the arylalkyl ester derivative. Suitable bases for this transformation include tertiary alkylamines, such as triethylamine, N,N-diisopropylethyl amine, N-methylmorpholine, pyridine, and collidine, and sodium carbonate. The reaction is typically run in an organic solvent, such as tetrahydrofuran, acetonitrile, and dimethylformamide. Alternatively, the formula I compound, wherein $R^1$ is hydrogen, can be reacted with a substituted alkyl, cycloalkyl, or arylalkyl alcohol in the presence of acid to produce the corresponding ester. Typically, this reaction is carried out with an excess of the alcohol in the presence of concentrated sulfuric acid.

The formula I compounds of the present invention are excitatory amino acid antagonists. In particular, these compounds are selective for the AMPA subtype of excitatory amino acid receptors. Therefore, another aspect of the present invention is a method of blocking the AMPA excitatory amino acid receptors in mammals which comprises administering to a mammal requiring decreased excitatory amino acid neurotransmission a pharmaceutically-effective amount of a compound of formula I.

The term "pharmaceutically-effective amount", is used herein to represent an amount of the compound of the invention which is capable of blocking the AMPA excitatory amino acid receptors. The particular dose of compound administered according to this invention will of course be determined by the particular circumstances surrounding the case, including the compound administered, the route of administration, the particular condition being treated, and similar considerations. The compounds can be administered by a variety of routes including the oral, rectal, transdermal, subcutaneous, intravenous, intramuscular, or intranasal routes. Alternatively, the compounds may be administered by continuous infusion. A typical daily dose will contain from about 0.01 mg/kg to about 20 mg/kg of the active compound of this invention. Preferred daily doses will be about 0.05 mg/kg to about 10 mg/kg, more preferably about 0.1 to about 5 mg/kg.

A variety of physiological functions have been shown to be subject to influence by excessive or inappropriate stimulation of excitatory amino acid neurotransmission. The formula I compounds of the present invention are believed to have the ability to treat a variety of neurological disorders in mammals associated with this condition which include acute neurological disorders such as cerebral deficits subsequent to cardiac bypass surgery and grafting, stroke, cerebral ischemia, spinal cord trauma, head trauma, perinatal hypoxia, cardiac arrest and hypoglyemic neuronal damage. The formula I compounds are believed to have the ability to treat a variety of chronic neurological disorders such as Alzheimer's Disease, Huntington's Chorea, amyotrophic lateral sclerosis, AIDS-induced dementia, ocular damage and retinopathy, and idiopathic and drug-induced Parkinson's Disease. The present invention also provides methods for treating these disorders which comprise administering to a patient in need thereof an effective amount of a compound of formula I.

The formula I compounds of the present invention are also believed to have the ability to treat a variety of other neurological disorders in mammals that are associated with glutamate dysfunction including muscular spasms, convulsions, migraine headaches, urinary incontinence, psychosis, opiate tolerance and withdrawal, anxiety, emesis, brain edema, chronic pain, and tardive dyskinesia. The formula I compounds are also useful as analgesic agents. Therefore, the present invention also provides methods for treating these disorders which comprise administering to a patient in need thereof an effective amount of a compound of formula I.

Experiments were performed to demonstrate the selective inhibitory activity of the formula I compounds of this invention at the α-amino-3-hydroxy-5-methylisoxazole-4-propionic acid (AMPA) subtype of excitatory amino acid receptors. The formula I compounds were tested for their ability to inhibit NMDA, AMPA, and kainic acid receptor binding to rat membranes in a radioligand binding assay using [$^3$H]CGS19755, [$^3$H]AMPA, and [$^3$H]KA. For all radioligand binding assays, male Sprague-Dawley rats were used. Displacement of the specific binding [$^3$H]CGS19755 (10 nM) to Triton-X-treated synaptosomal membranes of rat forebrain was used to determine NMDA receptor affinity. Non-specific binding was determined using 10 μM L-glutamate. Samples were incubated in an ice-bath for 30 minutes, and bound ligand was separated from the free ligand by rapid filtration through WHATMAN GF/B glass fiber filters. Murphy et al, *British J. Pharmacol.*, 95, 932–938 (1988). Kainate binding was performed using washed synaptosomal membranes from the rat forebrain as described by Simon et al. Simon et al, *J. Neurochem.*, 26, 141–147 (1976). Tritiated kainate (5 nM) was added to 50 mM Tris-HCl buffer (pH 7.4 at 4° C.) containing 200–300 μg/ml of tissue protein. Samples were incubated for 30 minutes in an ice-bath, then rapidly filtered using a Brandel cell harvester and WHATMAN GF/C filters. Filters were washed twice with 3 ml of cold buffer. Non-specific binding was determined using 100 μM non-labeled kainate. The binding of [$^3$H]AMPA (5 nM) was conducted with crude membranes of rat forebrain in the presence of 100 mM KSCN as described by Nielson et al. Nielson et al, *Eur. J. Med. Chem. Chim. Ther.*, 21, 433–437 (1986). Non-specific binding was determined with 10 μM non-labeled AMPA. The concentration of the formula I compound that inhibited 50% binding ($IC_{50}$, mean±standard error, n=3) as calculated by linear regression of displacement data transformed to the Hill equation as described by Bennett. Bennett, *Neurotransmitter Receptor Binding*, 57–90 (1978). The results of the radioligand binding assays are shown in Tables I and II.

TABLE I

Receptor Binding of Racemic Formula I Compounds

| Compound[a] | | IC$_{50}$ (μM)[b] | | |
|---|---|---|---|---|
| No. | Structure | NMDA | AMPA | KA |
| 1 | | 26.40 ± 1.95 | 4.82 ± 1.23 | 246.98 ± 7.5 |
| 2 | | 60.6 ± 24.8 | 59.6 ± 4.3 | 180.0 ± 22.1 |
| 3 | | >100 | 29.1[c] | >100 |
| 4 | | 29.4 ± 6.8 | 0.90 ± 0.14 | 30.1 ± 1.6 |
| 5 | | 47.9 ± 3.9 | 4.9 ± 0.4 | 37.3 ± 2.3 |
| 6 | | 27.0 ± 9.9 | 16.75 ± 0.46 | 18.65 ± 0.33 |
| 7 | | >10 | >10 | >10 |
| 8 | | 49.21 ± 1.86 | 10.59 ± 2.00 | 28.76 ± 2.21 |
| 9 | | >100 | 56.23 ± 4.60 | >100 |

TABLE I-continued

Receptor Binding of Racemic Formula I Compounds

| No. | Structure | NMDA | AMPA | KA |
|---|---|---|---|---|
| 10 | (tetrazole-propyl-cyclohexane-amino acid) | >100 | 32[c] | >100 |
| 11 | (HO2C-propyl-cyclohexane-amino acid) | 43.9 ± 4.1 | 27.8 ± 0.6 | >100 |
| 12 | (HO2C-propyl-cyclohexane-amino acid isomer) | 61.8[c] | 11.1[c] | >100 |
| 13 | (hydroxyisoxazole-ethyl-cyclohexane-amino acid) | >100 | 13.82 ± 1.24 | >100 |
| 14 | (triazole-S-CH2-cyclohexane-amino acid) | >10 | >10 | >10 |
| 15 | (triazole-SO2-CH2-cyclohexane-amino acid) | >100 | 1.67 ± 0.14 | >100 |
| 16 | (CH3SO2NH-CO-ethyl-cyclohexane-amino acid) | >100 | 80[c] | >100 |
| 17 | (tetrazole-NH-CO-ethyl-cyclohexane-amino acid) | >100 | 45.7[c] | >100 |
| 18 | (tetrazole-CH(CH3)-cyclohexane-amino acid) | 43.1[c] | 3.37[c] | 28.2[c] |

TABLE I-continued

Receptor Binding of Racemic Formula I Compounds

| | Compound[a] | | IC$_{50}$ (μM)[b] | |
|---|---|---|---|---|
| No. | Structure | NMDA | AMPA | KA |
| 19 | (structure) | 13.8[c] | 6.58[c] | >100 |
| 20 | (structure) | >100 | 83.4[c] | >100 |

[a] The compounds were tested as racemic mixtures with the relative stereochemistry as shown.
[b] Mean ± standard error (n = 3), unless otherwise indicated.
[c] The data is the result of a single experiment.

TABLE II

Receptor Binding of Enantiopure Formula I Compounds

| | Compound[a] | | IC$_{50}$ (μM)[b] | |
|---|---|---|---|---|
| No. | Structure | NMDA | AMPA | KA |
| 21 | (structure) | 12.1 ± 2.0 | 1.35 ± 0.13 | 28.1 ± 1.7 |
| 22 | (structure) | 99.2[c] | 15.3[c] | 85.3[c] |
| 23 | (structure) | 16.3[c] | 0.58 ± 0.03 | 12.5[c] |
| 24 | (structure) | >10 | 21.9[c] | >100 |

TABLE II-continued

Receptor Binding of Enantiopure Formula I Compounds

| No. | Compound[a] Structure | IC$_{50}$ ($\mu$M)[b] NMDA | AMPA | KA |
|---|---|---|---|---|
| 25 | (triazole-S-CH2-cyclohexyl-CH2-CH(NH)-CH2-CH(CO2H)) | >100 | 17.8[c] | 27.9[c] |
| 26 | (pyrazole-SO2-CH2-cyclohexyl-CH2-CH(NH)-CH2-CH(CO2H)) | >100 | 0.63[c] | >100 |
| 27 | (pyrazole-SO2-CH2-cyclohexyl-CH2-CH(NH)-CH2-CH(CO2H)) | 60.93[c] | 23.6[c] | >100 |

[a]The compounds were tested as pure enantiomers with the relative and absolute stereochemistry as shown.
[b]Mean ± standard error (n = 3).
[c]The data is the result of a single experiment.

The depolarization of rat cortical wedges was used to test the selectivity and potency of the formula I compounds as AMPA antagonists using a technique similar to that described by Harrison and Simmonds. Harrison and Simmonds, *Bri. J. Pharmacol.*, 84, 381–391 (1984). Generally, 4-ml aliquots of NMDA (40 μM), AMPA (40 μM), and kainate (10 μM) were superfused (2 ml/min.) on the grey matter at intervals of 15–20 minutes until stable responses were attained. The tissue was then exposed for 15 minutes to various concentrations of the formula I compounds before retesting the agonists. The IC$_{50}$ values were calculated from linear regression of log dose-response curves, each point the mean of at least three observations on separate slices from more than one animal. The results of these tests are shown in Tables III and IV.

TABLE III

Antagonism of Cortical Wedge Depolarization by Racemic Formula I Compounds

| No. | Compound[a] Structure | IC$_{50}$ ($\mu$M)[b] NMDA | AMPA | KA |
|---|---|---|---|---|
| 1 | (triazole-CH2CH2-cyclohexyl-CH2-CH(NH)-CH2-CH(CO2H)) | 61.3 ± 3 | 6.0 ± 1.0 | 31.7 ± 4.4 |
| 2 | (triazole-CH2CH2-cyclohexyl-CH2-CH(NH)-CH2-CH(CO2H)) | >100 | <100 | |

TABLE III-continued

Antagonism of Cortical Wedge Depolarization by Racemic Formula I Compounds

| Compound | | IC$_{50}$ (µM)[b] | | |
|---|---|---|---|---|
| No. | Structure | NMDA | AMPA | KA |
| 4 | [structure] | >100 | 3.3 ± 0.9 | >100 |
| 5 | [structure] | >100 | 6.1 ± 1.5 | >100 |
| 6 | [structure] | | 22.0 ± 3.8 | |
| 7 | [structure] | >100 | 16.0 ± 1.4 | >100 |
| 8 | [structure] | >100 | 6.8 ± 1.5 | 18.1 ± 5.1 |
| 9 | [structure] | >100 | 32.2 ± 1.7 | >100 |
| 10 | [structure] | >100 | 27.6 ± 3.1 | |
| 11 | [structure] | 57 ± 4.4 | 42 ± 6.5 | >100 |
| 12 | [structure] | >100 | 31.4 ± 1.7 | 100 |

TABLE III-continued

Antagonism of Cortical Wedge Depolarization by Racemic Formula I Compounds

| Compound[a] | | IC$_{50}$ (μM)[b] | | |
|---|---|---|---|---|
| No. | Structure | NMDA | AMPA | KA |
| 13 | (structure) | >100 | 16.5 ± 2.7 | >100 |
| 14 | (structure) | >100 | 68.8 ± 12.3 | >100 |
| 15 | (structure) | >100 | 2.16 ± 0.79 | Ca. 10 |
| 19 | (structure) | 100 | 9.0 ± 2.8 | 23.6 ± 5.6 |
| 20 | (structure) | >100 | 100 | >100 |

[a]The compounds were tested as racemic mixtures with the relative stereochemistry as shown.
[b]Mean ± standard error (n = 3).

TABLE IV

Antagonism of Cortical Wedge Depolarization by Enantiopure Formula I Compounds

| Compound[a] | | IC$_{50}$ (μM)[b] | | |
|---|---|---|---|---|
| No. | Structure | NMDA | AMPA | KA |
| 21 | (structure) | <100 | 1.78 ± 0.23 | <100 |

TABLE IV-continued

Antagonism of Cortical Wedge Depolarization by Enantiopure Formula I Compounds

| Compound[a] | | $IC_{50}$ (μM)[b] | | |
|---|---|---|---|---|
| No. | Structure | NMDA | AMPA | KA |
| 22 | [structure] | >100 | 21.9 ± 3.3 | 28.9 ± 9.2 |
| 23 | [structure] | 22.9 ± 3.8 | 1.35 ± 0.35 | >31.6 |
| 24 | [structure] | >100 | 19.8 ± 2.2 | >31.6 |
| 25 | [structure] | >100 | 9.0 ± 0.8 | 29.1 ± 4.3 |

[a]The conpounds were tested as pure enantiomers with the relative and absolute stereochemistry as shown.
[b]Mean ± standard error (n = 3).

The data shows that the formula I compounds possess selective affinity for the AMPA ionotropic glutamate receptors. The radioligand binding assay is the preferred assay for discriminating between AMPA and KA selectivity. The formula I compounds, in particular compounds 1, 4, 5, 13, 15, 18, and 19, selectively displaced $^3$H-AMPA with $IC_{50}$ values less than 15 μM (Table I). The cortical wedge assay is the preferred assay for discriminating between AMPA and NMDA selectivity. This assay also distinguishes between agonist and antagonist activity. The formula I compounds, in particular compounds 1, 4, 5, 13, 15, and 19, are shown to be selective AMPA receptor antagonists (Table III). The data also shows that the formula I compounds wherein the stereochemistry at C-3 is S is preferred (Tables II and IV).

The compounds of the present invention are preferably formulated prior to administration. Therefore, another aspect of the present invention is a pharmaceutical formulation comprising a compound of formula I and a pharmaceutically-acceptable carrier, diluent, or excipient.

The present pharmaceutical formulations are prepared by known procedures using well-known and readily available ingredients. In making the compositions of the present invention, the active ingredient will usually be mixed with a carrier, or diluted by a carrier, or enclosed within a carrier which may be in the form of a capsule, sachet, paper, or other container. When the carrier serves as a diluent, it may be a solid, semi-solid, or liquid material which acts as a vehicle, excipient, or medium for the active ingredient. The compositions can be in the form of tablets, pills, powders, lozenges, sachets, cachets, elixirs, suspensions, emulsions, solutions, syrups, aerosols, ointments containing, for example up to 10% by weight of active compound, soft and hard gelatin capsules, suppositories, sterile injectable solutions, and sterile packaged powders.

Some examples of suitable carriers, excipients, and diluents include lactose, dextrose, sucrose, sorbitol, mannitol, starches, gum, acacia, calcium phosphate, alginates, tragacanth, gelatin, calcium silicate, microcrystalline cellulose, polyvinylpyrrolidone, cellulose, water syrup, methyl cellulose, methyl and propyl hydroxybenzoates, talc, magnesium sterate and mineral oil. The formulations can additionally include lubricating agents, wetting agents, emulsifying and suspending agents, preserving agents, sweetening agents, or flavoring agents. Compositions of the inventions may be formulated so as to provide quick, sustained, or delayed released of the active ingredient after administration to the patient by employing procedures well known in the art.

The compositions are preferably formulated in a unit dosage form, each dosage containing from about 5 to about 500 mg, more usually about 25 to about 300 mg of the active ingredient. The term "unit dosage form" refers to a physically discrete unit suitable as unitary dosages for human subjects and other mammals, each unit containing a predetermined quantity of active material calculated to produce the desired therapeutic effect, in association with a suitable pharmaceutical carrier. The following formulation examples are illustrative only and are not intended to limit the scope of the invention in any way.

Formulation 1
Hard gelatin capsules are prepared using the following ingredients:

| | Quantity (mg/capsule) |
|---|---|
| 6-[2-(1(2)H-Tetrazole-5-yl)-ethyl]decahydroisoquinoline-3-carboxylic acid | 250 |
| Starch, dried | 200 |
| Magnesium stearate | 10 |
| Total | 460 mg |

The above ingredients are mixed and filled into hard gelatin capsules in 460 mg quantities.

Formulation 2
A tablet is prepared using the ingredients below:

| | Quantity (mg/tablet) |
|---|---|
| 6-[2-(1(2)H-Tetrazole-5-yl)-2-thiaethyl]decahydro-isoquinoline-3-carboxylic acid | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3
An aerosol solution is prepared containing the following components:

| | Weight % |
|---|---|
| 6-[2-(3-Hydroxyisoxazol-5-yl)ethyl]decahydroisoquino-line-3-carboxylic acid | 0.25 |
| Ethanol | 29.75 |
| Propellant 22 | 70.00 |
| (chlorodifluoromethane) | |
| Total | 100.00 |

The active compound is mixed with ethanol and the mixture added to a portion of the Propellant 22, cooled to −30° C. and transferred to a filling device. The required amount is then fed to a stainless steel container and diluted with the remainder of the propellant. The valve units are then fitted to the container.

Formulation 4
Tablets each containing 60 mg of active ingredient are made as follows:

| | |
|---|---|
| 6-[(1(2-4)H-1,2,4-Triazole-5-yl)sulfonylmethyl]decahydro-isoquinoline-3-carboxylic acid | 60 mg |
| Starch | 45 mg |
| Microcrystalline cellulose | 35 mg |
| Polyvinylpyrrolidone | 4 mg |
| Sodium carboxymethyl starch | 4.5 mg |

Formulation 4
Tablets each containing 60 mg of active ingredient are made as follows:

| | |
|---|---|
| Magnesium stearate | 0.5 mg |
| Talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5
Capsules each containing 80 mg medicament are made as follows:

| | |
|---|---|
| 6-[2-(1(2)H-Tetrazole-5-yl)-1-methylethyl]decahydroisoquinoline-3-carboxylic acid | 80 mg |
| Starch | 59 mg |
| Microcrystalline cellulose | 59 mg |
| Magnesium stearate | 2 mg |
| Total | 200 mg |

The active ingredient, cellulose, starch and magnesium stearate are blended, passed through a No. 45 sieve, and filled into hard gelatin capsules in 200 mg quantities.

Formulation 6
Suppositories each containing 225 mg of active ingredient may be made as follows:

| | |
|---|---|
| 6-[2-(1(2)H-Tetrazole-5-yl)-1-phenylethyl]decahydro-isoquinoline-3-carboxylic acid | 225 mg |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7
Suspensions each containing 50 mg of medicament per 5 ml dose are made as follows:

| | |
|---|---|
| 6-[2-(1(2)H-Tetrazole-5-yl)-2-thiaethyl]decahydro-isoquinoline-3-carboxylic acid | 50 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

Formulation 8
An intravenous formulation may be prepared as follows:

| | |
|---|---|
| 6-[2-(3-Hydroxyisoxazol-5-yl)ethyl]decahydro-isoquinoline-3-carboxylic acid | 100 mg |
| Mannitol | 100 mg |
| 5 N Sodium hydroxide | 200 μl |
| Purified water to total | 5 ml |

The following Examples further illustrate the compounds of the present invention and the methods for their synthesis. The Examples are not intended to be limiting to the scope of the invention in any respect, and should not be so construed. All experiments were run under a positive pressure of dry nitrogen. Tetrahydrofuran (THF) was distilled from sodium prior to use. All other solvents and reagents were used as obtained. Proton nuclear magnetic resonance ($^1$H NMR) spectra were obtained on a GE QE-300 spectrometer at 300.15 MHz or a Bruker AM-500 spectrometer at 500 MHz. Where indicated, a small amount of 40% aqueous KOD was added to aid solution of NMR samples run in $D_2O$. Chromatographic separation on a Waters Prep 500 LC was generally carried out using a linear gradient of hexane to the solvent indicated in the text. The reactions were generally monitored for completion using thin layer chromatography (TLC). Thin layer chromatography was performed using E. Merck Kieselgel 60 $F_{254}$ plates, 5×10 cm, 0.25 mm thickness. Spots were detected using a combination of UV and chemical detection (plates dipped in a ceric ammonium molybdate solution [75 g of ammonium molybdate and 4 g of cerium (IV) sulfate in 500 mL of 10% aqueous sulfuric acid] and then heated on a hot plate). Flash chromatography was performed as described by Still, et al. Still, Kahn, and Mitra, *J. Org. Chem.*, 43, 2923 (1978). Elemental analyses for carbon, hydrogen and nitrogen were determined on a Control Equipment Corporation 440 Elemantal Analyzer. Melting points were determined in open glass capillaries on a Gallenkamp hot air bath melting point apparatus, and are uncorrected.

EXAMPLE 1

6-Hydroxytetrahydroisoquinoline-3-carboxylic Acid (V)

A slurry of d,l-m-tyrosine (1.91 kg) in dilute hydrochloric acid (76 ml of conc. HCl, 11.5 L of water) was heated to 55°–60° C., and treated with formaldehyde (1.18 L). Heating at 55°–70° C. was continued for 2 hours, then the reaction mixture was cooled to 3°–10° C. for 2 hours. The resulting mixture was filtered, and the filtrate washed with deionized water and acetone. The filter cake was dried in a vacuum oven at 55°–60° C. to give 1.88 kg of the title compound.

$^1$H NMR ($D_2O$/KOD): δ6.75 (d, 1H), 6.35 (d, 1H), 6.30 (s, 1H), 3.77 (d, 1H), 3.69 (d, 1H), 3.26 (dd, 1H), 2.79 (dd, 1H), 2.60 (dd, 1H).

Analysis calculated for $C_{10}H_{11}NO_3 \cdot 0.85\ H_2O$: C, 57.60; H, 6.13; N 6.71. Found: C, 57.70; H, 6.43; N, 6.69.

EXAMPLE 2

Ethyl 6-Hydroxy-2-methoxycarbonyltetrahydroisoquinoline-3-carboxylate (VI)

To a mixture of the compound from Example 1 (91.2 g) in ethanol (455 ml) was added concentrated sulfuric acid (27.5 ml) over a period of two minutes. After the initial exothermic reaction, the solution was heated at reflux for 16 hours. The resulting solution was cooled in an ice water bath, and a solution of potassium carbonate (130.5 g) in water (130.5 ml) was added. Methyl chloroformate (36.5 ml) was added to this solution at a rate such that the pH was greater than 6.9 and the temperature was less than 14° C. After an additional two hours, the reaction mixture was partitioned between ethyl acetate (250 ml) and water (500 ml). The layers were separated and the aqueous layer extracted with two portions of ethyl acetate (100 ml each). The organic layers were combined and concentrated in vacuo to give a solid residue. The residue was crystallized by dissolving in refluxing ethanol (180 ml), diluting the ethanol solution with water (360 ml), and stirring the resulting mixture at 4° C. for 24 hours. The crystalline solid was collected by filtration and dried in a vacuum oven (40° C., 23 hours) to give 93.9 g of the title compound.

$^1$H NMR ($CDCl_3$): δ6.95 (m, 1H), 6.67 (d, 1H), 6.61 (s, 1H), 5.76 (s, 1H), 5.06 and 4.85 (m, 1H), 4.65 (dd, 1H), 4.48 (d, 1h), 4.05 (m, 2H), 3.78 and 3.73 (s, 3H), 3.11 (m, 2H), 1.11 (t, 3H) (doubling due to amide rotamers).

Analysis calculated for $C_{14}H_{17}NO_5$: C, 60.21; H, 6.14; N, 5.02. Found: C, 60.49; H, 6.24; N, 4.98.

EXAMPLE 3

Ethyl 2-Methoxycarbonyl-6-oxodecahydroisoquinoline-3-carboxylate (VIII)

Alternative 1.

A. Preparation of Ethyl 6-Hydroxy-2-methoxycarbonyldecahydroisoquinoline-3-carboxylate (VII)

To a mixture of 3% rhodium on alumina (6.9 g) in ethyl acetate (350 ml) was added the compound from Example 2 (69.03 g). After sealing the vessel, the nitrogen atmosphere was replaced with hydrogen. The reaction was heated to 85° C. at a pressure of 100 psi for 23 hours. An additional portion of rhodium on alumina (1.4 g) was added and the heating resumed at elevated pressure for an additional two hours. The catalyst was removed by filtration, and the filtrate containing the title compound was used in the next step.

B. Preparation of Ethyl 2-Methoxycarbonyl-6-oxodecahydroisoquinoline-3-carboxylate (VIII)

To a solution of ruthenium(III) chloride (69 mg) in water (9.8 ml) was added the filtrate from Example 3A. The resulting two-phase mixture was cooled in an ice-water bath and treated with a solution of periodic acid (69 g) in water (26.9 ml). The periodic acid solution was added at a rate such that the temperature of the reaction mixture was less than 7.8° C. After the addition of the periodic acid, the ice bath was removed and the reaction mixture was allowed to warm to room temperature. After 1¼ hours, the aqueous phase was removed and the organic phase washed with two portions of water (50 ml each). The organic phase was concentrated to dryness in vacuo to give 67.7 g of the title compound as an oil.

Alternative 2.

Preparation of Ethyl 6-Hydroxy-2-methoxycarbonyldecahydroisoquinoline-3-carboxylate (VII) and Ethyl 2-Methoxycarbonyl-6-oxodecahydroisoquinoline-3-carboxylate (VIII)

A mixture of 3% rhodium on carbon (1.0 kg) and the compound from Example 2 (13.2 kg) in ethyl acetate (67 liters) was hydrogenated at a hydrogen pressure of 100 psi at about 85° C. After 23 hours, the reaction mixture was cooled to room temperature and the catalyst removed by filtration. The catalyst cake was washed with additional ethyl acetate (10 liters), and the ethyl acetate filtrates combined.

A sample of the ethyl acetate solution from the preceding paragraph was concentrated in vacuo to give 3.295 g of colorless oil, which is a mixture of C-6 ketone and C-6 alcohols. This mixture was separated by silica-gel flash chromatography, eluting with a linear gradient of methylene chloride to methylene chloride/ethyl acetate (9:1) followed by ethyl acetate, to give two products. The fractions containing the first product were combined and concentrated in vacuo to give 1.18 g of compound VIII. The fractions containing the second product were combined and concentrated in vacuo to give 1.36 g of compound VII.

EXAMPLE 4

(3S,4aS,8aR)-(−) Ethyl 2-Methoxycarbonyl-6-oxodecahydroisoquinoline-3-carboxylate ((−)-VIIIb)

A. Preparation of 2-Methoxycarbonyl-6-oxodecahydroisoquinoline-3-carboxylic Acid The compound from Example 3B (1.913 kg) was added to a 21% sodium ethoxide solution (509 g) in ethanol (8 L). The resulting solution was heated to reflux for a period of six hours, and then allowed to cool to room temperature over a period of 24 hours. This solution was treated with 5N sodium hydroxide solution (2.4 L) and allowed to remain at a temperature of about 25° C. to about 40° C. for a period of two hours. The reaction mixture was concentrated in vacuo to remove the ethanol. The residue was extracted with two portions of t-butylmethyl ether (5 L each), and the pH of the aqueous phase was adjusted to about 1.5 to about 2.5 by adding concentrated hydrochloride acid (1.7 L). The title compound was extracted from the aqueous solution with ethyl acetate (4×3 L). The combined ethyl acetate extracts were treated with FLORISIL (960 g) and sodium sulfate (960 g). The ethyl acetate filtrate containing the title compound was used in the next step without further purification.

B. Preparation of (3S,4aS,8aR)-(−)-2-Methoxycarbonyl-6-oxodecahydroisoquinoline-3-carboxylate α-methylbenzylamine salt To the ethyl acetate filtrate from Example 4A was added R-(+)-α-methylbenzylamine at a temperature of about 25° C. to about 30° C. over a period of one hour. The resultant slurry was allowed to remain at room temperature for a period of 24 hours, and then the precipitate was collected by filtration. The solid material was rinsed with several portions of ethyl acetate until the rinse was colorless. The filter cake was dried in a vacuum oven at a temperature of about 45°–50° C. This material was reslurried in 10 volumes of ethyl acetate at a temperature of about 45° C. to about 50° C. for about four hours, the solution was allowed to cool to ambient temperature, and the solid material removed by filtration. The solids were dried in vacuo at about 45° C. to about 50° C. to give 1.092 kg of the title compound.

$[\alpha]_D = -57.0°$ (c=1, $H_2O$).

Analysis calculated for $C_{20}H_{28}N_2O_5$: C, 63.81; H, 7.50; N, 7.44. Found: C, 63.87; H, 7.33; N, 7.33.

C. Preparation of (3S,4aS,8aR)-(−) Ethyl 2-Methoxycarbonyl-6-oxodecahydroisoquinoline-3-carboxylate ((−)-VIIIb)

A mixture of the compound from Example 4B (50 g) and acetonitrile (250 ml), was treated with triethylamine (26.8 g) and ethyl bromide (73 g). The resulting mixture was heated to reflux causing dissolution of the reactants. After about one to about two hours, the reaction was allowed to cool to room temperature and concentrated in vacuo. The residue was treated with ethyl acetate (250 ml). The resulting mixture was filtered and the solids rinsed with additional ethyl acetate. The filtrate was extracted with 3N hydrochloric acid, dried over $MgSO_4$, filtered, and concentrated in vacuo to give 34.9 g of the title compound.

$[\alpha]_D = -51.3°$ (c=1, $CH_2Cl_2$).

Analysis calculated for $C_{14}H_{21}NO_5$: C, 59.35; H, 7.47; N, 4.94. Found: C, 59.11; H, 7.20; N, 4.90.

D. Preparation of (3R,4aR,8aS)-(+) Ethyl 2-Methoxycarbonyl-6-oxodecahydroisoquinoline-3-carboxylate ((+)-VIIIb)

The title compound was prepared from the racemic mixture from Example 4A using the procedures described in Examples 4B and 4C with S-α-methylbenzylamine.

EXAMPLE 5

(3SR,4aSR,8aRS) Ethyl 2-Methoxycarbonyl -6-oxodecahydroisoquinoline-3-carboxylate ((±)-VIIIb)

A. Preparation of Ethyl 6-Hydroxy-2-methoxycarbonyldecahydroisoquinoline-3-carboxylate A mixture of the compound from Example 2 (158.9 g) and 5% ruthenium on alumina (80 g) in ethanol (1760 ml) was hydrogenated at a pressure of 2000 psi. After 16 hours at about 180° C., the cooled reaction mixture was filtered through CELITE, and the filtrate concentrated in vacuo. The residue was diluted with ethyl acetate. This mixture was filtered through CELITE, and concentrated in vacuo to give 156.7 g of the title compound.

B. Preparation of Ethyl 2-Methoxycarbonyl-6-oxodecahydroisoquinoline-3-carboxylate (VIII)

A solution of the compound from Example 5A (156.7 g) in methylene chloride (300 ml) was added to a mixture of pyridinium chlorochromate (260.5 g) and powdered 4 Å molecular sieves in methylene chloride (1400 ml), which was allowed to stir one hour prior to the addition of the alcohol. After two hours, the reaction mixture was diluted with ether and filtered through a layer each of CELITE and silica gel. The solids were washed with ether, and the combined ether solutions concentrated in vacuo. The residue was dissolved in ether, filtered through CELITE and silica gel, and the filtrate concentrated in vacuo to give 128.8 g of a mixture of VIIIa and VIIIb (VIIIa:VIIIb=78:22).

C. Preparation of (3SR,4aSR,8aRS)-(±) Ethyl 2-Methoxycarbonyl-6-oxodecahydroisoquinoline-3-carboxylate (VIIIb)

A solution of the mixture from Example 5B (128.8 g) in ethanol (1000 ml) was treated with a solution of sodium hydride (1.82 g) in ethanol (100 ml), and the resulting mixture heated to reflux. After 1½ hours, the mixture was allowed to cool to room temperature and concentrated in vacuo. The residue was dissolved in methylene chloride/ether (1:1), and washed with 10% aqueous sodium bisulfate. The aqueous phase was extracted with ether, the organic phases combined, dried over magnesium sulfate, filtered, and concentrated in vacuo. The residue was purified by silica-gel chromatography on a WATERS PREP 500 LC, eluting with a linear gradient of hexane to 25% ethyl acetate/hexane, to give 106.9 g of a mixture of VIIIa and VIIIb (VIIIa:VIIIb=13:87). Recrystallization of this mixture from ether then gave 67.0 g of the title compound. Melting point 78°–79° C.

$^1H$ NMR (DMSO) δ: 4.76 (d, 1H), 4.124 (q, 2H), 3.80 (d, 1H), 3.61 (s, 3H), 3.21 (bd, 1H), 2.65 (dd, 1H), 2.43 (dt, 1H), 2.19 (m, 1H), 2.14 (m, 2H), 1.98 (ddd, 1H), 1.85 (m, 1H), 1.75 (m, 1H), 1.65 (dt, 1H), 1.20 (t, 3H).

Analysis calculated for $C_{14}H_{21}NO_5$: C, 59.35; H, 7.47; N, 4.94. Found: C, 59.62; H, 7.61; N, 4.97.

EXAMPLE 6

(3SR,4aRS,6RS,8aRS)-6-(2-Carboxyethyl)-decahydroisoquinoline-3-carboxylic Acid (11)

A. Preparation of Ethyl 2-Methoxycarbonyl-6-(methoxymethylene)decahydroisoquinoline-3-carboxylate To a suspension of (methoxymethyl)triphenylphosphonium chloride (37.8 g), previously washed with THF and pentane, then dried in vacuo at room temperature, in tetrahydrofuran (150 ml) at a temperature of 0° C. was added a 1M solution of sodium bis(trimethylsilyl)amide in THF (100 ml). After 30 minutes this solution was added to a solution of the compound from Example 5C (20.2 g) in THF (100 ml) at a temperature of about 0° C. The reaction solution was quenched by the addition of water (150 ml). The resultant solution was diluted with ether (150 ml), and the organic phase separated and washed with water (150 ml). The combined aqueous phases were extracted with ether (2×150 ml). The combined organic solutions were washed with brine, dried over magnesium sulfate, filtered, and concentrated in vacuo to dryness. The residue was suspended in ethyl acetate/hexane (1:1), and the resulting suspension stirred at room temperature for ten minutes, filtered, and the filtrate concentrated in vacuo. The solid material was suspended in additional ethyl acetate/hexane (1:1), stirred at room temperature, and filtered. The ethyl acetate/hexane filtrates were combined and concentrated in vacuo. The product was purified by silica-gel chromatography on a WATERS PREP 500 LC, using an 8-L gradient of hexane to 25% ethyl acetate/hexane, to give 20.9 g of the title compound.

B. Preparation of Ethyl 6-(Ethyl 2-carboxyethenyl)-2-methoxycarbonyldecahydroisoquinoline-3-carboxylate The compound from Example 6A (3.33 g) was added to a mixture of THF (58 ml) and 1N hydrochloric acid (85 ml). After four hours, the solution was partitioned between methylene chloride (125 ml) and water (100 ml). The organic phase was removed and the aqueous extracted with additional methylene chloride (2×65 ml). The combined organic solutions were washed with saturated sodium bicarbonate (50 ml), dried over magnesium sulfate, filtered, and concentrated in vacuo. The residue was dissolved in THF (10 ml) and used in the following paragraph without further purification.

To a suspension of sodium hydride (0.6 g), previously washed with hexane, in THF (20 ml) was added triethylphosphonoacetate (3.36 g). After 30 minutes at room temperature, this mixture was treated with the THF solution from the preceding paragraph. After an additional half hour at room temperature, the reaction was treated sequentially with water (25 ml) and ether. The organic phase was removed and the aqueous extracted with ether (2 times). The combined organic extracts were dried over magnesium sulfate, filtered, and concentrated in vacuo. The residue was used in the next step without further purification.

C. Preparation of Ethyl 6-(Ethyl 2-carboxyethyl)-2-methoxycarbonyldecahydroisoquinoline-3-carboxylate A mixture of the compound from Example 6B (3.9 g) and 5% palladium on carbon (1.0 g) in ethanol (96 ml) was hydrogenated at a hydrogen pressure of 60 psi at room temperature. After three hours, the mixture was filtered through CELITE, the CELITE filter cake washed with ether, and the combined filtrates concentrated in vacuo. The residue was purified by chromatography on a LOBAR C column, eluting with 25% ethyl acetate/hexane, to give fractions containing diastereomers, 3SR,4aRS,6RS,8aRS (third fraction) and 3SR,4aRS,6SR,8aRS (first fraction), and a mixture thereof (second fraction). The total yield of the title compound was 3.22 g.

D. Preparation of (3SR,4aRS,6RS,8aRS)-6-(2-Carboxyethyl)decahydroisoquinoline-3-carboxylic Acid The 3SR,4aRS,6RS,8aRS isomer from Example 6C was added to 6N hydrochloric acid (50 ml), and the resulting mixture was heated to reflux overnight. The reaction mixture was allowed to cool to room temperature and then concentrated in vacuo. The residue was purified by ion-exchange chromatography on DOWEX 50X8 (100–200 mesh), eluting with 10% pyridine/water, to give 0.63 g of title compound. Melting point 190°–191° C.

Analysis calculated for $C_{13}H_{21}O_4 \cdot H_2O$: C, 57.12; H, 8.48; N, 5.12. Found: C, 57.14; H, 8.30; N, 5.07.

EXAMPLE 7

(3SR,4aRS,6SR,8aRS)-6-[2-(1(2)H-Tetrazole-5-yl)-2-thiaethyl]decahydroisoquinoline-3-carboxylic Acid (4) and (3SR,4aRS,6RS,8aRS)-6-[2-(1(2)H-Tetrazole-5-yl)-2-thiaethyl]decahydroisoquinoline-3-carboxylic Acid (5)

A. Preparation of Ethyl 6-Formyl-2-methoxycarbonyldecahydroisoquinoline-3-carboxylate A solution of the compound from Example 6A (11.1 g) in THF (125 ml) was treated with 1N hydrochloric acid (160 ml). After 4¾ hours, the reaction mixture was diluted with water (100 ml), and extracted with ether (3 times). The organic extracts were combined, washed with saturated sodium bicarbonate, dried over magnesium sulfate, filtered, and concentrated in vacuo. This material was used immediately in the next step without further purification.

B. Preparation of Ethyl 6-Hydroxymethyl-2-methoxycarbonyldecahydroisoquinoline-3-carboxylate A solution of the compound from Example 7A (10.62 g) in ethanol (108 ml) was cooled to 0° C. and treated with sodium borohydride (1.34 g). After ten minutes, the solution was concentrated in vacuo. The residue was partitioned between 10% sodium bisulfate and methylene chloride. The organic phase was removed and the aqueous phase extracted with additional methylene chloride (3 times). The organic extracts were combined, dried over magnesium sulfate, filtered, and concentrated in vacuo. The residue was used in the next step without further purification.

C. Preparation of Ethyl 6-Bromomethyl-2-methoxycarbonyldecahydroisoquinoline-3-carboxylate A solution of triphenylphosphine (14.05 g) in methylene chloride (225 ml) was treated with bromine until the yellow color persisted (approximately 8.56 g). Additional triphenylphosphine was added until the solution became colorless. This solution was treated with a solution of the compound from Example 7B (10.69 g) and pyridine (5.65 g) in methylene chloride (185 ml). After two hours at room temperature, the reaction mixture was extracted with 10% sodium bisulfate. The aqueous extract was extracted with ether (3 times). The ether extracts were combined with the organic phase, dried over magnesium sulfate, filtered, and concentrated in vacuo. The residue was treated with ether and the precipitated triphenylphosphine oxide removed by filtration. The filtrate was concentrated in vacuo and the residue taken up in additional ether to precipitate the remaining traces of triphenylphosphine oxide. The mixture was filtered and the filtrate concentrated in vacuo. The residue was purified by silica-gel chromatography on a WATERS PREP 500 LC, etuting with a 8-L gradient of 10% ethyl acetate/hexane to 30% ethyl acetate/hexane, to give fractions containing the diastereomers, 3SR,4aRS,6SR,8aRS (third fraction) and 3SR,4aRS,6RS,8aRS (first fraction), and a mixture thereof (second fraction). The total yield of the title compound was 10.73 g.

D. Preparation of (3SR,4aRS,6SR,8aRS) Ethyl 6-[2-(1(2)H-Tetrazole-5-yl)-2-thiaethyl]-2-methoxycarbonyldecahydroisoquinoline-3-carboxylate A solution of the 3SR,4aRS,6SR,8aRS isomer from Example 7C (8.33 g), thiotetrazole (2.58 g), and triethylamine (4.65 g) in anhydrous acetonitrile (70 ml) was heated to 80° C. After 20 hours, the reaction solution was partitioned between ethyl acetate and 10% sodium bisulfate. The phases were separated and the aqueous phase extracted with additional ethyl acetate (3 times). The ethyl acetate extracts were combined, dried over magnesium sulfate, filtered, and concentrated in vacuo. The residue was purified by silica-gel flash chromatography, eluting with acetic acid/ethyl acetate/toluene (4:36:60). The fractions containing the title compound were combined and concentrated in vacuo. The residue was diluted with methanol and concentrated in vacuo, then diluted with chloroform and concentrated in vacuo, to give 8.91 g of the title compound.

E. Preparation of (3SR,4aRS,6SR,8aRS)-6-[2-(1(2)H-Tetrazole-5-yl)-2-thiaethyl]decahydroisoquinoline-3-carboxylic Acid A solution of the compound from Example 7D (8.91 g) in 6N hydrochloric acid (100 ml) was heated to 90° C. for three hours. The solution was allowed to cool to room temperature, filtered, and the filter cake washed with water and acetone. The solids were dried in vacuo at room temperature for about 18 hours, to give 5.36 g of the title compound as the hydrochloride salt. Melting point 285° C.

Analysis calculated for $C_{12}H_{19}N_5O_2S \cdot HCl$: C, 43.71; H, 6.09; N, 20.98. Found: C, 43.43; H, 6.17; N, 20.77.

F. Preparation of (3SR,4aRS,6RS,8aRS)-6-[1(2)H-Tetrazole-5-ylthiamethyl]decahydroisoquinoline-3-carboxylic Acid The 3SR,4aRS,6RS,8aRS isomer from Example 7C was converted to the title compound in a manner as described in Examples 7D and 7E. The title compound was purified by ion-exchange chromatography on DOWEX 50X8, eluting with 10% pyridine/water. Melting point 257° C.

Analysis calculated for $C_{12}H_{19}N_5O_2S$: C, 48.46; H, 6.44; N, 23.55; S, 10.78. Found: C, 48.21; H, 6.55; N, 23.25; S, 11.08.

EXAMPLE 8

3SR,4aRS,6RS,8aRS)-6-[3-(1(2)H-Tetrazole-5-yl)-3-thiaprop-1-yl]decahydroisoquinoline-3-carboxylic Acid (8) and 3SR,4aRS,6SR,8aRS)-e-[3-(1(2)H-Tetrazole-5-yl)-3-thiaprop-1-yl]decahydroisoquinoline-3-carboxylic Acid A. Preparation of Ethyl 6-(Benzyloxycarbonylmethylene)-2-methoxycarbonyldecahydroisoquinoline-3-carboxylate A suspension of sodium hydride (3.11 g), previously washed in hexane, in tetrahydrofuran (200 ml) was treated with a solution of benzyl diethylphosphonoacetate (22.2 g) in tetrahydrofuran (50 ml). After 30 minutes, the resulting clear solution was treated with a solution of the compound from Example 5C (20 g) in tetrahydrofuran (80 ml). After five hours at room temperature, the reaction solution was treated with water (100 ml) and brine (100 ml). The organic phase was removed and the aqueous extracted with ether (2×100 ml). The organic phases were combined, washed with brine, dried over magnesium sulfate, filtered, and concentrated in vacuo. The residue was purified by silica-gel chromatography on a WATERS PREP 500 LC, eluting with an 8-L gradient of hexane to 50% ethyl acetate/hexane, to give 26.3 g of the title compound.

B. Preparation of Ethyl 6-Carboxymethyl-2-methoxycarbonyldecahydroisoquinoline-3-carboxylic Acid A mixture of the compound from Example 8A (26.15 g) and 5% palladium on carbon (5 g) in ethyl acetate (270 ml) was hydrogenated at a hydrogen pressure of 60 psi at room temperature. After four hours, the catalyst was removed by filtration and the filtrate concentrated in vacuo. The residue (20.5 g) was used in the next step without further purification.

C. Preparation of Ethyl 6-(2-Hydroxyethyl)-2-methoxycarbonyldecahydroisoquinoline-3-carboxylate A solution of the compound from 8B (20.5 g) in tetrahydrofuran (200 ml) at a temperature of 0° C. was treated with a 2M solution of borane-methyl sulfide in tetrahydrofuran (61 ml). After four hours, this solution was carefully treated with a saturated sodium bicarbonate solution. The resulting mixture was extracted with ether (300 ml), and the ether extract washed with saturated sodium chloride. The sodium bicarbonate solution was extracted with ether (3 times). The ether extracts were combined, dried over magnesium sulfate, filtered, and concentrated in vacuo, to give 19.34 g of the title compound as oil. This compound was used in the next step without further purification.

D. Preparation of Ethyl 6-(2-Bromoethyl)-2-methoxycarbonyldecahydroisoquinoiine-3-carboxylate A solution of triphenylphosphine (24.3 g) in methylene chloride (300 ml) was cooled to 0° C. and treated with bromine (14.9 g). Additional triphenylphosphine was added until the solution became colorless. This solution was treated with a solution of the compound from Example 8C (19.34 g) and pyridine (9.76 g) in methylene chloride (225 ml). After 15 minutes at 0° C., the reaction solution was extracted with 10% sodium bisulfate (2 times). Additional water was added to dissolve a precipitate which had formed, then the aqueous washed with ether (2 times). The organic phases were combined, dried over magnesium sulfate, filtered, and concentrated in vacuo. The residue was diluted with ether and the triphenylphosphine oxide precipitate removed by filtration. This procedure was repeated two times. The residue was purified by silica-gel chromatography on WATERS PREP 500 LC, eluting with a linear gradient of hexane to 30% ethyl acetate/hexane, to give fractions containing the diastereomers, 3SR,4aRS,6RS,8aRS (first fraction) and 3SR,4aRS,6SR,8aRS (third fraction), and a mixture thereof (second fraction). The fractions containing the 3SR,4aRS, 6RS,8aRS isomer were combined and concentrated in vacuo to give 3.71 g. The fractions containing the 3SR,4aRS,6SR, 8aRS isomer were combined and concentrated in vacuo to give 5.27 g.

E. Preparation of (3SR,4aRS,6SR,8aRS) Ethyl 6-[3-(1(2)H-tetrazole-5-yl)-3-thiaprop-1-yl]-2-methoxycarbonyldecahydroisoquinoline-3-carboxylate A solution of the 3SR,4aRS,6SR,8aRS isomer from Example 8D (2.0 g), thiotetrazole (0.6 g), and triethylamine (1.5 ml) in acetonitrile (18 ml) was heated to 85° C. for a period of about 18 hours. Additional thiotetrazole (0.12 g) and triethylamine (0.2 ml) were added to the reaction solution with continued heating. After four hours, the reaction solution was allowed to cool and worked up as in Example 7D. The residue was purified by silica-gel flash chromatography, eluting with acetic acid/ethyl acetate/hexane (4:36:60), to give 2.05 g of the title compound.

F. Preparation of (3SR,4aRS,6SR,8aRS) 6-[3-(1(2)H-Tetrazole-5-yl)-3-thiaprop-1-yl]-decahydroisoquinoline-3-carboxylic Acid A solution of the compound from Example 8E (1.9 g) in 6N hydrochloric acid (25 ml) was heated to reflux for about 18 hours. The solution was allowed to cool to room temperature and concentrated in vacuo. The residue was purified by ion-exchange chromatography on DOWEX 50X8-100, eluting with 10% pyridine/water. The fractions containing the title compound were combined and concentrated in vacuo. The residue was diluted with water, which caused the title compound to crystallize. The crystalline material was removed by filtration and the filter cake washed with water, acetone, and ether. The mother liquor was concentrated in vacuo, and the residue subjected to a similar procedure to produce a second crop of crystals. The crystalline material was combined and dried at 60° C. in vacuo, to give 0.94 g of the title compound. Melting point 185° C.

Analysis calculated for $C_{13}H_{21}N_5O_2S \cdot 0.5H_2O \cdot 0.25C_3H_6O$: C, 49.30; H, 7.07; N, 20.90. Found: C, 49.48; H, 6.98; N, 21.25.

G. Preparation of (3SR,4aRS,6RS,8aRS) 6-[3-(1(2)H-Tetrazole-5-yl)-3-thiaprop-1-yl]decahydroisoquinoline-3-carboxylic Acid The 3SR,4aRS,6RS,8aRS isomer from Example 8D was converted to the title compound using procedures similar to those described in Examples 8E and F. Melting point 201° C.

Analysis calculated for $C_{13}H_{21}N_5O_2S \cdot 0.8H_2O$: C, 47.92; H, 6.99; N, 21.49. Found: C, 47.95; H, 6.91; N, 21.47.

EXAMPLE 9

(3SR,4aRS,6SR,8aRS)-6-[N-(1(2)H-Tetrazole-5-yl)methylformamido]-decahydroisoquinoline-3-carboxylic Acid (3)

A. Preparation of (3SR,4aRS,6SR,8aRS) Ethyl 6-(Cyanomethyl)amino-2-methoxycarbonyldecahydroisoquinoline-3-carboxylate A solution of the compound from Example 5C (8.0 g) and aminoacetonitrile hydrochloride (25.15 g) in ethanol (100 ml) was treated with powdered 4 Å molecular sieves (8.0 g) at room temperature. After 20 minutes, the mixture was treated with sodium cyanoborohydride (1.7 g). After an additional 18 hours at room temperature, the reaction mixture was filtered through CELITE, and the solids washed with ethanol. The filtrate was concentrated in vacuo. The residue was dissolved in methylene chloride and the methylene chloride solution washed with 15% sodium hydroxide. The phases were separated and the aqueous extracted with methylene chloride and ether (2 times). The organic extracts were combined, washed with water and brine, dried over magnesium sulfate, filtered, and concentrated in vacuo. The residue was purified by silica-gel flash chromatography, eluting with ethyl acetate/hexane/methanol (50:49:1), to give 7.0 g of the title compound.

B. Preparation of (3SR,4aRS,6SR,8aRS) Ethyl 6-[N-(Cyanomethyl)formamido]-2-methoxycarbonyldecahydroisoquinoline-3-carboxylate A solution of the compound from Example 9A (1.5 g) in dry THF (100 ml) was treated with formic acetic anhydride (1.3 g). After one hour at room temperature, the reaction solution was concentrated in vacuo. The residue was partitioned between water and ethyl acetate. The phases were separated, and the organic phase dried over sodium sulfate, filtered, and concentrated in vacuo. The residue was dissolved in ethyl acetate and concentrated in vacuo. This procedure was repeated four times. The residue was purified by silica-gel flash chromatography, eluting with methanol/hexane/ethyl acetate (2:23:75), to give 1.0 g of title compound.

C. Preparation of (3SR,4aRS,6SR,8aRS) Ethyl 6-[N-(1(2)H-Tetrazole-5-yl)methylformamido]-2-methoxycarbonyldecahydroisoquinoline-3-carboxylate A mixture of the compound from Example 9B and tributyltin azide (10 ml) was heated to 80° C. After four days, additional tributyltin azide (3 ml) was added to the reaction mixture. After an additional three days, the reaction mixture was allowed to cool to room temperature and diluted with ether (100 ml). This solution was treated with gaseous hydrogen chloride to produce a white solid. The mixture was diluted with acetonitrile (100 ml) and extracted with hexane (five times). The acetonitrile phase was concentrated in vacuo to give the title compound as a white solid.

D. Preparation of (3SR,4aRS,6SR,8aRS)-6-[N-(1(2)H-Tetrazole-5-yl)methylformamido]-2-carboxymethoxycarbonyldecahydroisoquinoline-3-carboxylic Acid A solution of the compound from Example 9C (1 g) in ethanol (50 ml) was treated with 1N sodium hydroxide (2.75 ml). After about 18 hours, the reaction mixture was concentrated in vacuo. The residue was dissolved in ethyl acetate with the addition of ethanol (1 ml), then hexane was added until the solution became cloudy. The resulting solution was placed in a freezer for four hours. The liquid was removed and the crystalline material rinsed with hexane (three times). The crystalline material was dissolved in acetone and concentrated in vacuo. The residue was dissolved in ethanol (20 ml) and treated with 1N sodium hydroxide (5 ml). After about 18 hours, the pH of the solution was adjusted to pH 4.0 and the resulting mixture partitioned between ethyl acetate and water. The phases were separated and the aqueous extracted with ethyl acetate (three times). The aqueous layer was concentrated in vacuo to give the title compound.

E. Preparation of (3SR,4aRS,6SR,8aRS)-6-[N-(1(2)H-Tetrazole-5-yl)methylformamido]decahydroisoquinoline-3-carboxylic Acid A solution of the compound from Example 9D in chloroform (10 ml) was treated with trimethylsilyl iodide (1.1 ml), and the resulting solution heated to reflux. After two hours, the reaction mixture was allowed to cool to room temperature. This mixture was partitioned between water and ether. The phases were separated and the aqueous extracted with ether (three times), then concentrated in vacuo. The residue was purified by ion-exchange chromatography on DOWEX 50X8, eluting with 10% pyridine/water, to give 110 mg of the title compound. Melting point 117°–122° C.

Analysis calculated for $C_{13}H_{20}N_6O_3 \cdot 1.3H_2O$: C, 47.06; H, 6.86; N, 25.33. Found: C, 46.63; H, 6.71; N, 25.98.

EXAMPLE 10

(3SR,4aRS,6SR,8aRS)-6-[(1(2)H-Tetrazole-5-yl)prop-1-yl]decahydroisoquinoline-3-carboxylic Acid (6)

A. Preparation of Ethyl 6-Methylidine-2-methoxycarbonyldecahydroisoquinoline-3-carboxylate Methyltriphenylphosphonium bromide (76.3 g) was added to THF (800 ml). This mixture was stirred at room temperature for 15 minutes, then filtered. The filtrate was concentrated to dryness in vacuo at about 50° C. for 30 minutes. The residue was suspended in THF (220 ml) and the resulting mixture cooled to 0° C. The cold mixture was treated with a 1M solution of sodium bis(trimethylsilyl) amide in THF (213.6 ml). After 15 minutes, the resulting solution was added to a cold (0° C.) solution of the racemic compound from Example 5C (43.23 g) in THF (320 ml) until a pale yellow color persisted. The reaction mixture was treated with water (250 ml) and ether (500 ml), and the phases separated. The organic phase was extracted with water (10 ml), and the aqueous phase extracted with ether (2 times). The organic phases were combined, dried, and concentrated in vacuo. The residue was suspended in 25% ethyl acetate/hexane and the resulting mixture stirred at room temperature. After one hour, the mixture was filtered and the solids rinsed with 25% ethyl acetate/hexane. The filtrate was concentrated in vacuo. The residue was purified by silica-gel flash chromatography, eluting with 25% ethyl acetate/hexane, to give 40.67 g of the title compound.

B. Preparation of (3SR,4aRS,6RS,8aRS) Ethyl 6-Hydroxymethyl-2-methoxycarbonyldecahydroisoquinoline-3-carboxylate A cold (0° C.) solution of the compound from Example 10A (40.67 g) in THF (285 ml) was treated with a 10M solution of borane-methyl sulfide (9.7 ml). After two hours at 0° C., the reaction was allowed to warm to room temperature. After an additional 2½ hours, the reaction mixture was cooled to 0° C. and treated with ethanol (25 ml), 3N sodium hydroxide (200 ml), and 30% hydrogen peroxide (200 ml). After 30 minutes at 0° C., the reaction mixture was allowed to warm to room temperature. After an additional two hours at room temperature, this mixture was extracted with ether (3 times). The combined organic extracts were dried over magnesium sulfate, filtered, and concentrated in vacuo. The residue was purified by silica-gel chromatography on a WATERS PREP 500 LC, eluting with a gradient of hexane to 60% ethyl acetate/hexane, to give 40.36 g of the title compound.

C. Preparation of (3SR,4aRS,6RS,8aRS) Ethyl 6-Formyl-2-methoxycarbonyldecahydroisoquinoline-3-carboxylate A solution of dimethylsulfoxide (22.1 ml) in methylene chloride (250 ml) was cooled to −78° C. and treated with oxalyl chloride (13.05 ml). After five minutes, this cold solution was treated with a solution of the compound from Example 10B (37.34 g) in methylene chloride (150 ml). After an additional 15 minutes, this mixture was treated with triethylamine (86.9 ml). After an additional 45 minutes at −78° C., the reaction mixture was allowed to warm to room temperature and treated with 10% sodium bisulfate (500 ml) and ether (500 ml). The phases were separated and the aqueous extracted with ether (2 times). The organic phases were combined, dried over magnesium sulfate, filtered, and concentrated in vacuo. The residue was used in the next step without further purification.

D. Preparation of (3SR,4aRS,6RS,8aRS) Ethyl 6-(Benzyl 2-carboxyethylene)-2-methoxycarbonyldecahydroisoquinoline-3-carboxylate To a suspension of sodium hydride (1.13 g), previously washed with hexane, in THF (50 ml) was added benzyl diethylphosphonoacetate (1.8 g). After 15 minutes at room temperature, this mixture was cooled to about 0° C. The cooled mixture was treated with a solution of the compound from Example 10C (5.60 g) in tetrahydrofuran (25 ml). After an additional 15 minutes, the reaction mixture was allowed to warm to room temperature. This mixture was treated with water and ether. The organic phase was removed and the aqueous extracted with ether (two times). The combined organic extracts were dried over magnesium sulfate, filtered, and concentrated in vacuo. The residue was purified by silica-gel flash chromatography, eluting with 35% ethyl acetate/hexane, to give 7.35 g of the title compound.

E. Preparation of (3SR,4aRS,6RS,8aRS) Ethyl 6-(2-Carboxyethyl)-2-methoxycarbonyldecahydroisoquinoline-3-carboxylate A mixture of the compound from Example 10D (7.21 g) and 5% palladium on carbon (2.5 g) in ethyl acetate was hydrogenated at a hydrogen pressure of 60 psi at room temperature. After four hours, the mixture was filtered through CELITE, and the filtrate concentrated in vacuo to give 6.18 g of a mixture of the title compound and starting material. This mixture was subjected to a second hydrogenation to give the title compound. This material was used in the next step without further purification.

F. Preparation of (3SR,4aRS,6SR,8aRS) Ethyl 6-(3-Hydroxyprop-1-yl)-2-methoxycarbonyldecahydroisoquinoline-3-carboxylate A solution of the compound from Example 10E (5.7 g) in THF (40 ml) was treated with a 2M solution of boranemethyl sulfide in THF (17 ml). After three hours at a temperature of 0° C., this solution was treated with water. The work up was similar to that described in Example 8C. The residue was purified by silica-gel flash chromatography, eluting with 50% ethyl acetate/hexane, to give 3.71 g of the title compound.

G. Preparation of (3SR,4aRS,6SR,8aRS) Ethyl 6-(3-Cyanoprop-1-yl)-2-methoxycarbonyldecahydroisoquinoline-3-carboxylate A solution of triphenylphosphine (3.15 g) in methylene chloride (10 ml) was cooled to 0° C. and treated with bromine (1.92 g). Additional triphenylphosphine was added until this solution became colorless. This solution was treated with a solution of the compound from Example 10F (1.96 g) and pyridine (1.5 ml) in methylene chloride (10 ml). The reaction mixture was allowed to warm to room temperature. After 2 hours at room temperature, the reaction solution was extracted with 10% sodium bisulfate (two times). Additional water was added to dissolve a precipitate which had formed, then the combined aqueous phases were washed with ether. The organic phases were combined, dried over magnesium sulfate, filtered, and concentrated in vacuo. The residue was diluted with ether and the triphenylphosphine oxide precipitate removed by filtration. This procedure was repeated two times.

A solution of the product from the preceding paragraph and sodium cyanide (0.59 g) in dimethylsulfoxide (10 ml) was heated to 60° C. After two hours, the solution was allowed to cool to room temperature and treated with a 50% solution of brine (50 ml). The resulting mixture was extracted with methylene chloride (five times) and with ether. The combined organic extracts were dried over magnesium sulfate, filtered, and concentrated in vacuo. The residue was purified by silica-gel flash chromatography, eluting with 50% ethyl acetate/hexane, to give 1.72 g of the title compound.

H. Preparation of (3SR,4aRS,6SR,8aRS)-6-[(1(2)H-Tetrazole-5-yl)prop-1-yl]decahydroisoquinoline-3-carboxylic Acid A mixture of the compound from Example 10G (1.62 g) and tributyltin azide (4.1 g) was heated to 90° C. After three days, this mixture was treated with 6N hydrochloric acid (50 ml) and the resulting mixture heated at 100° C. After about 18 hours, the reaction mixture was allowed to cool to room temperature and extracted with methylene chloride and ether. The aqueous phase was concentrated in vacuo. The residue was purified by ion exchange chromatography on DOWEX 50X8-100, eluting with 10% pyridine/water, to give 390 mg of the title compound. Melting point 207° C.

Analysis calculated for $C_{14}H_{23}N_5O_2 \cdot 0.75\ H_2O$: C, 54.79; H, 8.05; N, 22.82. Found: C, 55.08; H, 7.85; N, 22.86.

EXAMPLE 11

(3SR,4aRS,6SR,a8RS)-6-[(1(2)H-Tetrazole-5-yl)
methoxymethyl]decahydroisoquinoline-3
-carboxylic Acid (7)

A. Preparation of Ethyl 6-Hydroxymethyl-2-methoxycarbonyldecahydroisoquinoline-3-carboxylate A solution of the compound from Example 6A (20 g) in 1N hydrochloric acid (85 ml) and acetonitrile (335 ml) was allowed to stand at room temperature. After 45 hours, the reaction was partitioned between ether (1 L) and saturated sodium bicarbonate (200 ml). The phases were separated and the aqueous extracted with ether (3×80 ml). The organic phases were combined, dried, filtered, and concentrated in vacuo.

A solution of the residue from the preceding paragraph in ethanol (170 ml) was cooled to 0° C. The cooled solution was treated with sodium borohydride (2.4 g). After ten minutes, the reaction solution was concentrated in vacuo. The residue was partitioned between saturated sodium bicarbonate and methylene chloride. The organic phase was dried, filtered, and concentrated in vacuo to give the title compound as an oil. This material was used in this next step without further purification.

B. Preparation of (3SR,4aRS,6SR,8aRS) and (3SR,4aRS,6RS,8aRS) Ethyl 6-(Cyanomethoxy)methyl-2-methoxycarbonyl-decahydroisoquinoline-3-carboxylate A solution of the compound from Example 11A (4.79 g) and N,N-diisopropylethylamine (5.2 g) in methylene chloride. (50 ml) was cooled to 0° C. and treated with chloromethyl methyl ether (1.54 g). The reaction mixture was kept at a temperature of about 0° C. for 30 minutes, then the reaction mixture was allowed to warm to room temperature. After about three hours, additional chloromethyl methyl ether (0.5 ml) was added to the reaction. After about 18 hours, the reaction was treated with 10% sodium bisulfate. The phases were separated and the aqueous phase extracted with ether (2 times). The organic phases were combined, dried, filtered, and concentrated in vacuo. The residual oil was dissolved in methylene chloride (50 ml), and the resulting solution treated trimethylsilyl cyanide (9.63 ml). This solution was cooled to 0° C. and treated with boron trifluoride etherate (5.92 ml). The resulting solution was allowed to warm to room temperature. After one hour at room temperature, the reaction mixture was treated with 10% potassium carbonate (100 ml). The phases were separated and the aqueous phase extracted with methylene chloride (2 times) and ether. The organic phases were combined, washed with saturated sodium bicarbonate, dried, filtered, and concentrated in vacuo. The residue was purified by silica-gel flash chromatography, eluting with 35% ethyl acetate/hexane, to give each of the diastereomers, 3SR, 4aRS,6SR,8aRS (second fraction) and 3SR,4aRS,6RS,8aRS first fraction). The total yield of the title compound was 2.85 g, C. Preparation of (3SR,4aRS,6SR,8aRS)-6-[(1(2)H-Tetrazole-5-yl)methoxymethyl]decahydroisoquinoline-3-carboxylic Acid A mixture of the (3SR,4aRS,6SR,8aRS) isomer from Example 11B (1.99 g) and tributyltin azide (3.83 g) was heated to 80° C. After three days, the reaction mixture was treated with 6N hydrochloric acid (20 ml) and heated to 90° C. After about 18 hours, the reaction mixture was allowed to cool to room temperature. The cooled mixture, containing a white precipitate, was diluted with ether, and filtered. The solids were washed with ether (3 times) and acetone, then dried in vacuo at 60° C., to give 1.16 g of the title compound. Melting point 263° C.

Analysis calculated for $C_{13}H_{21}N_5O_3 \cdot HCl$: C, 47.06; H, 6.68; N, 21.11. Found: C, 46.80; H, 6.85; N, 21.07.

EXAMPLE 12

(3SR,4aRS,6SR,8aRS)-6-[(1(2)H-Tetrazole-5-yl)
but-1-yl]decahydroisoquinoline-3-carboxylic Acid
(10)

A. Preparation of Ethyl 6-(3-Oxoprop-1-yl)-2-methoxycarbonyl-decahydroisoquinoline-3-carboxylate A solution of dimethyl sulfoxide (0.98 g) in methylene chloride (10.2 ml) was cooled to −78° C. and treated with oxalyl chloride (0.53 ml). After two minutes, a solution of the compound from Example 10F (1.65 g) in methylene chloride (6 ml) was to the cold solution. After an additional 15 minutes, the reaction solution was treated with triethylamine (3.5 ml) and the resulting mixture allowed to warm to room temperature over a period of about 45 minutes. The reaction mixture was next treated with 10% sodium bisulfite and ether. The phases were separated and the aqueous phase was extracted with ether (2 times). The organic phases were combined, dried over magnesium sulfate, filtered, and concentrated in vacuo. The residue was used in the next step without further purification.

B. Preparation of Ethyl 6-(4-Cyanoprop-3-en-1-yl)-2-methoxycarbonyldecahydroisoquinoline-3-carboxylate A suspension of sodium hydride (0.28 g, 60%), previously washed with hexane, in THF (7.5 ml) was cooled to 0° C. The cooled mixture was treated with diethyl cyanomethylphosphonate (1.25 g) at 0° C. After 30 minutes, this mixture was treated with a solution of the compound from Example 12A (1.72 g) in anhydrous THF (5 ml), and the resulting mixture allowed to warm co room temperature. After 30 minutes, the reaction mixture was treated with water (30 ml), and extracted with ether (3 times). The organic phases were combined, dried over magnesium sulfate, filtered, and concentrated in vacuo. The residue was used in the next step without further purification.

C. Preparation of (3SR,4aRS,6SR,8aRS) Ethyl 6-(4-Cyanobut-1-yl)-2-methoxycarbonyldecahydroisoquinoline-3-carboxylate A solution of the compound from Example 12B (1.76 g) in methanol (50 ml) was treated with magnesium (2.45 g). After four hours, the reaction mixture was treated with 1N hydrochloric acid (250 ml), and the resulting mixture extracted with ether (3 times). The organic extracts were combined, dried over magnesium sulfate, filtered, and concentrated in vacuo. The residue was purified by silica-gel flash chromatography, eluting with 35% ethyl acetate/hexane, to give two products. The fractions containing the first product, which is the title compound, were concentrated in vacuo to give 0.56 g. The fractions containing the second product, which is the methyl ester of the title compound, were combined to give 0.41 g. These products were combined for use in the next step.

D. Preparation of (3SR,4aRS,6SR,8aRS)-6-[(1(2)H-Tetrazole-5-yl)but-1-yl]decahydroisoquinoline-3-carboxylic Acid A mixture of the compounds from Example 12C (0.97 g) and tributyltin azide (1.78 g) was heated to 60° C. After three days, the mixture was treated with 6N hydrochloric acid (60 ml) and heated to 100° C. After heating for about 18 hours, the mixture was allowed to cool to room temperature. This mixture was extracted with ether (6 times) and the aqueous phase concentrated in vacuo. The residue was purified by ion-exchange chromatography on DOWEX 50X8, eluting with 10% pyridine/water. The fractions containing the title compound were combined and concentrated in vacuo. The residue was diluted with water and concentrated in vacuo. This procedure was repeated. The residue was diluted with a mixture of water and acetone (1:1), and the solid material collected by filtration. This material was dried in vacuo at 60° C., to give 0.70 g of the title compound.

Analysis calculated for $C_{15}H_{25}N_5O_2 \cdot 1.3\ H_2O$: C, 54.46; H, 8.41; N, 21.17. Found: C, 54.48; H, 8.30; N, 20.99.

EXAMPLE 13

(3 SR, 4aRS,6RS,8aRS)-6-(2 -Sulfoethyl) decahydroisoquinoline-3 -carboxylic Acid (12)

A. Preparation of (3SR,4aRS,6RS,8aRS) Ethyl 6-(2-Sulfoethyl)-2-methoxycarbonyldecahydroisoquinoline-3-carboxylate A solution of the 3SR,4aRS,6RS,8aRS isomer from Example 8D (1.8 g) in ethanol (11 ml) and water (18 ml) was treated with sodium sulfite (0.64 g), and the resulting mixture heated to reflux. After heating for about 18 hours, an additional portion of sodium sulfite (0.59 g) was added to the reaction mixture. After an additional 18 hours, the reaction was concentrated in vacuo. The residue was partitioned between ether and water. The phases were separated, and the ether phase extracted with water. The aqueous phases were combined and concentrated in vacuo. This material was used in the next step without further purification.

B. Preparation of (3SR,4aRS,6RS,8aRS)-6-(2-Sulfoethyl) decahydroisoquinoline-3-carboxylic Acid A solution of the compound from Example 13A in 6N hydrochloric acid (80 ml) was heated to reflux. After about 18 hours, the solution was allowed to cool to room temperature and concentrated in vacuo. The residue was purified by ion-exchange chromatography on BIO RAD AG 1X8 (hydroxide form), eluting with 6N acetic acid, to give 0.88 g of the title compound. Melting point 265° C.

Analysis calculated for $C_{12}H_{21}NO_5S \cdot 0.25H_2O$: C, 48.71; H, 7.32; N, 4.73. Found: C, 48.53; H, 7.39; N 4.50.

EXAMPLE 14

(3SR,4aRS,6RS,8aRS)-6-[2-(3-Hydroxyisoxazole-5-yl)ethyl]decahydroisoquinoline-3-carboxylic Acid (13)

A. Preparation of 3-Bromo-5-hydroxymethylisoxazole

To a mixture of potassium bicarbonate (32.5 g), water (4.4 ml), and ethyl acetate (395 ml) was added propargyl alcohol (12.1 g). The resulting mixture was treated with a solution of dibromoformaldoxime (21.97 g) in ethyl acetate (44 ml) over a period of seven hours. After about 18 hours, the reaction mixture was treated with water (150 ml). The phases were separated, and the organic phase extracted with water and brine, dried over magnesium sulfate, filtered, and concentrated in vacuo. This material was used in the next step without further purification.

B. Preparation of 3-Bromo-5-carboxyisoxazole

A solution of the compound from Example 14A (35.2 g) in acetone was treated with Jones Reagent (950 ml). After six hours, the reaction mixture was treated with isopropanol (1 L). The resulting mixture was filtered through CELITE, and the filtrate concentrated in vacuo. The residue was dissolved in ether and extracted with water. The combined aqueous extracts were extracted with ether. The combined organic phases were dried over magnesium sulfate, filtered, and concentrated in vacuo, to give 34.1 g of the title compound.

C. Preparation of 5-Carboxy-3-methoxyisoxazole

A solution of the compound from Example 14B (34.1 g), potassium hydroxide (169 g), methanol (580 ml), and water (103 ml) was heated to reflux. After four hours, the reaction mixture was allowed to cool to room temperature. This mixture was treated with concentrated hydrochloric acid (450 ml), and diluted with water (350 ml). The resulting solution was extracted with ether (6 times). The organic extracts were combined, dried over magnesium sulfate, filtered, and concentrated in vacuo. This residue was diluted with toluene and methanol, and concentrated in vacuo, to give 20.2 g of title compound.

D. Preparation of 5-Hydroxymethyl-3-methoxyisoxazole

A solution of the compound from Example 14C (20.2 g) in THF was treated with triethylamine (14.3 g), and cooled to 0° C. A solution of isobutyl chloroformate (19.3 g) in THF (35 ml) was added to the cooled solution. After 1¼ hours, the precipitate was removed by filtration (210 ml), and washed with THF. The filtrate was carefully added to a solution of sodium borohydride (13.4 g) in water (140 ml). After 4½ hours, the reaction mixture was treated with 1N hydrochloric acid, and the resulting mixture extracted with ether. The combined organic extracts were dried over magnesium sulfate, filtered, and concentrated in vacuo. The residue was purified by silica-gel chromatography on a WATERS PREP 500LC, eluting with 35% ethyl acetate/hexane, to give 9.10 g of the title compound and 1.38 g of 4-hydroxymethyl-3-methoxyisoxazole.

E. Preparation of 5-Bromomethyl-3-methoxyisoxazole

A solution of triphenylphosphine (27.7 g) in methylene chloride (425 ml) was cooled to 0° C., and treated with bromine (16.9 g) until the yellow color persisted. Additional triphenylphosphine was added until the yellow color disappeared. The colorless solution was treated with a solution of the compound from Example 14D (9.10 g) and pyridine (11.2 g) in methylene chloride (11.4 ml). After ten minutes, the reaction solution was extracted with 10% sodium bisulfate (2 times). The organic phases were combined and extracted with methylene chloride (2 times). The organic phases were combined, dried over sodium sulfate, filtered, and concentrated in vacuo. The residue was purified by silica-gel flash chromatography, eluting with a step-gradient of 10% ethyl acetate/hexane followed by 20% ethyl acetate/hexane. The fractions containing the title compound were combined and concentrated in vacuo to give 10.8 g.

F. Preparation of Diethyl[(3-Methoxyisoxazole-5-yl)methyl]phosphonate

A solution of the compound from Example 14E (10.8 g) in toluene (150 ml) was treated with triethylphosphite (18.7 g). This solution was heated to a temperature of about 120° C. After about 18 hours, the reaction solution was concentrated in vacuo. The residue was purified by silica-gel chromatography on a WATERS PREP 500LC, eluting with a linear gradient of ethyl acetate to 5% ethanol/ethyl acetate, to give 11.77 g of the title compound.

G. Preparation of Ethyl 6-[2-(3-Methoxyisoxazole-5-yl)ethenyl]-2-methoxycarbonyldecahydroisoquinoline-3-carboxylate A solution of the compound from Example 14F (3.71 g) in THF (10 ml) was cooled to −17° C. and treated with a 1M solution of sodium bis(trimethylsilyl)amide in THF (14.9 ml). After 30 minutes, this solution was treated with a solution of the compound from 7A (3.15 g) in THF (10 ml). The resulting solution was allowed to warm to room temperature. After 1½ hours, the reaction solution was treated with water and extracted with ether. The combined organic extracts were dried over magnesium sulfate, filtered, and concentrated in vacuo. The residue was purified by silica-gel flash chromatography, eluting with 15% ethylene acetate/toluene, to give 2.95 g of the title compound.

H. Preparation of (3SR,4aRS,6RS,8aRS) Ethyl 6-[2-(3-Methoxyisoxazole-5-yl)ethyl]-2-methoxycarbonyldecahydroisoquinoline-3-carboxylate A mixture of the compound from Example 14G (2.33 g) and 5% palladium on carbon (2.33 g) in ethyl acetate (50 ml) was hydrogenated at a hydrogen pressure of 60 psi. After six hours at room temperature, the reaction mixture was filtered through CELITE, and the filtrate concentrated in vacuo. The residue was diluted with chloroform and concentrated in vacuo. This residue was purified by silica-gel flash chromatography, eluting with a linear gradient of 5% ethyl acetate/toluene to 15% ethyl acetate/toluene, to give 1.0 g of the title compound.

I. Preparation of (3SR,4aRS,6RS,8aRS)-6-[2-(3-Hydroxyisoxazole-5-yl)ethyl]decahydroisoquinoline-3-carboxylic Acid A mixture of the compound from Example 14H (0.92 g) and 48% hydrobromic acid was heated to reflux. After three hours, the reaction mixture was allowed to cool to room temperature and concentrated in vacuo. The residue was diluted with water and concentrated in vacuo. This residue was diluted with water and filtered to remove the solids. The solid material was washed with acetone and dried in vacuo at room temperature, to give 0.26 g. This material was further purified by ion-exchange chromatography on DOWEX 50X8, eluting with 10% pyridine/water, to give 0.115 g of the title compound. Melting point 256° C.

Analysis calculated for $C_{15}H_{22}N_2O_4 \cdot 1.0H_2O$: C, 57.67; H, 7.74; N, 8.96. Found: C, 57.78; H, 7.75; N, 9.07.

EXAMPLE 15

(3SR,4aRS,6SR,8aRS)-6-[2-(1(2-4)H-1,2,4-Triazol-5-yl)-2-thiaethyl]decahydroisoquinoline-3-carboxylic Acid (14)

A. Preparation of (3SR,4aRS,6SR,8aRS) Ethyl 6-[2-(1(2-4)H-1,2,4-Triazol-5-yl)-2-thiaethyl]-2-methoxycarbonyl decahydroisoquinoline-3-carboxylate A solution of the compound from Example 7C (9.22 g) in anhydrous dimethylformamide (92 ml) was treated with 1H-1,2,4-triazole-3-thiol (3.09 g) and triethylamine (6.19 g). The resulting solution was heated to 100° C. for about 18 hours. The cooled reaction solution was treated with 10% sodium bisulfate (200 ml), and extracted with chloroform/ethyl acetate (1:1)and ether. The organic phases were combined, dried over magnesium sulfate, filtered, and concentrated in vacuo. The residue was heated to about 50° C. in vacuo to remove the residual dimethylformamide. This residue was purified by silica-gel chromatography on a WATERS PREP LC 2000, eluting with a linear gradient of 35% ethyl acetate/hexane to ethyl acetate. The fractions containing the title compound were combined and concentrated in vacuo. The residue was diluted with ethyl acetate and extracted with 1N hydrochloric acid and brine. The organic layer was dried over magnesium sulfate, filtered, and concentrated in vacuo, to give 9.37 g of the title compound.

B. Preparation of (3SR,4aRS,6SR,8aRS)-6-[2-(1(2-4)H-1,2,4-Triazol-5-yl)-2-thiaethyl]decahydroisoquinoline-3-carboxylic Acid A mixture of the compound from Example 15A (1.77 g) in 6N hydrochloric acid (10 ml) was heated to 100° C. After about 18 hours, the reaction mixture was concentrated in vacuo. The residue is purified by ion-exchange chromatography, eluting with 10% pyridine/water. The fractions containing the title compound were combined and concentrated in vacuo. The residue was diluted with water and concentrated in vacuo. This procedure was repeated four times, then the residue was dried in vacuo overnight. This material was dissolved in acetone and heated to reflux for one hour. This mixture was allowed to cool to room temperature, then the title compound removed by filtration. The solids were washed with acetone and ether, then dried in vacuo at 40° C., to give 0.37 g of the title compound.

Analysis calculated for $C_{13}H_{20}N_4O_2S \cdot 2.0H_2O$: C, 46.97; H, 7.27; N, 16.85. Found: C, 46.88; H, 7.33; N, 16.74.

EXAMPLE 16

(3SR,4aRS,6SR,8aRS)-6-[(1(2-4)H-1,2,4-Triazole-5-yl)sulfonylmethyl]decahydroisoquinoline-3-carboxylic Acid (15)

A solution of the compound from Example 15A (9.37 g) in methylene chloride (105 ml) was treated with 3-chloroperoxybenzoic acid (13.25 g) in three portions over a period of 30 minutes. After about 18 hours at room temperature, the reaction mixture was concentrated in vacuo. The residue was purified by silica-gel flash chromatography, eluting with a step gradient of 50% ethyl acetate/hexane (500 ml) followed by ethyl acetate (2 L), to give 8.98 g of a clear oil.

The clear oil was treated with 6N hydrochloric acid (250 ml) and heated to 110° C. After about 18 hours, the reaction mixture was allowed to cool to room temperature and concentrated in vacuo. The residue was dissolved in water (100 ml), and resulting solution extracted with ether. The phases were separated and the aqueous phase concentrated in vacuo. The residue was purified by ion-exchange chromatography on DOWEX 50X8, eluting with 10% pyridine/water. The fractions containing the title compound were combined and concentrated in vacuo. The residue was diluted with water and concentrated in vacuo. This process was repeated two times, and the residue was concentrated in vacuo for about 18 hours. This residue was diluted with acetone (250 ml) and refluxed for one hour. The title compound was removed by filtration, then washed with acetone and ether. The solids were dried in vacuo at 60° C. for about 18 hours to give 3.56 g of the title compound.

Analysis calculated for $C_{13}H_{20}N_4O_4S \cdot H_2O$: C, 45.08; H, 6.40; N, 16.17. Found: C, 45.40; H, 6.31; N, 16.39.

EXAMPLE 17

(3SR,4aRS,6RS,8aRS)-6-[2-((N-Methanesulfonyl)carboxamido)ethyl]decahydroisoquinoline-3-carboxylic Acid (16)

A. Preparation of (3SR,4aRS,6RS,8aRS) Ethyl 6-[2-((N-Methanesulfonyl)carboxamido)ethyl]-2-methoxycarbonyldecahydroisoquinoline-3-carboxylate A solution of 1,1'-carbonyldiimidazole (1.9 g) in anhydrous THF (25 ml) was treated with a solution of the compound from Example 10E (4 g) in THF (25 ml). The resulting solution was heated to reflux for one hour, then allowed to cool to room temperature. The cooled solution was treated with methanesulfonamide (1.11 g). After ten minutes, this solution was treated with a solution of 1,8-diazabicyclo[5.4.0]undec-7-ene (1.8 g) in THF (10 ml). After about 18 hours, this solution was treated with 1N hydrochloric acid (150 ml). The resulting mixture was extracted with ether. The ether extracts were combined and extracted with saturated sodium bicarbonate. The phases were separated, and the aqueous phase acidified with 5N hydrochloric acid. The acidic aqueous layer was extracted with ether. The ether extracts were combined, dried over sodium sulfate, filtered, and concentrated in vacuo, to give 4.35 g of the title compound.

B. Preparation of (3SR,4aRS,6RS,8aRS)-6-[2-((N-Methanesulfonyl)carboxamido)ethyl]-2-methoxycarbonyldecahydroisoquinoline-3-carboxylic Acid A solution of the compound from Example 17A in ethanol (45 ml) was treated with 1N sodium hydroxide (22.6 ml). After about 18 hours at room temperature, the reaction solution was partially concentrated in vacuo to remove the ethanol. The residue was extracted with ethyl acetate. The aqueous layer was acidified with 5N HCl, then extracted with ethyl acetate. The ethyl acetate extracts were combined, dried over sodium sulfate, filtered, and concentrated in vacuo to give 3.7 g of the title compound. This material was used in the next step without purification.

C. Preparation of (3SR,4aRS,6RS,8aRS)-6-[2-((N-Methanesulfonyl)carboxamido)ethyl]decahydroisoquinoline-3-carboxylic Acid A solution of the compound from Example 17B (3.7 g) in chloroform (40 ml) was treated with iodotrimethylsilane (11.4 g). This solution was heated at reflux for two hours, then concentrated in vacuo. The residue was treated with water (25 ml), extracted with ether, and concentrated in vacuo. The residue was purified by ion-exchange on DOWEX 50X8-100, eluting with 10% pyridine/water, to give 2.75 g of the title compound. Melting point 208°–215° C.

Analysis calculated for: $C_{14}H_{24}N_2O_5S$: C, 50.59; H, 7.28; N, 8.43. Found: C, 50.36; H, 7.47; N, 8.55.

EXAMPLE 18

(3SR,4aRS,6RS,8aRS)-6-[2-(N-(1(2)H-Tetrazole-5-yl)carboxamido)ethyl]decahydroisoquinoline-3-carboxylic Acid (17)

A. Preparation of (3SR,4aRS,6RS,8aRS) Ethyl 6-[2-(N-(1(2)H-Tetrazole-5-yl)carboxamido)ethyl]decahydroisoquinoline-3-carboxylate A solution of the compound from Example 10E (4 g) in dry THF (25 ml) was treated with a solution of 1,1'-carbonyldiimidazole (1.9 g) in dry THF (25 ml). The resulting solution was heated at reflux for one hour, and treated with 5-aminotetrazole (1 g). After heating at reflux for about 18 hours, the reaction solution was allowed to cool to room temperature. The cooled solution was treated with 1N hydrochloric acid (150 ml), and extracted with ether. The organic extracts were combined and extracted with saturated sodium bicarbonate solution. The aqueous bicarbonate extracts were combined, acidified with 5N hydrochloric acid and extracted with ether. The ether extracts were combined, dried over sodium sulfate, filtered, and concentrated in vacuo, to give 4.6 g of the title compound.

B. Preparation of (3SR,4aRS,6RS,8aRS)-6-[2-(N-(1(2)H-Tetrazole-5-yl)carboxamido)ethyl]-2-methoxycarbonyldecahydroisoquinoline-3-carboxylic Acid A solution of the compound from Example 18A (4.4 g) in ethanol (45 ml) was treated with 1N sodium hydroxide (23.7 ml). After about 18 hours at room temperature, the solution was partially concentrated in vacuo to remove the ethanol. The residue was acidified with 5N hydrochloric acid and extracted with ethyl acetate. The organic phases were combined, extracted with saturated sodium chloride, dried over sodium sulfate, filtered, and concentrated in vacuo to give 3.9 g of the title compounds.

C. Preparation of (3SR,4aRS,6RS,8aRS)-6-[2-(N-(1(2)H-Tetrazole-5-yl)carboxamido)ethyl]decahydroisoquinoline-3-carboxylic Acid A solution of the compound from Example 18B (3.9 g) in chloroform (45 ml) was treated iodotrimethylsilane (12.3 g). The resulting solution was heated to reflux for two hours. The solution was then concentrated in vacuo, and the residue treated with water (30 ml). This mixture was extracted with ether, then the aqueous layer concentrated in vacuo. The residue was purified by ion-exchange chromatography on DOWEX 50X8-100, eluting with 10% pyridine/water, to give 3.1 g of the title compound. Melting point>220° C.

Analysis calculated for: $C_{14}H_{22}N_6O_3.2.3H_2O$: C, 46.22; H, 7.37; N, 23.10. Found: C, 46.13; H, 7.65; N, 23.14.

EXAMPLE 19

(3SR,4aRS,6RS,8aRS)-6-[2-(1(2)H-Tetrazole-5-yl)-1-methylethyl]decahydroisoquinoline-3-carboxylic Acid (18)

A. Preparation of Ethyl 2-Methoxycarbonyl-6-trifluoromethanesulfonyloctahydroisoquinoline-3-carboxylate A solution of lithium bis(trimethylsilyl)amide (100 ml of a 1M solution in THF) in anhydrous THF (180 ml) was cooled to −78° C. and treated with a solution of the racemic compound from Example 5C (25.8 g) in anhydrous THF (60 ml). After one hour at −78° C., the cold solution was treated with a solution of N-phenyltrifluoromethanesulfonimide (32.5 g) in THF (100 ml). This solution was allowed to warm to room temperature. After about three hours, the reaction solution was diluted with ether (100 ml) and extracted with 10% sodium bisulfate. The aqueous extracts were combined and extracted with ether (3 times). The organic phases were combined, dried over sodium sulfate, filtered, and concentrated in vacuo. The residue was purified by silica-gel chromatography on a WATERS PREP 500 LC, eluting with an 8-L gradient of hexane to 25% ethyl acetate/hexane, to give 24.4 g of the title compound.

B. Preparation of Ethyl 6-(2-Cyano-1-methylethenyl)-2-methoxycarbonyloctahydroisoquinoline-3-carboxylate A solution of the compound from Example 19A (2.5 g) in dimethylformamide (21 ml), that was degassed with nitrogen prior to use, was treated with crotononitrile (1 g), triethylamine (2.1 g), and bis(triphenylphosphine)palladium (II) chloride (97 mg). This mixture was heated to a temperature of about 70° C. to about 80° C. under nitrogen. After about 18 hours at about 75° C., the reaction mixture was treated with water (100 ml). This mixture was extracted with ether/hexane (1:1). The organic extracts were combined, washed with saturated sodium chloride solution, dried over sodium sulfate, filtered, and concentrated in vacuo. The residue was purified by silica-gel flash chromatography, eluting with 25% ethyl acetate/hexane, to give 1.17 g of the title compound.

C. Preparation of Ethyl 6-(2-Cyano-1-methylethyl)-2-methoxycarbonyldecahydroisoquinoline-3-carboxylate A mixture of the compound from Example 19B (1.1 g) and 5% palladium on carbon in ethanol (80 ml) was hydrogenated at a hydrogen pressure of 60 psi at room temperature. After six hours, the catalyst was removed by filtration and the filtrate concentrated in vacuo. The residue was dissolved in ethyl acetate, and the resulting solution filtered through a 0.2μ ACCCODISC. The residue was purified by silica-gel flash chromatography, eluting with the linear gradient of ethyl acetate/hexane (1:4) to ethyl acetate/hexane (3:7), to give 0.66 g of the title compound.

D. Preparation of (3SR,4aRS,6RS,8aRS)-6-[2-(1(2)H-Tetrazole-5-yl)-1-methylethyl]decahydroisocfuinoline-3-carboxylic Acid The compound from Example 19C (600 mg) was added to tributyltin azide (1.18 g), and the mixture heated to about 80° C. After four days, the mixture was treated with 6N hydrochloric acid (5 ml) and heated at reflux. After heating for about 18 hours, the mixture was allowed to cool to room temperature. The mixture was extracted with ether, and the aqueous phase concentrated in vacuo. The residue was purified by ion-exchange chromatography on DOWEX 50X8-100, eluting with 10% pyridine/water, to give 0.37 g of the title compound.

Analysis calculated for: $C_{14}H_{23}N_5O_2 \cdot 1.1H_2O$: C, 53.69; H, 8.11; N, 22.36. Found: C, 53.63; H, 8.01; N, 22.16.

EXAMPLE 20

(3SR, 4aRS,6RS,8aRS)-6-[2-(1(2)H-Tetrazole-5-yl)-1-phenylethyl]decahydroisoquinoline-3 -carboxylic Acid (19)

A. Preparation of Ethyl 6-(2-Cyano-1-phenylethenyl)-2-methoxycarbonyldecahydroisoquinoline-3-carboxylate A solution of the compound from Example 19A (2.5 g) in dimethylformamide (21 ml), that was degassed with nitrogen before use, was treated with cinnamonitrile (1.94 g), triethylamine (2.1 g), and bis(triphenylphosphine)palladium (II) chloride (97 mg). This mixture was heated to a temperature of about 70° C. to about 80° C. under a nitrogen atmosphere. After heating for about 18 hours am about 75° C., the reaction mixture was treated with water (100 ml). This mixture was extracted with ether/hexane (1:1). The organic extracts were combined, washed with saturated sodium chloride solution, dried over sodium sulfate, filtered, and concentrated in vacuo. The residue was purified by silica-gel flash chromatography, eluting with a linear gradient of ethyl acetate/hexane (1:4) to ethyl acetate/hexane 3:7), to give 1.45 g of the title compound.

B. Preparation of Ethyl 6-(2-Cyano-1-phenylethyl)-2-methoxycarbonyldecahydroisoquinoline-3-carboxylate A mixture of the compound from Example 20A (1.35 g) and 5% palladium on carbon in ethanol (85 ml) was hydrogenated at a hydrogen pressure of 60 psi at room temperature. After six hours, the catalyst was removed by filtration. The filtrate was concentrated in vacuo, dissolved in ethyl acetate, filtered through a 0.2µ ACCODISC, and concentrated in vacuo. The residue was purified by silica-gel flash chromatography, eluting with a linear gradient of ethyl acetate/hexane (1:3) to ethyl acetate/hexane 2:3), to give 0.61 g of the title compound.

C. Preparation of (3SR,4aRS,6RS,8aRS)-6-[2-(1(2)H-Tetrazole-5-yl)-1-phenylethyl]decahydroisoquinoline-3-carboxylic Acid The compound from Example 20B (0.59 g) was added to tributyltin azide (6 g), and the mixture heated to about 80° C. After four days, the mixture was treated with 6N hydrochloric acid (5 ml) and heated at reflux. This mixture was extracted with ether and the aqueous phase concentrated in vacuo. The residue was purified by ion-exchange chromatography on DOWEX 50X8-100, eluting with 10% pyridine, to give 0.38 g of the title compound.

Analysis calculated for: $C_{19}H_{25}N_5O_2 \cdot 1.8H_2O \cdot 0.25C_3H_6O$: C, 58.95; H, 7.54; N, 17.40. Found: C, 59.29; H, 6.71; N, 17.01.

EXAMPLE 21

(3SR,4aRS,6SR,8aRS)-6-[2-(3-Hydroxy-1,2,5-thiadiazole-4-yl)ethenyl]decahydroisoquinoline-3-carboxylic Acid (20)

A. Preparation of 3-Hydroxymethyl-4-hydroxy-1,2,5-thiadiazole

A solution of 2-amino-3-hydroxypropanamide hydrochloride (20.25 g) in acetonitrile (270 ml) was treated with N-methyl-N-(trimethylsilyl)trifluoroacetamide (172 g). After one hour, this solution was cooled to 0° C. and treated with triethylamine (20 ml). After about five minutes, the resulting solution was treated with a solution of condensed sulfur dioxide (30.75 ml) in acetonitrile (113.25 ml). After addition of the sulfur dioxide solution was complete, the ice-bath was removed and the reaction mixture allowed to warm to room temperature. After three hours, the reaction mixture was placed in a refrigerator overnight. After an additional two hours at room temperature, the reaction mixture was treated with water (8.55 ml). After fifteen minutes, the resulting mixture was concentrated in vacuo. The residue was treated with water (400 ml) and extracted with methylene chloride. The organic extracts were discarded and the aqueous phase concentrated in vacuo. The residue was treated with THF (250 mi), sonicated in an ultrasonic bath, and filtered. The THF filtrate was concentrated in vacuo. This residue was dissolved in hot acetone (36 ml), and the resulting solution treated with chloroform (165 ml). This mixture was concentrated on a steam bath to a volume of about 165 ml, then filtered. The filtrate was concentrated to about 150 ml, cooled, sonicated in an ultrasonic bath, and refrigerated, to give 5.9 g of the title compound.

B. Preparation of 3-Hydroxy-4-iodomethyl-1,2,5-thiadiazole

A solution of the compound from Example 21A (5.90 g) in anhydrous acetonitrile (90 ml) was treated with N-methyl-N-(trimethylsilyl)trifluoroacetamide (18.59 g) and iodotrimethylsilane (26.80 g). The resulting solution was heated to 55° C. for 15 hours, then allowed to stand at room temperature for 3½ hours. The reaction mixture was concentrated in vacuo, and dissolved in chloroform (300 ml). The organic solution was washed with water, 1N sodium bisulfite, and additional water. The organic layer was concentrated in vacuo, and the residue treated with acetonitrile (62 ml) and water (6.4 ml). After 40 minutes at room temperature, this mixture was concentrated in vacuo. The residue was treated with acetonitrile (8.3 ml), filtered, and the solid material washed with acetonitrile. The filtrate was concentrated in vacuo, then treated with water (20.8 ml). After 15 minutes at room temperature, this mixture was filtered and the solid material washed with water. This material was dried in vacuo at 60° C., to give 5.99 g of the title compound.

C. Preparation of 3-Diphenylmethoxy-4-iodomethyl-1,2,5-thiadiazole

A solution of the compound from Example 21B (5.99 g) in methylene chloride (100 ml) was treated with diphenyldiazomethane (4.80 g). After a period of about ten minutes, additional diphenyldiazomethane was added. After an additional ten minutes, the reaction solution was treated with acetic acid, then concentrated in vacuo. The residue was purified by silica-gel chromatography on a WATERS PREP 500LC, eluting with an 8-L gradient of hexane to 50% ethyl acetate/hexane, to give 6.35 g of the title compound.

D. Preparation of 3-(Diethyl phosphonomethyl)-4-diphenylmethoxy-1,2,5-thiadiazole A solution of the compound from Example 21C (6.05 g) and triethylphosphite (4.92 g) in toluene (120 ml) was heated to reflux. After about 18 hours, additional triethylphosphite (0.25 equivalents) was added. After about three hours, the reaction mixture was allowed to cool to room temperature and concentrated in vacuo. The residue was purified by silica-gel chromatography, eluting with ethyl acetate/hexane (1:1), to give 5.71 g of the title compound.

E. Preparation of (3SR,4aRS,6SR,8aRS) Ethyl 6-[2-(3-Diphenylmethoxy-1,2,5-thiadiazole-4-yl)ethenyl]-2-methoxycarbonyldecahydroisoquinoline-3-carboxylate.

A suspension of sodium hydride (0.49 g), previously washed with hexane, in freshly distilled tetrahydrofuran (25 ml) was cooled to 0° C. and treated with a solution of the compound from Example 21D (5.10 g) in tetrahydrofuran (5 ml). After about thirty minutes, this solution was treated with a solution of the compound from Example 7A (3.45 g) in tetrahydrofuran (15 ml). This mixture was allowed to warm to room temperature. After 30 minutes, the reaction was worked up as described in Example 14G, to give 5.43 g of the title compound.

F. Preparation of (3SR,4aRS,6SR,8aRS) Ethyl 6-[2-(3-Hydroxy-1,2,5-thiadiazole-4-yl)ethenyl]decahydroisoquinoline-3-carboxylate A solution of the compound from Example 21E (5.43 g) in methylene chloride (119 ml) was cooled to 0° C. and treated with triethylsilane (11.22 g) and trifluoroacetic acid (22.0 g). After one hour at 0° C., the reaction mixture was concentrated in vacuo. The residue was purified by silica-gel chromatography, eluting with ethyl acetate/hexane (1:1). The fractions containing the title compound were concentrated in vacuo. The residue was dissolved in chloroform and concentrated in vacuo to give 3.55 g of the title compound.

G. Preparation of (3SR,4aRS,6SR,8aRS)-6-[2-(3-Hydroxy-1,2,5-thiadiazole-4-yl)ethenyl]decahydroisoquinoline-3-carboxylic Acid A solution of the compound from Example 21F (1.10 g) in 6N hydrochloric acid (about 25 ml) was heated to about 90° C. After about 18 hours, the reaction solution was allowed to cool to room temperature. This mixture was treated with water (15 ml). The pH of this solution was adjusted to pH 10 with the addition of 5N sodium hydroxide. The solution was then made acidic (pH=5) with the addition of 5N hydrochloric acid. The precipitate was removed by filtration, then washed with water, acetone, and ether. This material was dried in vacuo at room temperature, to give 0.33 g of the title compound. Melting point 239°–242° C.

Analysis calculated for $C_{17}H_{24}N_2O_4$: C, 63.73; H, 7.55; N, 8.74. Found: C, 63.68; H, 7.65; N, 8.85.

EXAMPLE 22

(3SR,4aRS,6RS,8aRS)-6-[2-(1(2)H-Tetrazole-5-yl) ethyl]decahydroisoquinoline-3-carboxylic Acid (1)

A. Preparation of (3SR,4aRS,6SR,8aRS) Ethyl 6-(2-Cyano-1-ethenyl)-2-methoxycarbonyldecahydroisoquinoline-3-carboxylate A suspension of sodium hydride (6.98 g, 60%), previously washed with hexane, in THF (185 ml), was treated with diethyl cyanomethylphosphonate (30.93 g). The resulting mixture was cooled to 0° C. and treated with a solution of the compound from Example 10C (37.1 g) in THF (185 ml). After 45 minutes, the reaction mixture was treated with 10% sodium bisulfate (200 ml) and ether (400 ml). The phases were separated and the aqueous phase extracted with ether (2 times). The organic phases were combined, dried over magnesium sulfate, filtered, and concentrated in vacuo. The residue was purified by silica-gel flash chromatography, eluting with 35% ethyl acetate/hexane, to give 37.84 g of the title compound.

B. Preparation of (3SR,4aRS,6RS,8aRS) Ethyl 6-(2-Cyanoethyl)-2-methoxycarbonyldecahydroisoquinoline-3-carboxylate A solution of the compound from Example 22A (37.8 g) in methanol (1150 ml) was treated with magnesium (57.4 g). After 15 minutes at room temperature, the reaction mixture was cooled in an ice-water bath. After 1½ hours the reaction mixture was treated with methylene chloride (1.5 L) and filtered through CELITE. The filtrate was separated into two portions, and each portion was extracted with 10% sodium sulfate (2 L). The phases were separated and the aqueous phase extracted with methylene chloride (3 times) and ether (1 time). The organic phases were combined, dried over magnesium sulfate, filtered, and concentrated in vacuo. The residue was purified by silica-gel chromatography on a WATERS PREP 500LC, eluting with a linear gradient of hexane to 35% ethyl acetate/hexane, to give fractions containing the title compound and the corresponding methyl ester, and a mixture thereof. These fractions were combined and concentrated in vacuo, to give 28 g of a mixture of the title compound and the corresponding methyl ester.

C. Preparation of (3SR,4aRS,6RS,8aRS)-6-[2-(1(2)H-Tetrazole-5-yl)ethyl]decahydroisoquinoline-3-carboxylic Acid A mixture of the compounds from Example 22B (27.96 g) and tributyltin azide (57.96 g) was heated to 80° C. After 48 hours, the mixture was treated with 6N hydrochloric acid (200 ml) and heated to 90° C. After heating about 18 hours, the mixture was allowed to cool to room temperature. This mixture was treated with water and the pH adjusted to about pH 5. This mixture was concentrated in vacuo to give a solution containing a white precipitate. This solid material was removed by filtration, and washed with water and acetone, to give 13.42 g of the title compound. Melting point 220° C.

Analysis calculated for $C_{13}H_{21}N_5O_2 \cdot 0.5H_2O$: C, 54.15; H, 7.69; N, 24.29. Found: C, 53.81; H, 7.25; N, 24.26.

EXAMPLE 23

(3SR,4aRS,6SR,8aRS)-6-[2-(1(2)H-Tetrazole-5-yl) ethyl]decahydroisoquinoline-3-carboxylic Acid (2)

A. Preparation of Ethyl 6-Formyl-2-methoxycarbonyldecahydroisoquinoline-3-carboxylate A solution of the compound from Example 6A (28.85 g) and 1N hydrochloric acid (52 ml) in acetonitrile (155 ml) was allowed to stand at room temperature. After 4½ hours, the reaction mixture was diluted with ether (1.5 liters) and saturated sodium bicarbonate (500 ml). The phases were separated and the aqueous phase extracted with ether (2 times). The organic phases were combined, dried over magnesium sulfate, filtered, and concentrated in vacuo. This material was used in the next step without further purification.

B. Preparation of Ethyl 6-(2-Cyanoethenyl)-2-Methoxycarbonyldecahydroisoquinoline-3-carboxylate A suspension of sodium hydride (5.91 g, 60%), previously washed with hexane, in THF (114 ml) was treated with diethyl cyanomethylphosphonate (22.98 g). After 20 minutes, this mixture was cooled to 0° C. The cold reaction solution was treated with a solution of the compound from Example 23A (27.56 g) in THF (143 ml), and the resulting mixture allowed to warm to room temperature. After one hour, the reaction mixture was treated with water (200 ml) and extracted with ether. The ether extracts were combined, washed with saturated sodium chloride solution, dried over magnesium sulfate, filtered, and concentrated in vacuo to give 33.7 g of the title compound. This material was used in the next step without further purification.

C. Preparation of (3SR,4aRS,6SR,8aRS) Ethyl 6-[2-(1(2)H-Tetrazole-5-yl)ethyl]2-methoxycarbonyldecahydroisoquinoline-3-carboxylate A mixture of the compound from Example 22B (9.17 g) and 5% palladium on carbon (3.0 g) in ethanol (285 ml) was hydrogenated at a hydrogen pressure of 60 psi at room temperature. After six hours, the mixture was concentrated in vacuo. The residue was dissolved in ethyl acetate, filtered through CELITE, and the filtrate concentrated in vacuo. This material was diluted with chloroform, the resulting mixture filtered, and the filtrate concentrated in vacuo. The residue was purified by silica-gel chromatography on a WATERS PREP 500 LC, eluting with a linear gradient of hexane to 50% ethyl acetate/hexane, to give fractions containing the diastereomers, 3SR,4aRS,6SR,8aRS, and 3SR,4aRS,6RS,8aRS, and a mixture thereof. The yield of the title compound was 0.74 g.

D. Preparation of (3SR,4aRS,6SR,8aRS)-6-[2-(1(2)H-Tetrazole-5-yl)ethyl]decahydroisoquinoline-3-carboxylic Acid A mixture of the 3SR,4aRS,6SR,8aRS racemic mixture from Example 23C (0.74 g) and tributyltin azide (1.52 g) was heated to 80° C. After 66 hours, the mixture was treated with 6N hydrochloric acid (11 ml) and heated to 100° C. After heating for about 18 hours, the mixture was allowed to cool to room temperature and concentrated in vacuo. The residue was treated with water (20 ml) and heated to about 80° C. to affect dissolution. The resulting mixture was allowed to cool to room temperature, filtered through CELITE, and the solids washed with water. The filtrate and wash were combined and concentrated in vacuo. The residue was purified by ion-exchange chromatography on DOWEX 50X8, eluting with 10% pyridine/water. The fractions containing the title compound were combined and concentrated in vacuo. The residue was suspended in acetone, heated to reflux for one hour, and allowed to cool to room temperature. The resulting mixture was filtered, and the precipitate washed with acetone and ether. This material was dried in vacuo at 80° C., to give 0.36 g of the title compound. Melting point 254°–255° C.

Analysis calculated for $C_{13}H_{21}N_5O_2 \cdot 0.5H_2O \cdot 0.2C_3H_6O$: C, 54.45; H, 7.79; N, 23.34. Found: C, 54.36; H, 7.41; N, 23.33.

EXAMPLE 24

(3S,4aR,6R,8aR)-(−)-6-[2-(1(2)H-Tetrazole-5-yl)ethyl]decahydroisoquinoline-3-carboxylic Acid (21)

A. Preparation of 5-(2-Hydroxyethyl)-(1(2)H-Tetrazole

A mixture of sodium azide (34.4 g) and toluene (150 ml) was treated with tributyltin chloride (153 ml). After fifteen minutes at room temperature, this mixture was treated with 3-hydroxypropionitrile (48 ml). The resulting mixture was heated to about 90° C. After 20 hours, 2 molar equivalents of 6M HCl were added and the resulting mixture heated to reflux for 12 hours. The reaction mixture was allowed to cool to room temperature and transferred to a sepratory funnel. The aqueous layer was removed and washed with 1,2-dichloroethane (4×50 ml) and ethyl acetate (100 ml). The aqueous layer was concentrated in vacuo to a thick slurry. This material was treated in ethanol (180 ml) and the solids (NaCl) removed by filtration. The filtrate was concentrated in vacuo to give 29.4 grams of the title compound.

B. Preparation of [2-(1(2)H-Tetrazole-5-yl)ethyl]triphenylphosphonium Bromide

A mixture of the compound from Example 24A (12.80 g) in xylene (76 ml) was treated with triphenylphosphine hydrobromide (38.48 g). The resulting thick slurry was heated to about 150° C. and the water removed by azeotropic distillation. After two hours, the reaction mixture was cooled about 100° C. and treated with 1,2-dichloroethane (100 ml). The resulting mixture was heated at about 100° C. for thirty minutes, and then allowed to cool to room temperature. This mixture was filtered to give 18.1 g of the title compound. The filtrate was concentrated in vacuo to dryness. Additional title compound (22.3 g) was obtained from this residue by recrystallization from ethyl acetate. Melting point 222.2° C.

$^1$H NMR (d$_6$-DMSO): δ7.82 (m, 15H), 4.26 (m, 2H), 3.30 (m, 2H).

$^{13}$C NMR (d$_6$-DMSO): δ135.08, 135.05, 133.73, 133.59, 130.34, 130.17, 118.11, 116.97.

High resolution mass spectrum (FAB): analysis calculated for $C_{21}H_{20}N_4P^+$: 359.14256. Found: 359.14320.

C. Preparation of (3S,4aR,8aR)-6-[2-(1(2)H-Tetrazole-5-yl)ethenyl]-2-methoxycarbonyldecahydroisoquinoline-3-carboxylic Acid A mixture of the compound from Example 4C (0.65 g) and the compound from Example 24B (1.19 g) and dimethylformamide (10 ml) was cooled to 0° C. The cold suspension was treated with a 1M solution of sodium bis(trimethylsilyl)amide in THF (6.0 ml). After two hours at 0° C., the resulting suspension was treated with water (30 ml). The resulting mixture was extracted with ethyl acetate (4×25 ml). The aqueous layer was acidified with 1M HCl to pH 2, then extracted with additional ethyl acetate (4×25 ml). The ethyl acetates were combined, dried over sodium sulfate, filtered, and concentrated in vacuo to give the title compound.

D. Preparation of (3S,4aR,6R,8aR)-(−)-6-[2-(1(2)H-Tetrazole-5-yl)ethyl]decahydroisoquinoline-3-carboxylic Acid A mixture of the compound from Example 24C (0.220 g) and 10% palladium on carbon (0.20 g) and ethanol (5 ml) was hydrogenated at a hydrogen pressure of 50 psi at room temperature. After about three days, the reaction mixture was filtered through CELITE, and the filtrate concentrated in vacuo. The residue was treated with 6M hydrochloric acid (6 ml) and heated to reflux. After about three hours, the reaction mixture was allowed to cool to room temperature. This mixture was extracted with ethyl acetate and the aqueous concentrated in vacuo to give 0.179 g of the title compound. Melting point 250°–257° C.

$[\alpha]_D = -30.0°$ (c=1, 1N HCl)

Analysis calculated for $C_{13}H_{21}N_5O_2 \cdot 0.6H_2O \cdot 0.1C_3H_6O$: C, 53.98; H, 7.77; N, 23.66. Found: C, 53.62; H, 7.38; N, 23.32.

EXAMPLE 25

(3S,4aR,6S,8a,R)-6-[2-(1(2)H-Tetrazole-5-yl)ethyl]decahydroisoquinoline-3-carboxylic Acid (22)

A. Preparation of (3S,4aS,8aR) Ethyl 2-Methoxycarbonyl-6-(methoxymethylene)decahydroisoquinoline-3-carboxylate A suspension of (methoxymethyl)triphenylphosphonium chloride (11.9 g), previously washed with THF in pentane and dried in vacuo at room temperature, in tetrahydrofuran (35 ml) at a temperature of 0° C. was added to a 1M solution of sodium bis(trimethylsilyl)amide in THF (34.6 ml). After 30 minutes, the reaction solution was added to a solution of the compound from Example 4C (7.00 g) in THF (50 ml) at a temperature of about 0° C. The reaction was quenched by the addition of water. The resulting solution was diluted with ether, and the organic phase separated and washed with. water. The combined organic solution was washed with brine, dried over magnesium sulfate, filtered, and concentrated in vacuo. The residue was suspended in ethyl acetate/hexane (1:1) and the resulting suspension stored at room temperature for 10 minutes, filtered, and the filtrate concentrate in vacuo. The solid material was suspended in additional ethyl acetate/hexane (1:1), stirred at room temperature and filtered. The combined ethyl acetate/hexane filtrates were combined and concentrated in vacuo. The product was purified by silica-gel flash chromatography, eluting with 35% ethyl acetate/hexane, to give 6.72 g of the title compound.

B. Preparation of (3S,4aR,6R,8aR) Ethyl 6-Formyl-2-Methoxycarbonyldecahydroisoquinoline-3-carboxylate A solution of the compound from Example 25A (6.72 g) in acetonitrile (200 ml) was treated with 1N hydrochloric acid (50.5 ml) and heated to 60° C. After about 18 hours, the reaction solution was allowed to cool to room temperature. This mixture was treated with saturated sodium bicarbonate, and the resulting mixture extracted with ether (3 times). The combined ether extracts were dried over magnesium sulfate, filtered, and concentrated in vacuo to give 5.66 g of the title compound.

C. Preparation of (3S,4aR,6S,8aR) Ethyl 6-(2-Cyanoethenyl)-2-methoxycarbonyldecahydroisoquinoline-3-carboxylate A suspension of sodium hydride (0.38 g, 60%), previously washed with hexane, in THF (10 ml) was cooled to. 0° C. The cold suspension was treated with diethyl cyanomethylphosphonate (1.67 g) at 0° C. After 30 minutes, this mixture was allowed to warm to room temperature and treated with a solution of the compound from Example 25B (2.0 g) in THF (5 ml). After 15 minutes, the reaction mixture was treated with water (30 ml) and extracted with ether (3 times). The organic phases were combined, dried over magnesium sulfate, filtered, and concentrated in vacuo to give 2.11 g of the title compound.

D. Preparation of (3S,4aR,6S,8aR) Ethyl 6-(2-Cyanoethyl)-2-methoxycarbonyldecahydroisoquinoline-3-carboxylate A mixture of the compound from Example 25C (62.6 g) and 10% palladium on carbon (15.5 g) in ethyl acetate (125 ml) was hydrogenated at ambient pressure. After six hours at room temperature, the catalyst was removed by filtration through HYFLOW, the HYFLOW filter cake washed with ethyl acetate, and the combined filtrates concentrated in vacuo to give 58.13 g of the title compound. This compound was used in the next step without further purification.

E. Preparation of (3S,4aR,6S,8aR)-6-[2-(1(2)H-Tetrazole-5-yl)ethyl]decahydroisoquinoline-3-carboxylic Acid A mixture of the compounds from Example 25D (1.48 g) and tributyltin azide (2.96 g) was heated to 80° C. After three days, the reaction mixture was treated with toluene (15 ml) and additional tributyltin azide (2 g), and heating resumed. After six days, the reaction was treated with 6N hydrochloric acid (50 ml) and heated to reflux. After heating for about 18 hours, the mixture was allowed to cool to room temperature. This mixture was extracted with ether (6 times) and the aqueous phase concentrated in vacuo. The residue was purified by ion-exchange chromatography on DOWEX 50X8, eluting with 10% pyridine/water. The fractions. containing the title compound were combined and concentrated in vacuo. The residue was diluted with water and concentrated in vacuo. This procedure was repeated. The residue was diluted with acetone and heated to reflux. After heating for one hour, the mixture was filtered and the solids washed with ether. The solid material was dried in vacuo at 60° C. for about 18 hours, to give 1.13 g of the title compound. Melting point 201°–209° C.

$[\alpha]_D$=+20.4° (c=1, 1N HCl)

Analysis calculated for: $C_{13}H_{21}N_5O_2 \cdot 0.75H_2O$: C, 53.32; H, 7.74; N, 23.91. Found: C, 53.29; H, 7.80; N, 24.09.

EXAMPLE 26

(3S,4aR,6S,8aR)-6-[2-(1(2H-Tetrazole-5-yl)-2-thiaethyl]decahydroisoquinoline-3-carboxylic Acid (23)

A. Preparation of (3S,4aR,8aR) Ethyl 6-Methylenyl-2-methoxycarbonyldecahydroisoquinoline-3-carboxylate The reaction of methyltriphenylphosphonium bromide (6.66 g), a 1M solution of sodium bis(trimethylsilyl)amide in THF (18 ml), and the compound from Example 4C (3.1 g) as described in Example 10A produced the crude title compound. This material was purified by silica-gel flash chromatography, eluting with 30% ethyl acetate/hexane, to give 2.88 g of the title compound.

B. Preparation of (3S,4aR,6R,8aR) Ethyl 6-Hydroxymethyl-2-methoxycarbonyldecahydroisoquinoline-3-carboxylate A cold (0° C.) solution of the compound from Example 26A (2.82 g) in THF (40 ml) was treated with a 2.0 molar solution of borane-methyl sulfide in THF (7.5 ml). After three hours, the reaction solution was treated with ether and a mixture of 3N sodium hydroxide (15 ml) and 30% hydrogen peroxide (15 ml). After 15 minutes at 0° C., this mixture was treated with 10% sodium bisulfate (40 ml). The organic phase was separated and the aqueous phase extracted with ether. The organic phases were combined, dried over magnesium sulfate, filtered, and concentrated in vacuo. The residue was purified by silica-gel flash chromatography, eluting with 65% ethyl acetate/hexane, to give 1.34 g of the title compound.

C. Preparation of (3S,4aR,6S,8aR) Ethyl-6-bromomethyl-2-methoxycarbonyldecahydroisoquinoline-3-carboxylate A solution of triphenylphosphine (2.23 g) in methylene chloride (18 ml) was treated with bromine until the yellow color persisted (1.14g). Additional triphenylphosphine was added until the solution became colorless. This solution was treated with the solution of the compound from Example 26B (1.33 g) and pyridine (0.88 g) in methylene chloride (5 ml). The reaction mixture was kept at 0° C. for 25 minutes, then allowed to warm to room temperature. After an additional 25 minutes at room temperature, the reaction mixture was treated with 10% sodium bisulfate (50 ml). The organic phase was removed and the aqueous extracted ether. The organic phases were combined, dried, filtered and concentrated in vacuo. The residue was purified by silica-gel flash chromatography, eluting with 35% ethyl acetate/hexane, to give 1.40 g of the title compound.

D. Preparation of 13S,4aR,6S,8aR) Ethyl 6-[2-(1(2)-H-Tetrazole-5-yl)-2-thiaethyl]-2-methoxycarbonyldecahydroisoquinoline-3-carboxylate A solution of the compound from Example 26C (1.31 g), thiotetrazole (0.41 g), and triethylamine (0.73 g) in anhydrous acetonitrile (12 ml) was heated to 80° C. After 18 hours, the reaction solution was diluted with ethyl acetate, and the resulting mixture extracted with 10% sodium bisulfate. The organic phase was removed and the aqueous extracted with ethyl acetate (two times). The organic phases were combined, dried, filtered, and concentrated in vacuo. The residue was purified by silica-gel flash chromatography, eluting with acetic acid/ethyl acetate/hexane (4:36:60). The fractions containing the desired compound were combined and concentrated in vacuo. The residue was treated with toluene and concentrated in vacuo. This residue was treated with methanol and concentrated in vacuo, followed by ethyl acetate and another concentration in vacuo. The resulting residue was treated with chloroform, and the resulting mixture filtered and the filtrate concentrated in vacuo to give 1.37 g of the title compound.

E. Preparation of (3S,4aR,6S,8aR)-6-[2(1(2)H-Tetrazole-5-yl)-2-thiaethyl]decahydroisoquinoline-3-carboxylic Acid A solution of the compound from Example 26D (1.30 g) in 6N hydrochloric acid (20 ml) was heated to reflux for 4 hours. The solution was allowed to cool to room temperature and concentrated in vacuo. The residue was purified by ion-exchange chromatography on DOWEX 50X8-100, eluting with 10% pyridine/water. The fractions containing the title compound were concentrated in vacuo. The residue was treated with acetone, then heated to reflux for one-half hour. The cooled mixture was filtered and the solid material washed with acetone and ether, then dried in vacuo for about 18 hours at 60° C. to give 0.73 g of the title compound. Melting point 199°–207° C.

$[\alpha]_D = -53.2°$ (c=1, 1N HCl)

Analysis calculated for $C_{12}H_{19}N_5O_2S$: C, 48.47; H, 6.44; N, 23.55. Found: C, 48.37; H, 6.74; N, 23.80.

EXAMPLE 27

(3R,4aS,6R,8aS)-6-[2-(1(2H-Tetrazole-5-yl)-2-thiaethyl]decahydroisoquinoline-3-carboxylic Acid (24)

The title compound (0.81 g) was prepared from the compound from Example 4A using the procedures described in Example 26.

Melting point 165°–172° C.

$[\alpha]_D = +49.3°$ (c=1, 1N HCl)

Analysis calculated for $C_{12}H_{19}N_5O_2S \cdot 0.5H_2O \cdot 0.1C_5H_5$: C, 47.77; H, 6.57; N, 22.72. Found: C, 47.97; H, 6.75; N, 22.75.

EXAMPLE 28

(3S,4aR,6R,8aR)-6[2(1(2)H-Tetrazole-5-yl)-2-thiaethyl]decahydroisoquinoline-3-carboxylic Acid (25)

A. Preparation of (3S,4aR,6R,8aR) Ethyl 6-Hyroxymethyl-2-methoxycarbonyldecahydroisoquinoline-3-carboxylate.

A solution of the compound from Example 25B (1.92 g) in ethanol (19.5 ml) was cooled to 0° C. and treated with sodium borohydride (0.24 g). After 20 minutes, the solution was carefully treated with 10% sodium bisulfate (15 ml). The resulting mixture was extracted with methylene chloride (two times) and ether (two times). The organic extracts were combined, dried over magnesium sulfate, filtered and concentrated in vacuo, to give 1.94 g of the title compound. This material was used in the next step without further purification.

B. Preparation of (3S,4aR,6R,8aR) Ethyl 6-Bromomethyl-2-methoxycarbonyldecahydroisoquinoline-3-carboxylate A solution of triphenylphosphine (4.72 g) in methylene chloride (10.5 ml) was treated with bromine until the yellow color persisted (2.58 g). Additional triphenylphosphine was added until the solution became colorless. This solution was treated with a solution of the compound from Example 28A (1.93 g) and pyridine (1.53 g) in methylene chloride (10.5 ml). After two hours at room temperature, the reaction mixture was extracted with 10% sodium bisulfite. The aqueous extract was extracted with ether (3 times). The ether extracts were combined with the organic phase, dried over magnesium sulfate, filtered, and concentrated in vacuo. The residue was treated with ether and the precipitated triphenylphosphine oxide removed by filtration. The filtrate was concentrated in vacuo and the residue taken up in additional ether to precipitate the remaining traces of triphenylphosphine oxide. The residue was purified by silica-gel flash chromatography, eluting with 35% ethyl acetate/hexane, to give 1.56 g of the title compound.

C. Preparation of (3S,4aR,6R,8aR) Ethyl 6-[2-(1(2 H-Tetrazole-5-yl)-2-thiaethyl]-2-methoxycarbonyldecahydroisoquinoline-3-carboxylate A solution of the compound from Example 28B (1.56 g), thiotetrazole (0.53 g), and triethylamine (0.96 g) in anhydrous acetonitrile (13 ml) was heated to 80° C. After four hours, the reaction solution was partitioned between ethyl acetate and 10% sodium bisulfate. The phases were separated and the aqueous phase extracted with additional ethyl acetate (3 times). The ethyl acetate extracts were combined, dried over magnesium sulfate, filtered, and concentrated in vacuo. The residue was split into two portions and each purified by silica-gel radial chromatography on a CHROMATOTRON (4 mm plate) equilibrating the plate with 35 ethyl acetate/hexane and eluting with acetic acid/ethyl acetate/hexane (4:36:60), to give 1.14 g of the title compound.

D. Preparation of (3S,4aR,6R,8aR)-6-[2-(1(2)H-Tetrazole-5-yl)-2-thiaethyl]decahydroisoquinoline-3-carboxylic Acid A solution of the compound from Example 28C (1.14 g) in 6N hydrochloric acid (50 ml) was heated to 100° C. After heating for about 18 hours, the reaction solution was allowed to cool to room temperature and concentrated in vacuo. The residue was purified by ion-exchange chromatography on DOWEX 50X8, eluting with 10% pyridine/water. The fractions containing the title compound were concentrated in vacuo. The residue was treated with water and concentrated in vacuo. This procedure was repeated. The residue was treated with acetone, and the resulting mixture heated to reflux for one hour. After cooling to room temperature, the mixture was filtered. The solid material was washed with acetone and ether, then dried in vacuo at 60° C. to give 0.197 g of the title compound.

$[\alpha]_D = +34.6°$ (c=1, 1N HCl)

Analysis calculated for $C_{12}H_{19}N_5O_2S \cdot 0.3H_2O$: C, 47.6; H, 6.52, N, 23.13. Found: C, 47.35; H, 6.23; N, 23.10.

EXAMPLE 29

(3S,4aR,6S,8aR)-6-[(1(2-4)H-1,2,4-Triazole-5-yl)sulfonylmethyl]decahydroisoquinoline-3-carboxylic Acid (26)

A. Preparation of (3S,4aR,6S,8aR) Ethyl 6-[2-(1(2)H-Triazole-5-yl)-2-thiaethyl]-2-methoxycarbonyldecahydroisoquinoline-3-carboxylate A solution of the compound from Example 26C (2.80 g) in anhydrous dimethylformamide (23 ml) was treated with 1H-1,2,4-triazole-3-thiol (0.94 g) and triethylamine (1.88 g). The resulting solution was heated to 100° C. under a nitrogen atmosphere. After four hours, the reaction solution was allowed to cool to room temperature and treated with 10% sodium bisulfate. The resulting mixture was extracted with chloroform/ethyl acetate (1:1). The organic phases were combined, dried over magnesium sulfate, filtered, and concentrated in vacuo. The residue was purified by silica-gel flash chromatography, eluting with a step gradient of 35% ethyl acetate/hexane (500 ml) followed by 75% ethyl acetate/hexane (2 L), to give 2.72 g of the title compound.

B. Preparation of (3S,4aR,6S,8aR)-6-[(1(2-4)H-1,2,4-Triazole-5-yl)sulfonylmethyl]decahydroisoquinoline-3-carboxylic Acid A solution of the compound from Example 29A (2.72 g) in methylene chloride was treated with 3-chloroperoxybenzoic acid (3.84 g) in three portions over a period of 30 minutes. After about 18 hours at room temperature, the reaction mixture was concentrated in vacuo. The residue was purified by silica-gel flash chromatography, eluting with a step-gradient of 50% ethyl acetate/hexane (200 ml) followed by ethyl acetate (200 ml) and 2.5% acetic acid/ethyl acetate (500 ml). The fractions containing the product were combined and concentrated in vacuo. The residue was treated with toluene/methanol and concentrated in vacuo. This residue was treated with methanol and concentrated in vacuo, and then chloroform and concentrated in vacuo, to give 2.50 g.

The product from the preceding paragraph was treated with 6N hydrochloric acid (50 ml) and heated to 110° C. After three hours, the reaction mixture was allowed to cool to room temperature and extracted with ether. The aqueous phase was concentrated in vacuo. The residue was purified by ion-exchange chromatography on DOWEX 50X8-100, eluting with 10% pyridine/water. The fractions containing the title compound were combined and concentrated in vacuo. The residue was diluted with water and concentrated in vacuo. This process was repeated two times, and the residue concentrated in vacuo for about 18 hours. This residue was diluted with acetone and refluxed for one hour. The title compound was removed by filtration then washed with acetone and ether. The solids were dried in vacuo at 60° C. for about 18 hours to give 1.60 g of the title compound. Melting point 286°–287° C.

$[\alpha]_D = -39.4°$ (c=1, 1N HCl)

Analysis calculated for $C_{13}H_{20}N_4O_4S \cdot 0.6H_2O$: C, 46.03; H, 6.30; N, 16.52. Found: C, 46.13; H, 6.37; N, 16.17.

EXAMPLE 30

(3R,4aS,6R,8aS)-6-[(1(2-4)H-1,2,4-Triazole-5-yl) sulfonylmethyl]decahydroisoquinoline-3-carboxylic Acid (27)

The title compound (1.16 g) was prepared from the compound from Example 4A using the procedures described in Examples 26A–26C and 29. Melting point 267°–270° C.

$[\alpha]_D = +33.8°$ C. (c=1, 1N HCl)

Analysis calculated for $C_{13}H_{20}N_4O_4S \cdot H_2O$: C, 45.08; H, 6.40; N, 16.17. Found: C, 45.47; H, 6.57; N, 16.16.

We claim:

1. A process for the preparation of a compound of the formula

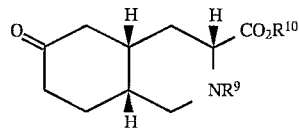

VIII wherein:

$R^9$ is acyl or alkoxycarbonyl; and $R^{10}$ is hydrogen, $C_1$–$C_6$ alkyl, or aryl;

which comprises stereoselectively reducing a compound of formula

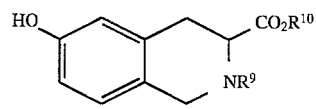

VI wherein $R^9$ and $R^{10}$ are as defined previously, by catalytic hydrogenation using rhodium on carbon as hydrogenation catalyst.

2. A process as claimed in claim 1, in which the reduction is carried out at a hydrogen pressure of about 30 psi to about 200 psi and at a temperature of about 70° C. to about 90° C.

3. A process as claimed in claim 2, in which the reduction is carried out at a hydrogen pressure of about 100 psi and a temperature of about 85° C.

4. A process as claimed in claim 1, in which the reduction is carried out in a polar organic solvent.

5. A process as claimed in claim 4, in which the polar organic solvent is selected from ethyl acetate, methanol, and ethanol.

6. A process as claimed in claim 1, in which $R^9$ is methoxycarbonyl, $R^{10}$ is ethyl and the reduction is carried out at a hydrogen pressure of about 30 psi to about 200 psi and at a temperature of about 70° C. to about 90° C. in a polar organic solvent.

* * * * *

UNITED STATES PATENT AND TRADEMARK OFFICE
CERTIFICATE OF CORRECTION

PATENT NO. : 5,637,712

DATED : June 10, 1997

INVENTOR(S) : Carl F. Bertsch, et al.

It is certified that error appears in the above-identified patent and that said Letters Patent is hereby corrected as shown below:

Column 10, line 65, delete "methoxycarbonyldecahydroisocfuinoline" and insert therefore --methoxycarbonyldecahydroisoquinoline--.

Column 21, line 5, delete "produce" and insert therefore--product--.

Column 22, line 10, delete "chloroformares" and insert therefore--chloroformates--.

Column 25, line 39, delete "hydromy" and insert therefore--hydroxy--.

Column 39, line 12, delete "HO2C" and insert therefore--HO3S--.

Column 59, line 51, delete ")-e-[" and insert therefore--)-6-[--.

Column 59, line 53, insert after `Acid' --(9)--.

Column 65, line 59, delete "(1.99g)" and insert therefore--(1.95g)--.

Column 73, line 32, delete "am" and insert therefore--at--.

Column 77, line 50, delete "SaR" and insert therefore--8aR--.

Signed and Sealed this

Eleventh Day of May, 1999

Attest:

Q. TODD DICKINSON

*Attesting Officer*     *Acting Commissioner of Patents and Trademarks*